(12) United States Patent
Rubin et al.

(10) Patent No.: US 11,426,400 B2
(45) Date of Patent: *Aug. 30, 2022

(54) METHODS OF INCREASING SATELLITE CELL PROLIFERATION WITH VORINOSTAT OR BOSUTINIB

(71) Applicant: PRESIDENT AND FELLOWS OF HARVARD COLLEGE, Cambridge, MA (US)

(72) Inventors: Lee L. Rubin, Wellesly, MA (US); Amanda Gee, Alexandria, VA (US); Amy J. Wagers, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 122 days.

This patent is subject to a terminal disclaimer.

(21) Appl. No.: 16/882,707

(22) Filed: May 25, 2020

(65) Prior Publication Data

US 2020/0352957 A1 Nov. 12, 2020

Related U.S. Application Data

(63) Continuation of application No. 15/728,476, filed on Oct. 9, 2017, now Pat. No. 10,660,902, which is a continuation of application No. 15/012,656, filed on Feb. 1, 2016, now Pat. No. 9,782,417, which is a continuation-in-part of application No. 14/126,716, filed as application No. PCT/US2012/042964 on Jun. 18, 2012, now Pat. No. 9,248,185.

(60) Provisional application No. 61/497,708, filed on Jun. 16, 2011.

(51) Int. Cl.

| | | |
|---|---|---|
| *A61P 21/06* | (2006.01) | |
| *A61K 31/167* | (2006.01) | |
| *A61K 31/4709* | (2006.01) | |
| *A61K 31/47* | (2006.01) | |
| *A61K 31/16* | (2006.01) | |
| *A61K 31/165* | (2006.01) | |
| *A61K 31/553* | (2006.01) | |
| *A61K 31/404* | (2006.01) | |
| *A61K 31/496* | (2006.01) | |
| *A61K 31/4439* | (2006.01) | |
| *A61K 45/06* | (2006.01) | |
| *A61K 31/136* | (2006.01) | |
| *A61K 31/4164* | (2006.01) | |
| *A61K 31/485* | (2006.01) | |
| *A61K 31/58* | (2006.01) | |
| *A61K 31/7076* | (2006.01) | |
| *C07C 259/04* | (2006.01) | |

(52) U.S. Cl.
CPC .......... *A61K 31/4709* (2013.01); *A61K 31/16* (2013.01); *A61K 31/165* (2013.01); *A61K 31/167* (2013.01); *A61K 31/47* (2013.01); *A61P 21/06* (2018.01); *A61K 31/136* (2013.01); *A61K 31/404* (2013.01); *A61K 31/4164* (2013.01); *A61K 31/4439* (2013.01); *A61K 31/485* (2013.01); *A61K 31/496* (2013.01); *A61K 31/553* (2013.01); *A61K 31/58* (2013.01); *A61K 31/7076* (2013.01); *A61K 45/06* (2013.01); *C07C 259/04* (2013.01)

(58) Field of Classification Search
CPC .... A61K 31/47; A61K 31/4709; A61K 31/16; A61K 31/165; A61K 31/167; A61P 21/06
See application file for complete search history.

(56) References Cited

U.S. PATENT DOCUMENTS

| | | |
|---|---|---|
| 9,248,185 B2 | 2/2016 | Rubin et al. |
| 9,782,417 B2 | 10/2017 | Rubin et al. |
| 10,660,902 B2 | 5/2020 | Rubin et al. |
| 2003/0181510 A1 | 9/2003 | Baker et al. |
| 2005/0281788 A1 | 12/2005 | De Bari et al. |
| 2007/0224168 A1 | 9/2007 | Montarras et al. |
| 2009/0306087 A1 | 12/2009 | Ibrahim et al. |
| 2010/0048534 A1 | 2/2010 | Dziki et al. |
| 2014/0294855 A1 | 10/2014 | Rubin et al. |
| 2016/0220580 A1 | 8/2016 | Rubin et al. |
| 2018/0153902 A1 | 6/2018 | Rubin et al. |
| 2019/0365777 A1 | 12/2019 | Rubin et al. |

FOREIGN PATENT DOCUMENTS

| | | |
|---|---|---|
| RU | 2368398 C1 | 9/2009 |
| WO | WO-2011/109834 A2 | 9/2011 |
| WO | WO-2012/030919 A2 | 3/2012 |
| WO | WO-2012/174537 A2 | 12/2012 |
| WO | WO-2015/006752 A1 | 1/2015 |
| WO | WO-2017/136480 A1 | 8/2017 |

OTHER PUBLICATIONS

Final Office Action for U.S. Appl. No. 16/074,766 dated Dec. 28, 2020.

Riessland, et al., "SAHA Ameliorates the SMA Phenotype in Two Mouse Models for Spinal Muscular Atrophy," *Human Molecular Genetics*, 19(8):1492-1506, (2010).

(Continued)

*Primary Examiner* — Zachary C Howard

(74) *Attorney, Agent, or Firm* — Morse, Barnes-Brown & Pendleton, P.C.; Lisa M. Warren, Esq.; Erin E. Bryan, Esq.

(57) ABSTRACT

The invention provides methods for inducing, enhancing or increasing satellite cell proliferation, and an assay for screening for a candidate compound for inducing, enhancing or increasing satellite cell proliferation. Also provided are methods for repairing or regenerating a damaged muscle tissue of a subject.

10 Claims, 44 Drawing Sheets

(56) References Cited

OTHER PUBLICATIONS

Bentzinger, et al., "Extrinsic regulation of satellite cell specification" Stem Cell Research & Therapy, 2010, 1 :27 [online] Retrieved from the Internet: <URL: http:www.ncbi.nlm.nih.gov/pubmed/20804582>.

Carlson, et al., "Relative roles of TGF-β1 and Wnt in the systemic regulation and aging of satellite cell responses," *Aging Cell*, 8:676-689, (2009).

Consalvi, et al., "Histone Deacetylase Inhibitors in the Treatment of Muscular Dystrophies: Epigenetic Drugs for Genetic Diseases," *Mol. Med.*, 17(5-6):457-465, (May-Jun. 2011).

Cosgrove, et al., "Rejuvenation of the Muscle Stem Cell Population Restores Strength to Injured Aged Muscles," *Nature Medicine*, 20:255-264, (Mar. 1, 2014).

Elia, et al., "Sonic hedgehog promotes proliferation and differentiation of adult muscle cells: Involvement of MAPK/ERK and PI3K/Akt pathways" *Biochimica et Biophysica Acta*, 1773:1438-1446, (2007).

Mulligan, "RET revisited: expanding the oncogenic portfolio," *Nature*, 74:173-186, (Mar. 2014).

Shea, et al., "Sprouty1 Regulates Reversible Quiescence of a Self-Renewing Adult Muscle Stem Cell Pool during Regeneration," *Cell Stem Cell*, 6:117-129, (Feb. 5, 2010).

Strock, et al., "CEP-701 and CEP-751 Inhibit Constitutively Activated RET Tyrosine Kinase Activity and Block Medullary Thyroid Carcinoma Cell Growth," *Cancer Research*, 63:5559-5563, (Sep. 1, 2003).

International Search Report for International Application PCT/US12/42964, dated Dec. 20, 2012.

International Search Report from PCT/US2017/016099, dated Apr. 14, 2017.

Non-Final Office Action for U.S. Appl. No. 14/126,716, dated Apr. 30, 2015.

Notice of Allowance for U.S. Appl. No. 14/126,716, dated Oct. 20, 2015.

Non-Final Office Action for U.S. Appl. No. 15/012,656, dated Oct. 7, 2016.

Final Office Action for U.S. Appl. No. 15/012,656, dated Feb. 22, 2017.

Notice of Allowance for U.S. Appl. No. 15/012,656, dated Jun. 1, 2017.

Non-Final Office Action for U.S. Appl. No. 15/728,476, dated Aug. 2, 2018.

Final Office Action for U.S. Appl. No. 15/728,476, dated Oct. 11, 2019.

Notice of Allowance for U.S. Appl. No. 15/728,476, dated Jan. 14, 2020.

Notice of Allowance for U.S. Appl. No. 15/728,476, dated Feb. 25, 2020.

Notice of Allowance for U.S. Appl. No. 16/074,766, dated Feb. 11, 2021.

Non-Final Office Action for U.S. Appl. No. 16/074,766, dated Jul. 27, 2020.

Cheriyan, et al., "Inhibition of p38 Mitogen-Activated Protein Kinase Improves Nitric Oxide-Mediated Vasodilatation and Reduces Inflammation in Hypercholesterolemia," *Circulation*, pp. 515-523, (Feb. 8, 2011).

- Screened ~400 compounds
- Identified ~10 primary hits
  - Increase proliferation
  - Work in resupply
  - Work in dose response
- Identified additional secondary hits
- Increase proliferation 1.5-3.0 fold

- Satellite cells cultured for 24hrs *in vitro*.
- Treated with GDNF +/- CEP for different amounts of time.

METHODS OF INCREASING SATELLITE CELL PROLIFERATION WITH VORINOSTAT OR BOSUTINIB

RELATED APPLICATIONS

This application is a continuation of U.S. application Ser. No. 15/728,476, filed Oct. 9, 2017, which is a continuation of U.S. application Ser. No. 15/012,656, filed Feb. 1, 2016, which is a continuation-in-part of, and claims priority to, co-pending U.S. patent application Ser. No. 14/126,716, filed Jun. 13, 2014, which is a national stage filing under 35 U.S.C. 371 of International Application No. PCT/US2012/042964, filed Jun. 18, 2012, which claims benefit under 35 U.S.C. § 119(e) of U.S. Provisional Application No. 61/497,708, filed Jun. 16, 2011, the contents of which are incorporated herein by reference in their entirety.

GOVERNMENT SUPPORT

This invention was made with government support under HL127365 awarded by the National Institutes of Health. The government has certain rights in the invention.

TECHNICAL FIELD

The present disclosure relates generally to compositions and methods of promoting satellite cell proliferation.

BACKGROUND

Satellite cells are a population of skeletal muscle stem cells that are located beneath the basal lamina surrounding the muscle fiber and are required for muscle growth and muscle repair after injury or exercise. Satellite cell number and function are affected by normal aging and in several diseases, resulting in progressive muscle wasting or inefficient recovery after injury. Examples include Duchenne muscular dystrophy, in which satellite cells are depleted through constant use, and sarcopenia, where satellite cells may both be depleted and adversely affected in their proliferative capacity by changes in their environment (Jejurikar and Kuzon, Apoptosis, 8 (2003), 573-578). Finding treatments that would expand the endogenous population of satellite cells could aid greatly in treating these debilitating diseases.

Thus, there is need in the art for compositions and methods for inducing satellite cell proliferation.

SUMMARY

The inventors conducted an image-based screen of selected small molecules for their ability to increase proliferation in satellite cells isolated from adult mouse muscle tissue. Satellite cells were isolated using cell surface markers (Sherwood et al., Cell, 119 (2004), 543-554), cultured in the presence of small molecules for four days, and then analyzed using automated confocal microscopy to determine cell number. Using this procedure, the inventors discovered several compounds, operating through defined signaling pathways, which can enhance proliferation in cultures of primary mouse satellite cells. The myogenic capacity of treated cells is currently being tested through marker analysis and differentiation assays, as well as in vivo muscle grafting. The compounds are capable of proliferating cells without adversely affecting their differentiation potential and can be used for treatment of diseases having a skeletal muscle defect as one of their components. These compounds are also referred to as proliferation enhancers herein.

Accordingly, presented herein is a method of inducing, enhancing or increasing satellite cell proliferation. The method comprising contacting a satellite cell with a compound selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, adenosine receptor agonists, ionophores, ion channel modulators, gamma-secretase modulators, corticosteroids, and any combinations thereof. The satellite cell to be contacted can be in vitro, ex vivo or in vivo.

In another aspect, provided herein is a method for repairing or regenerating a damaged muscle tissue of a subject. The method comprising administering to the subject a therapeutically effective amount of a compound selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, ionophores, ion channel modulators, gamma-secretase modulators, and any combinations thereof.

In yet another aspect, provided herein is a method of screening for a candidate compound for inducing, enhancing or increasing satellite cell proliferation. The method comprising: (a) contacting a population of satellite cells with a test compound; (b) assessing satellite proliferation; and (c) selecting the compound that induces, increases or enhances satellite cell proliferation.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1A:
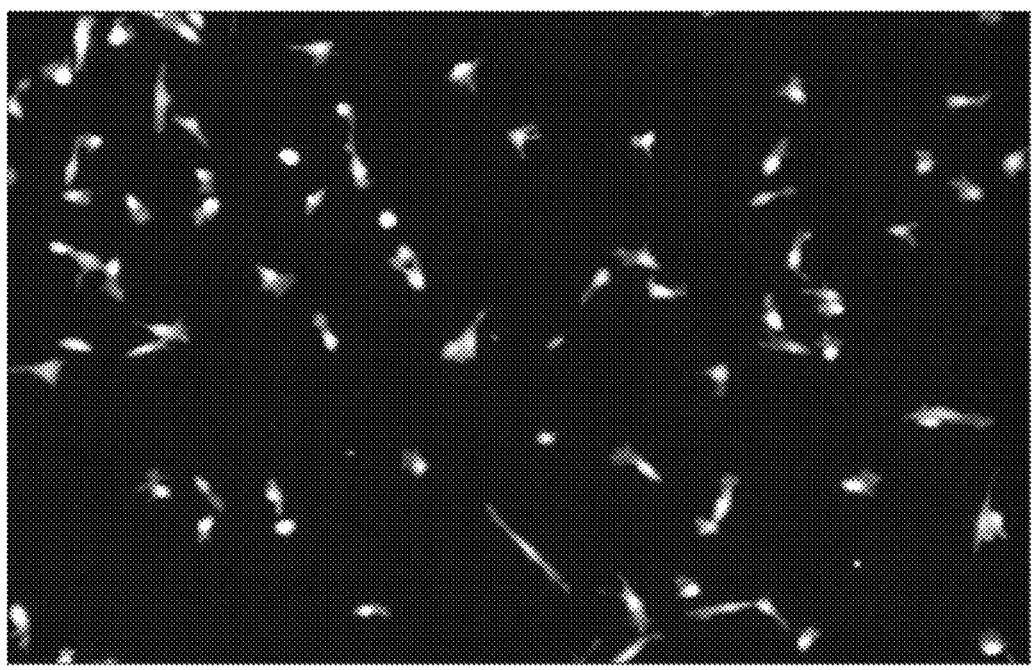
FIGS. 1A-1C show Opera analysis of satellite cell number. Images were captured using the Perkin Elmer Opera automated confocal imaging system. Since all cells isolated from the CAG-EGFP animals were fluorescent, the inventors could image the cells directly (FIG. 1A). Images were analyzed using Acapella software to count cells that had signals within the set thresholds for each parameter (FIG. 1B). Cells or debris that were too dim (arrow), or too small (arrowheads) were excluded. Cells and debris that were highly fluorescent or too large in size were also excluded. Cells could then be further grouped according to set criteria, such as roundness (FIG. 1C).
Figure 1B:
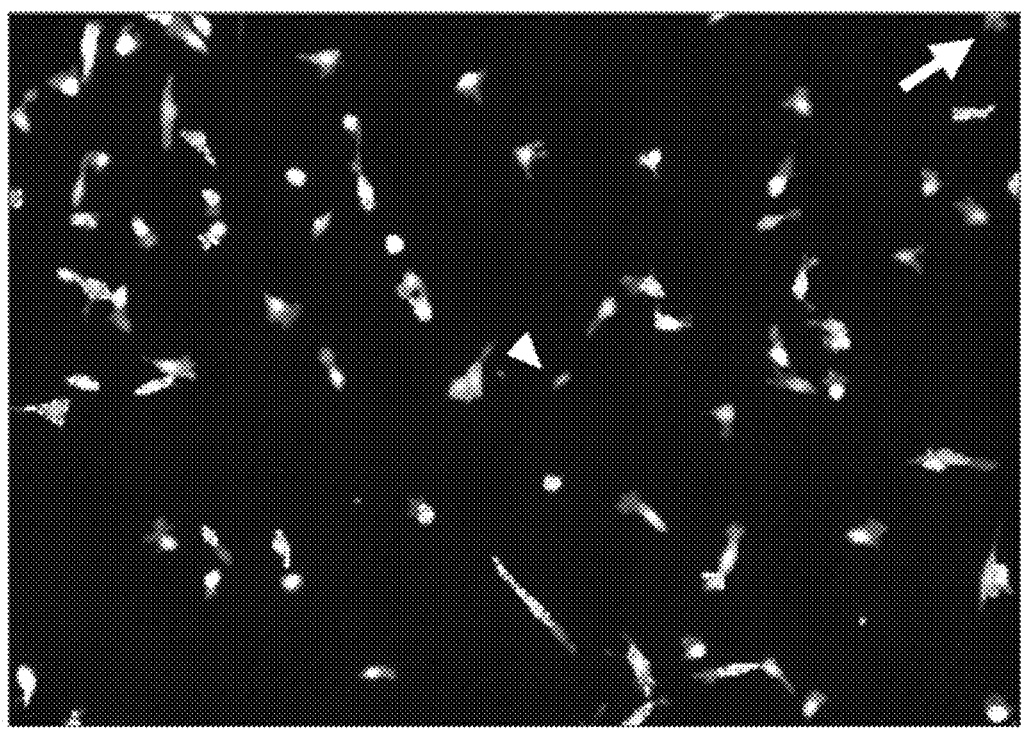
Figure 1C:
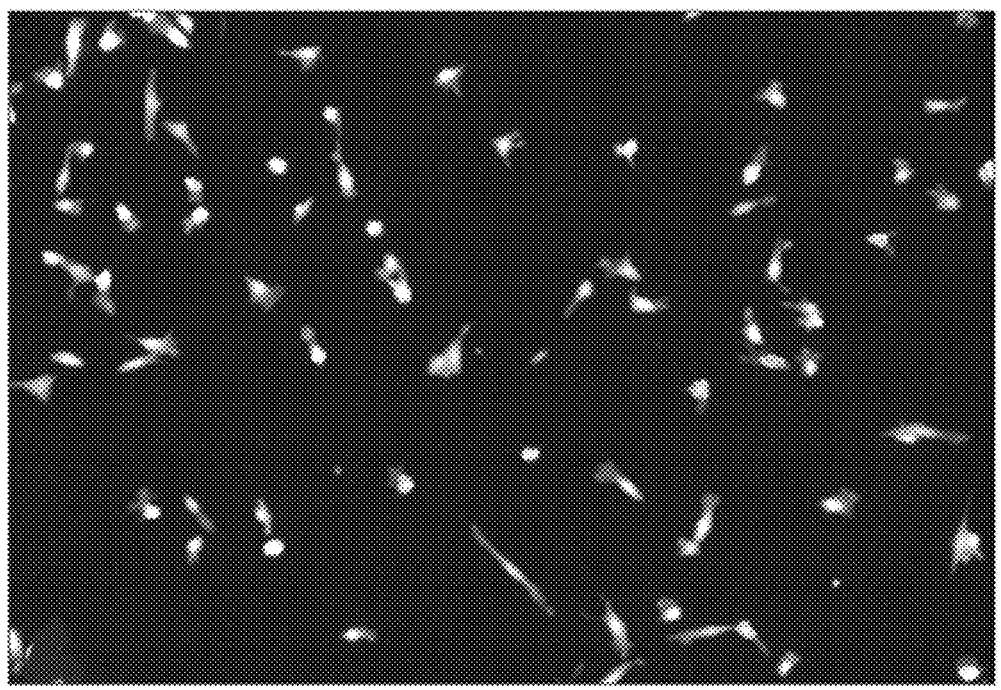
Figure 2A:
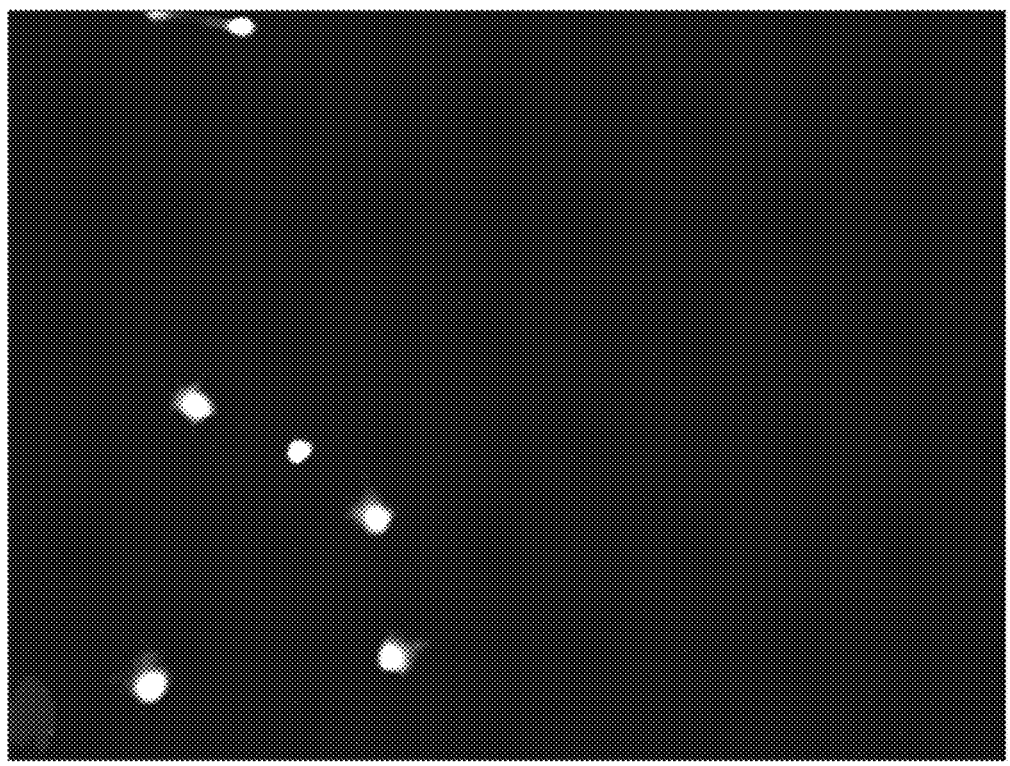
FIGS. 2A-2D show analysis of positive hit compounds. Adult mouse satellite cells were isolated via FACS, based on the procedure outlined in Sherwood et al. (Cell, 119 (2004), 543-554). Then, cells were treated with compounds and allowed to proliferate for four days, fixed, and imaged. Proliferation induced by compounds was compared to that found with a DMSO vehicle control (FIG. 2A), or to that found with bFGF (FIG. 2B). Two example images from positive hit compounds are shown, Flt3 Kinase inhibitor (FIG. 2C) and Adenosine receptor agonist (FIG. 2D).
Figure 2B:
Figure 2C:
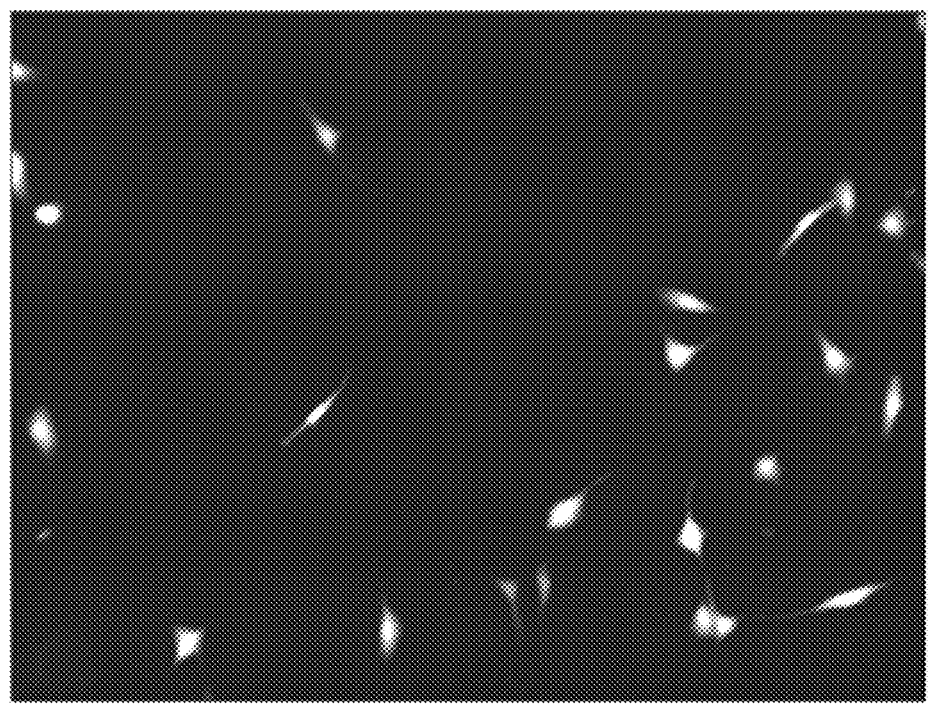
Figure 2D:
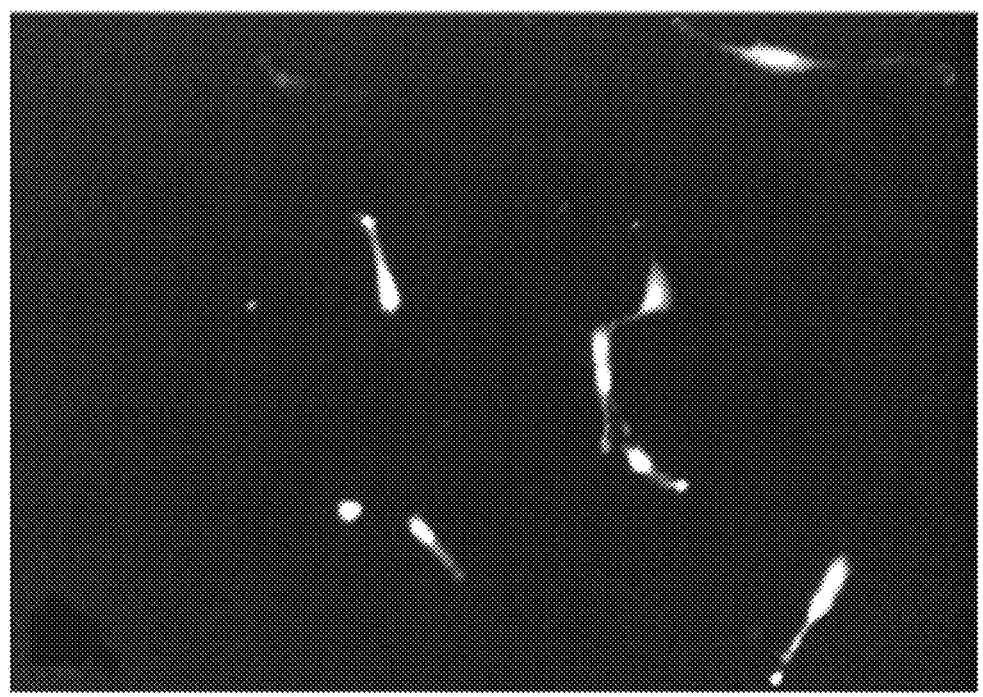
Figure 3A:
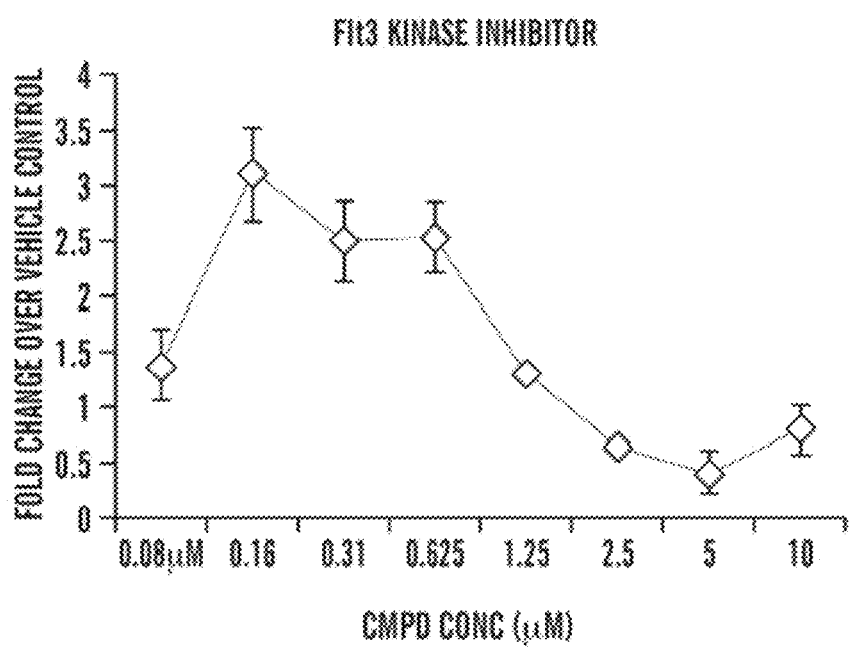
FIGS. 3A and 3B show validation of some exemplary hit compounds. Compounds identified in the primary screen as hits were then tested in a dose response assay. The level of proliferation is measured as fold change over the DMSO vehicle control value of (A.1±0.3 (FIG. 3A) and 1±0.4 (FIG.
Figure 3B:
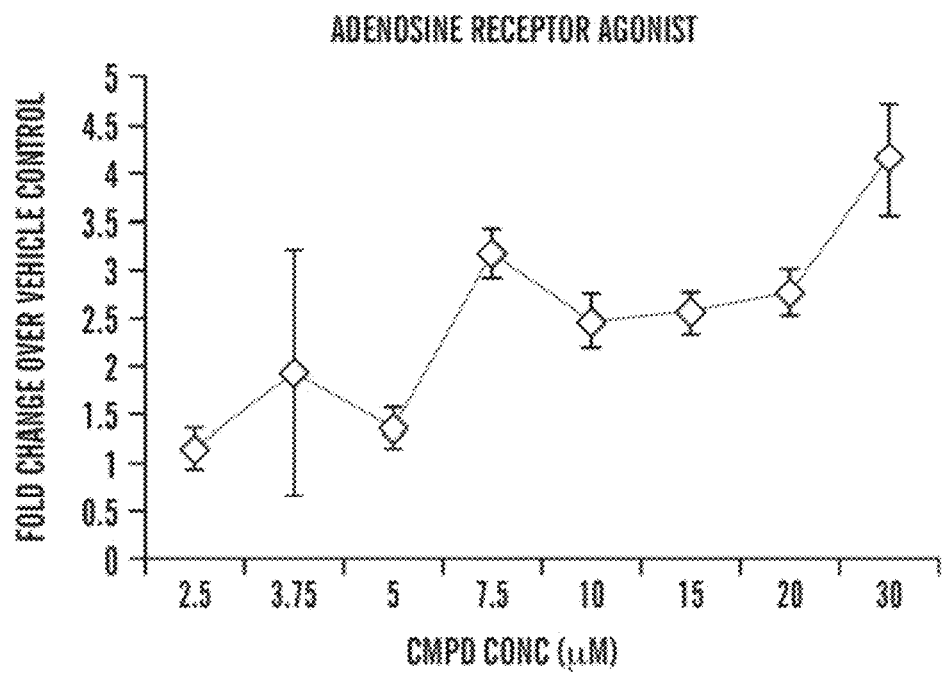

3B). For comparison, the bFGF positive control values were 3.4±0.9 (FIG. 3A) and 5.6±1.7 (FIG. 3B).

Figure 4:
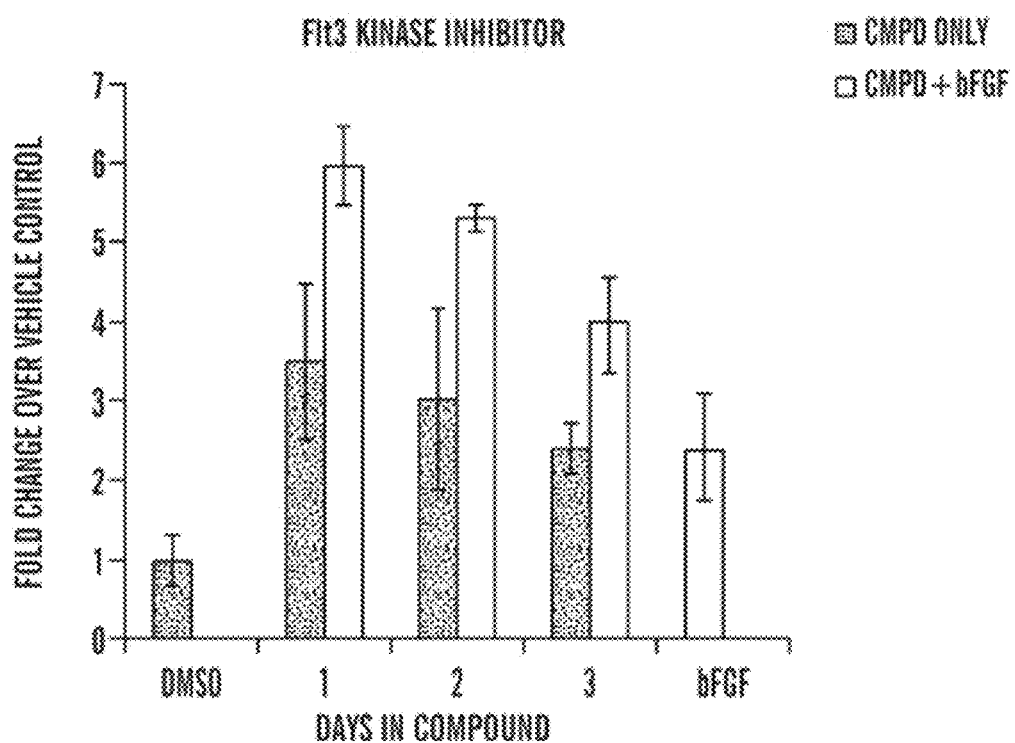

FIG. 4 shows optimization of culture conditions. Culture conditions were optimized by testing the effects of compounds with differential exposure time, with or without the presence of bFGF. For all time points, media were replaced with standard proliferation medium on the indicated days. For this compound, the inclusion of bFGF had an additive effect on proliferation. Also, while the compound itself led to proliferation similar to the bFGF positive control at all time points, it was seen to be more effective with a shorter exposure time.

Figure 5A:
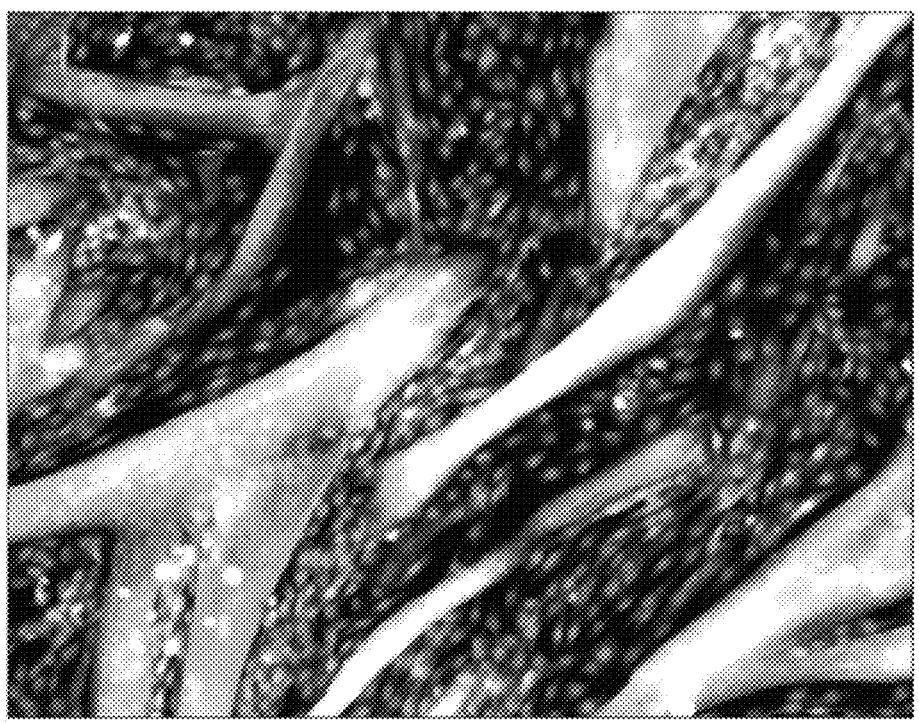
Figure 5B:
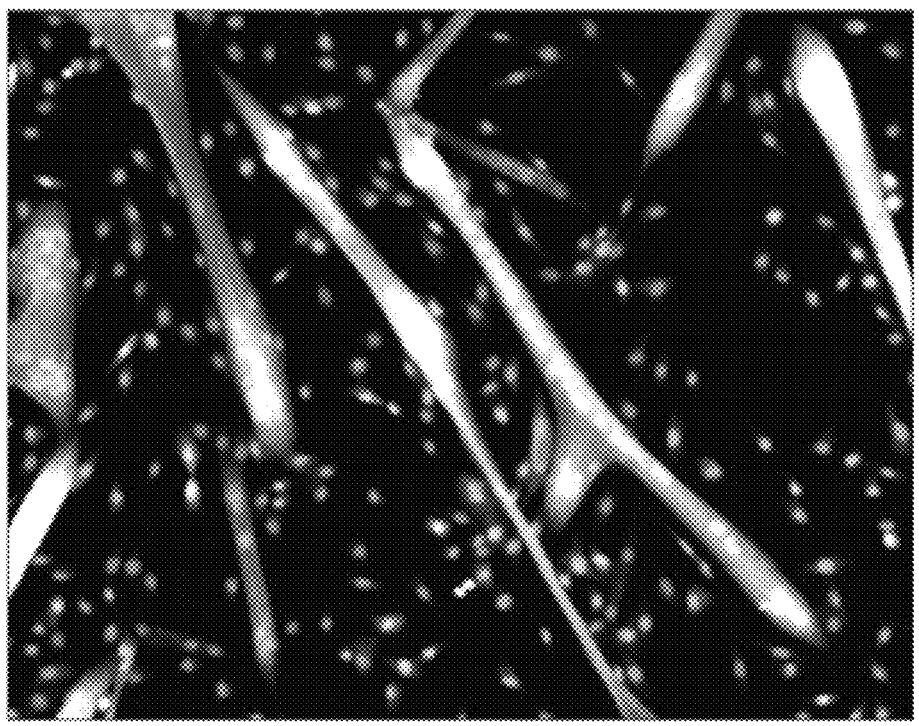
Figure 5C:
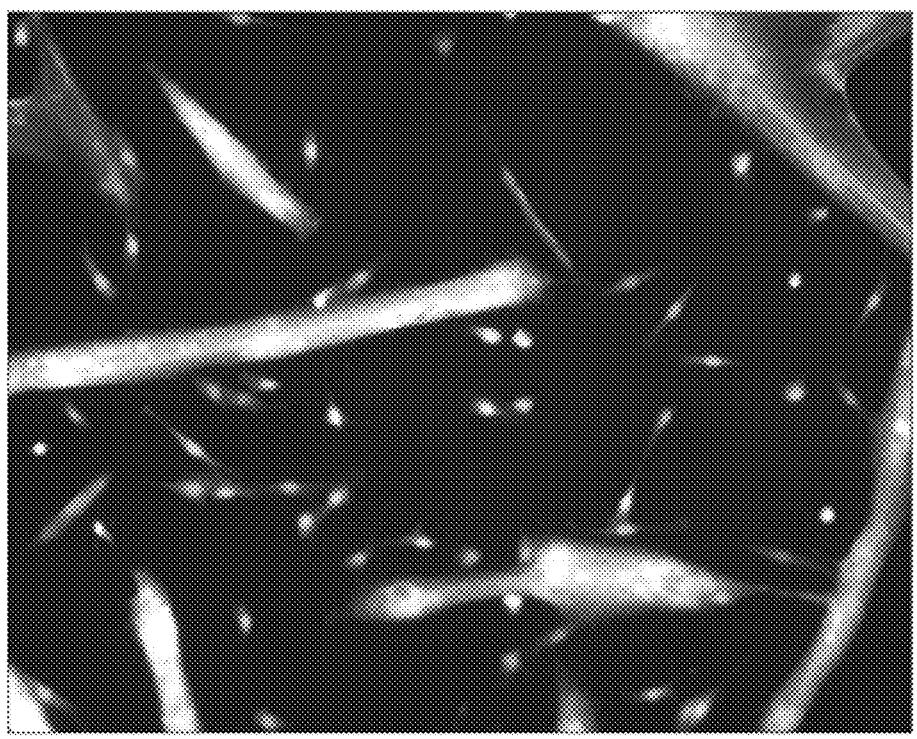

FIGS. 5A-5C show differentiation of treated cultures. CAG-EGFP satellite cells were grown in the inventors' standard proliferation conditions and exposed to compounds for four days. Under the inventors' standard proliferation conditions cells were cultured on laminin-coated plates in Ham's F-10 medium supplemented with 10% heat inactivated horse serum, 100 Units/mL penicillin/100 ug/mL streptomycin, and 2 mM L-glutamine. Compounds were added the day after plating. The compounds and media were either refreshed daily or after three days. To differentiate cells and form myotubes, after four days in proliferation conditions, media was switched to high-glucose DMEM supplemented with 10% heat inactivated horse serum, 10% fetal bovine serum, 0.5% chick embryo extract, 100 Units/mL penicillin/100 ug/mL streptomycin, and 2 mM L-glutamine. Cultures were grown in differentiation media for 3-5 days until myotube formation was observed, then fixed. Cultures were then switched into differentiation media and cultured another four days. They were then fixed and stained with anti-myosin heavy chain (red channel) and Hoechst (blue channel). Cells grown with only DMSO vehicle control did not form myotubes because they were not dense enough in culture (data not shown). Cells grown in the presence of bFGF positive control (FIG. 5A) were able to form large myotubes. Cultures grown in the presence of Flt3 Kinase inhibitor (FIG. 5B) and adenosine agonist (FIG. 5C) were able to form myotubes as well.

Figure 6:
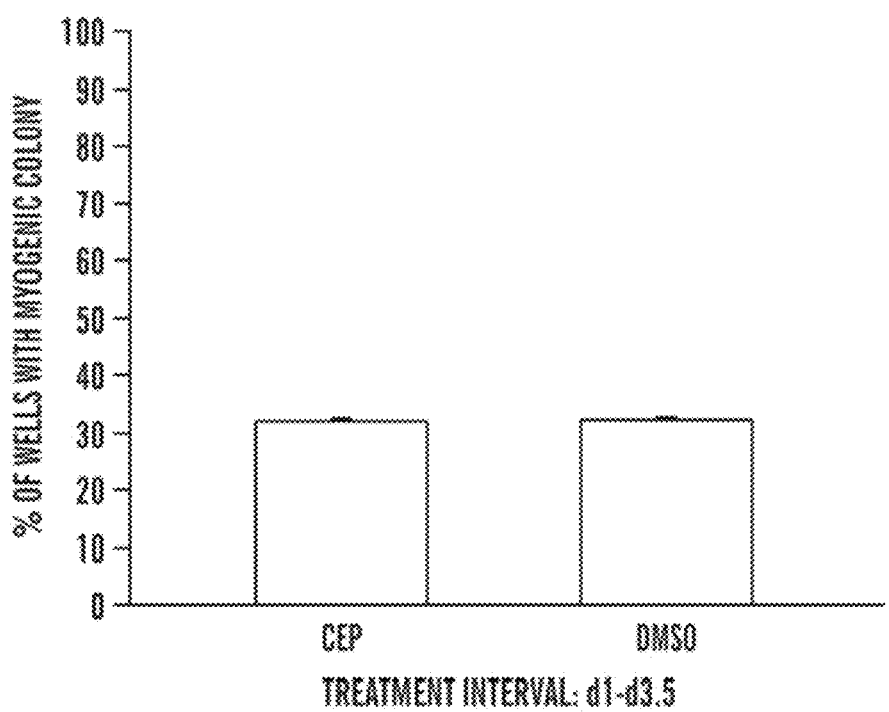

FIG. 6 shows myogenic colony formation of single SMPs treated with CEP/DMSO for 5 days. Treatment interval d1-d3.5 and n=3.

Figure 7:
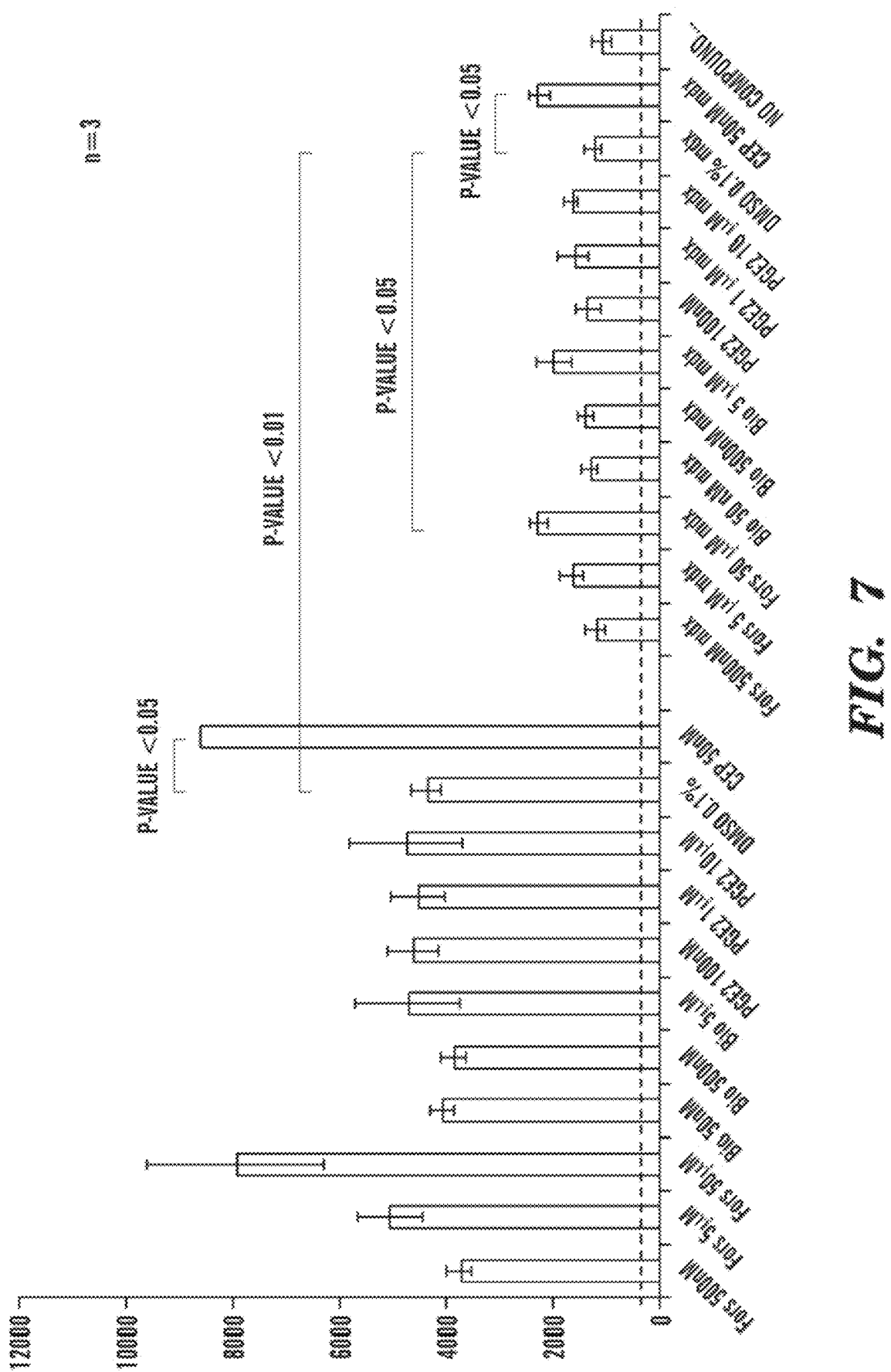

FIG. 7 shows Exposure to compound from d2 to d4.5. Initial cell number was 250 and n=3.

Figure 8A:
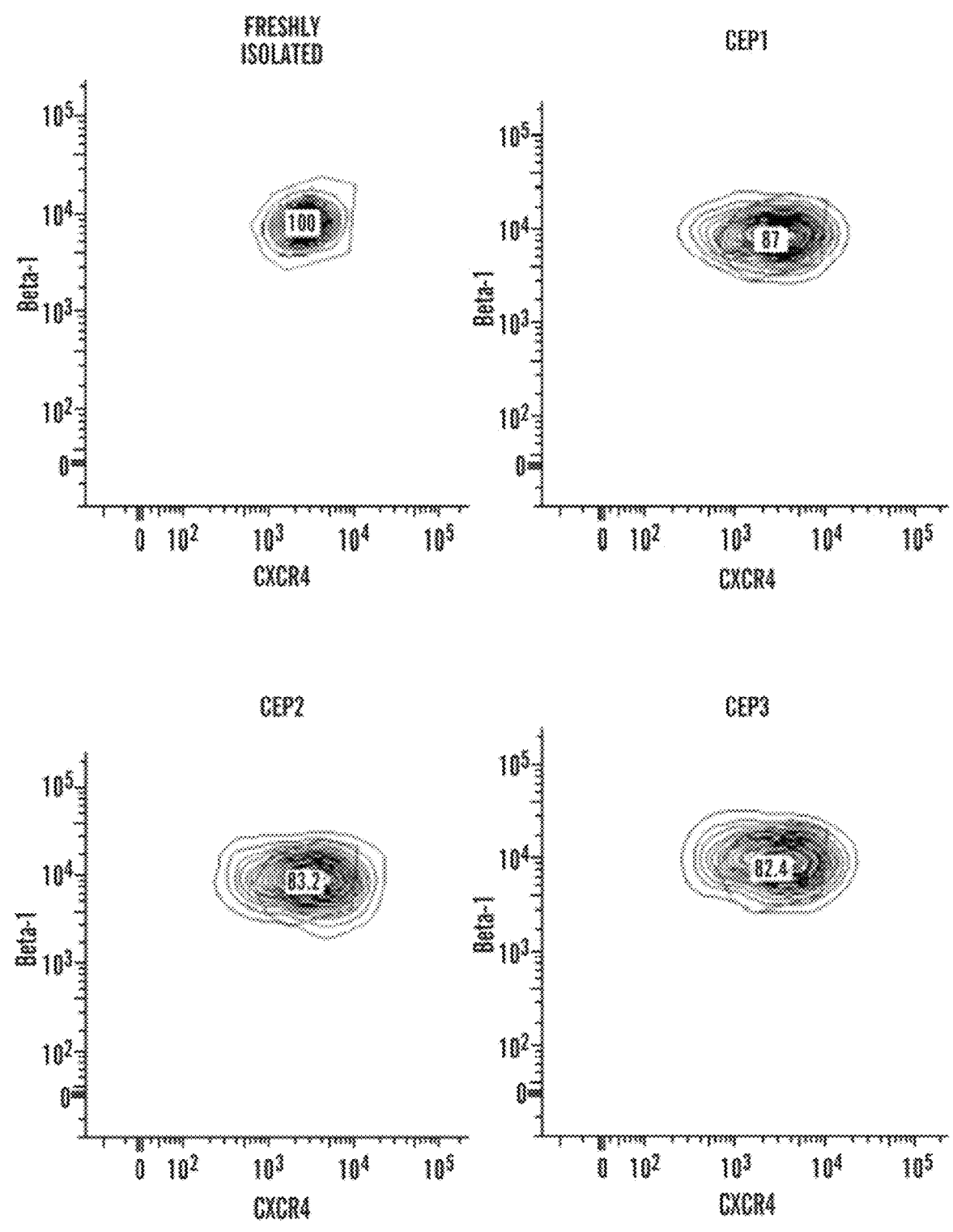
Figure 8B:
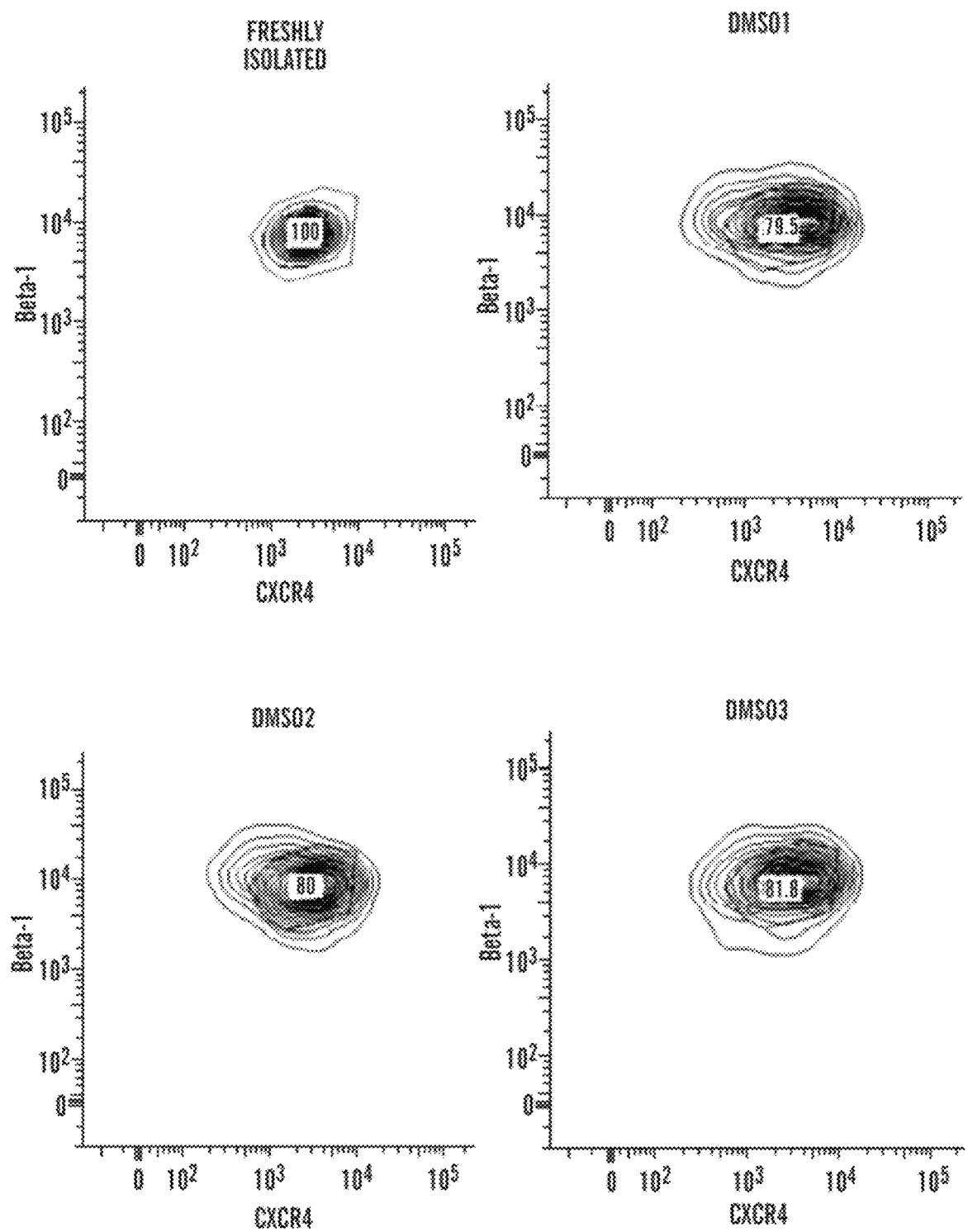
Figure 9A:
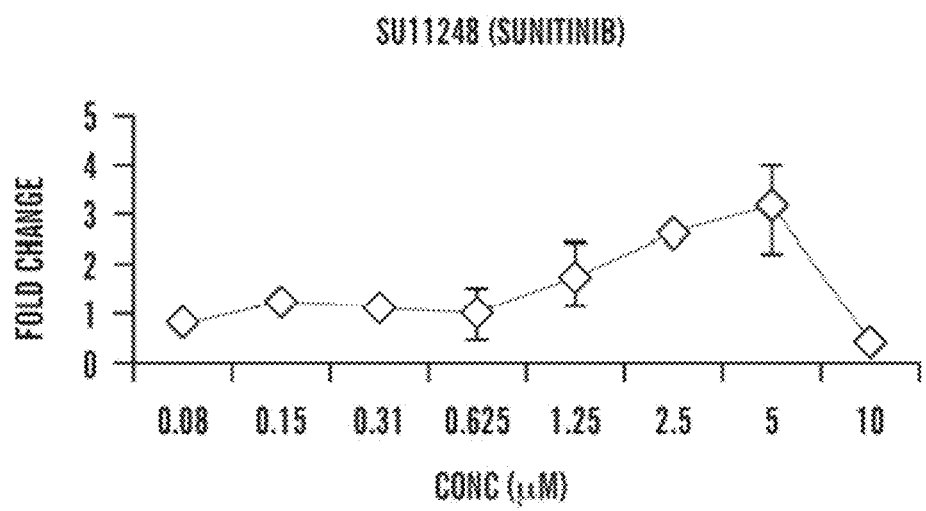
Figure 9B:
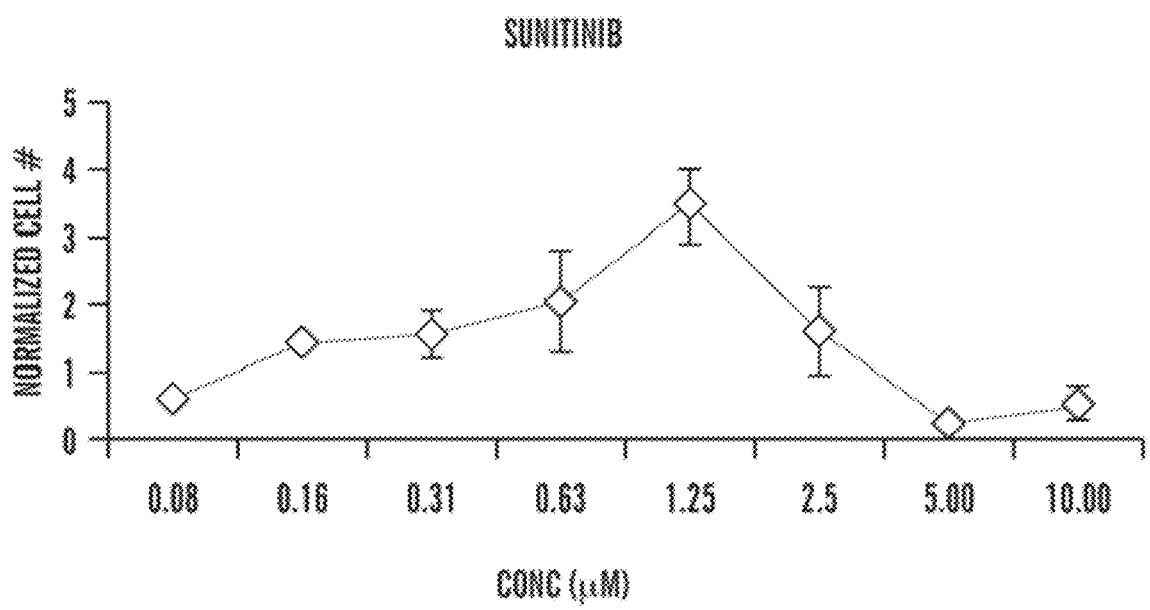
Figure 10A:
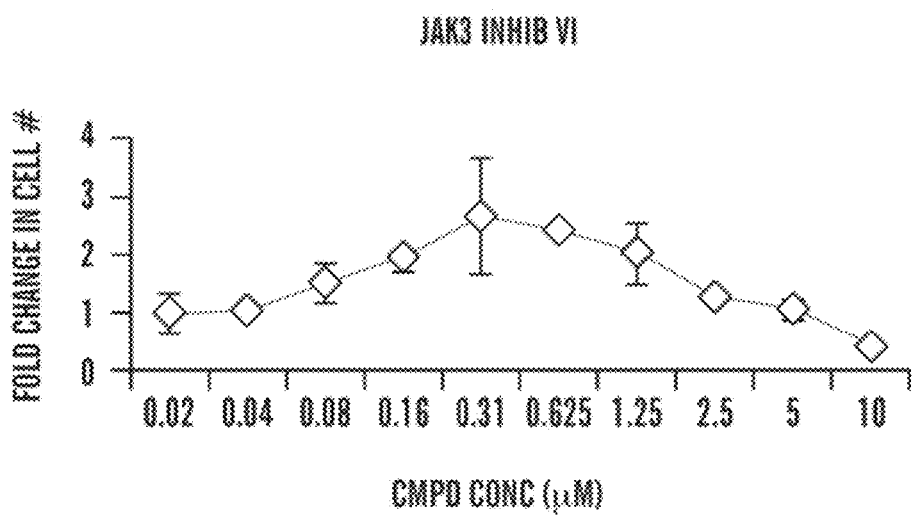
Figure 10B:
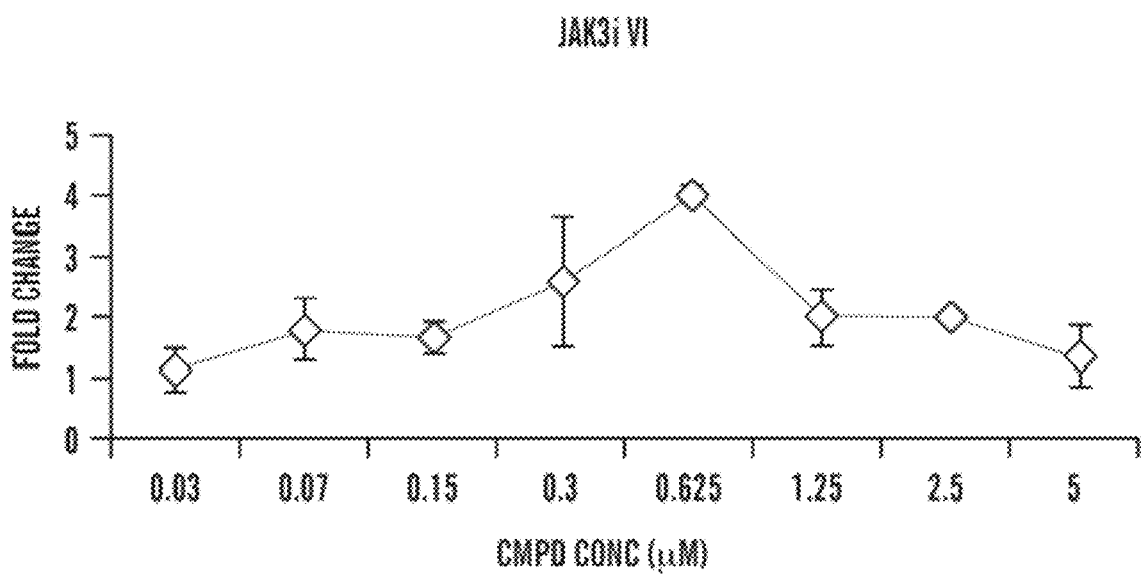
Figure 11A:
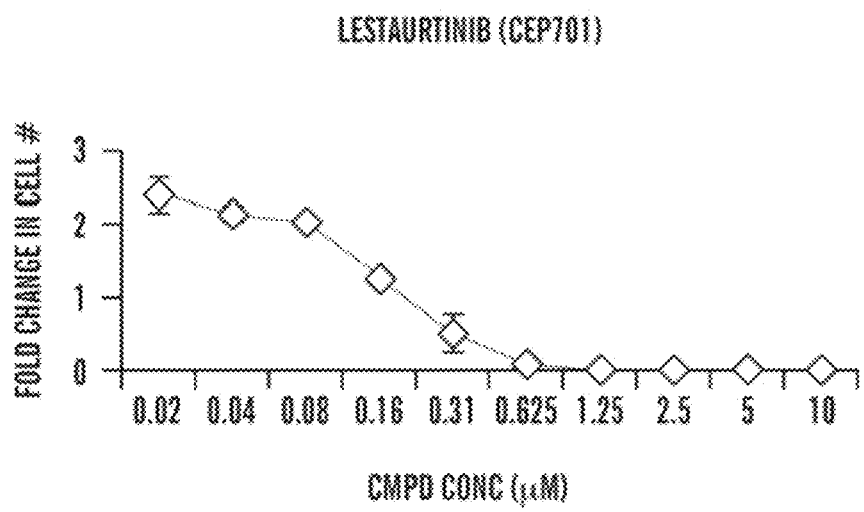
Figure 11B:
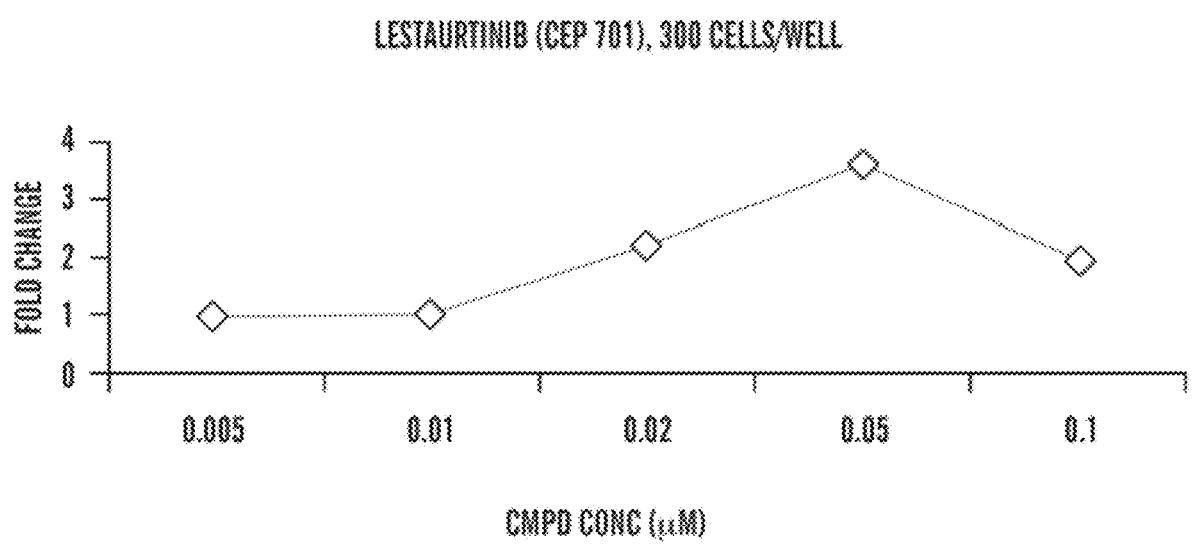
Figure 12:
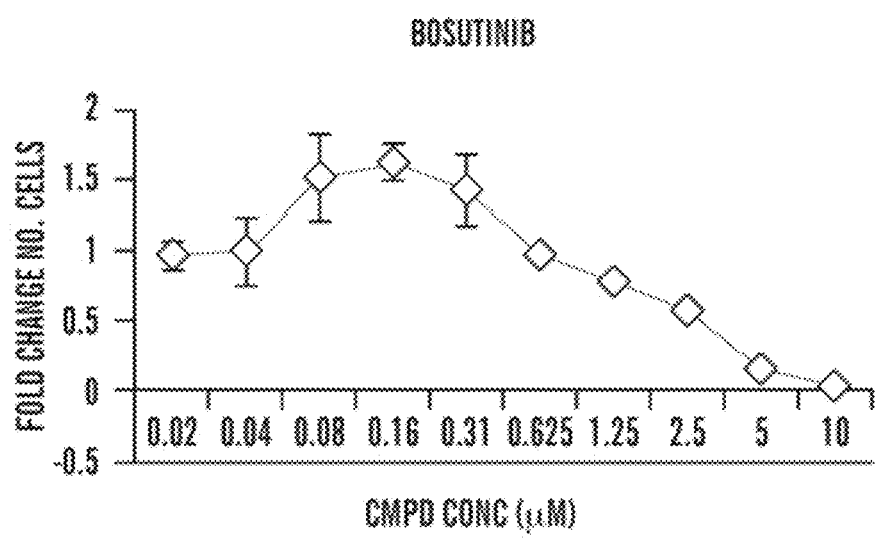

FIGS. 8A and 8B show expression of CXCR4 and Beta-1 integrin on cultured SMPs after 5 days: CEP (FIG. 8A) and DMSO (FIG. 8B).

Figure 13:
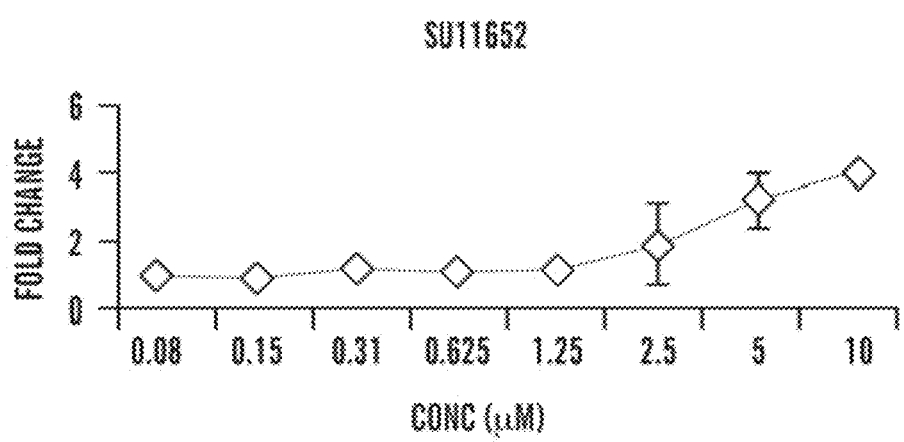
Figure 14:
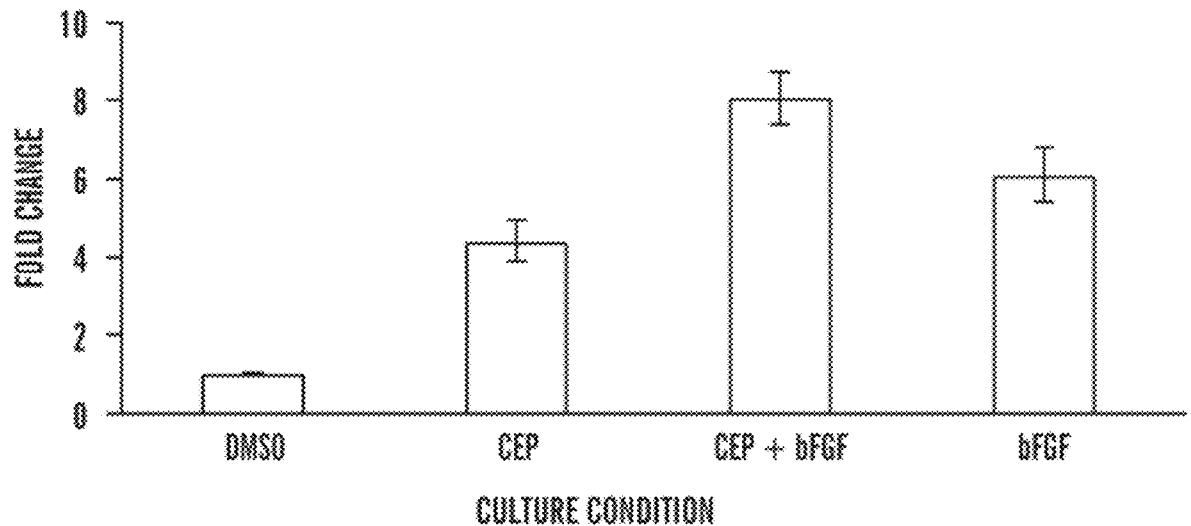

FIGS. 9A-13 show dose response curves for some exemplary hit compounds. Shown are Sunitinib (SU11248, FIGS. 9A and 9B), Jak3 inhibitor VI (FIGS. 10A and 10B), Lestaurtinib (CEP701, FIGS. 11A and 11B), Bosutinib (FIG. 12), and SU11652 (FIG. 13).

FIGS. 14-17 are bar graphs showing the synergistic effect of bFGF with CEP701 (FIGS. 14 and 15) and Jak3 inhibitor VI (FIG. 17), and Sunitinib (FIG. 17) on proliferation of satellite cells.

Figure 18:
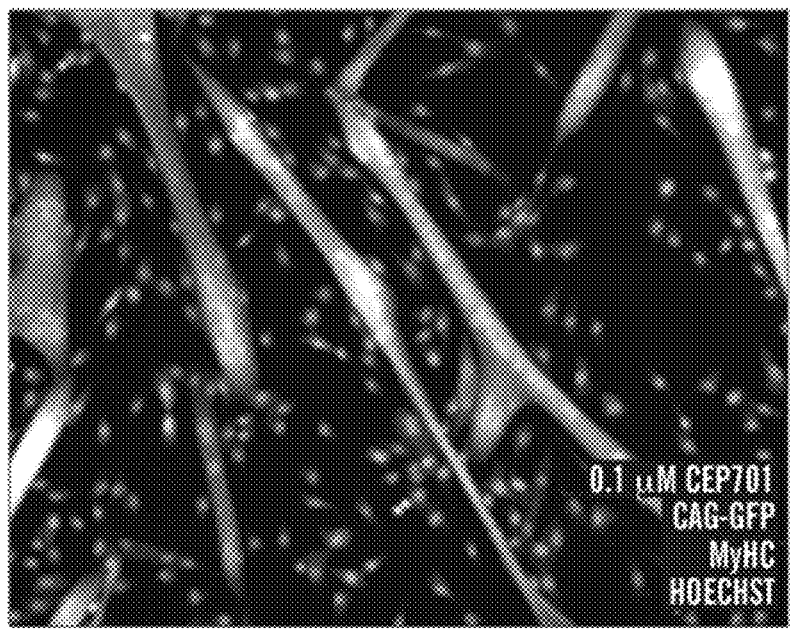
Figure 19:
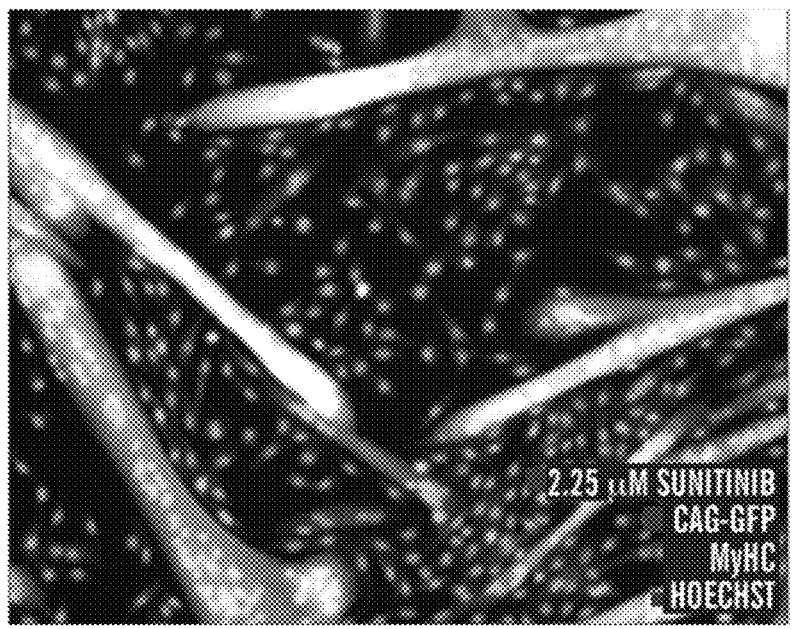
Figure 20:
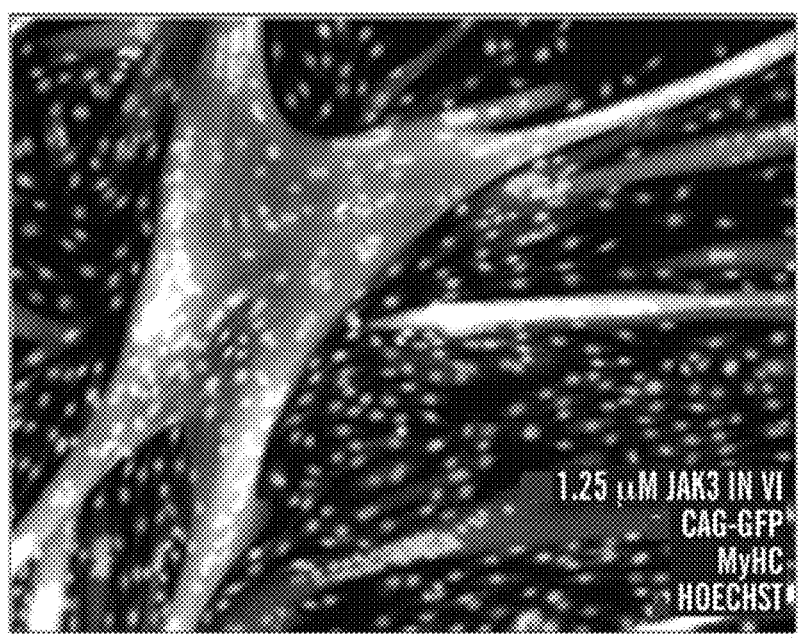

FIG. 18-20 are photographs showing differentiation of satellite cells after treatment with CEP701 (FIG. 18), Sunitinib (FIG. 19), and Jak3 inhibitor VI (FIG. 20).

Figure 21:
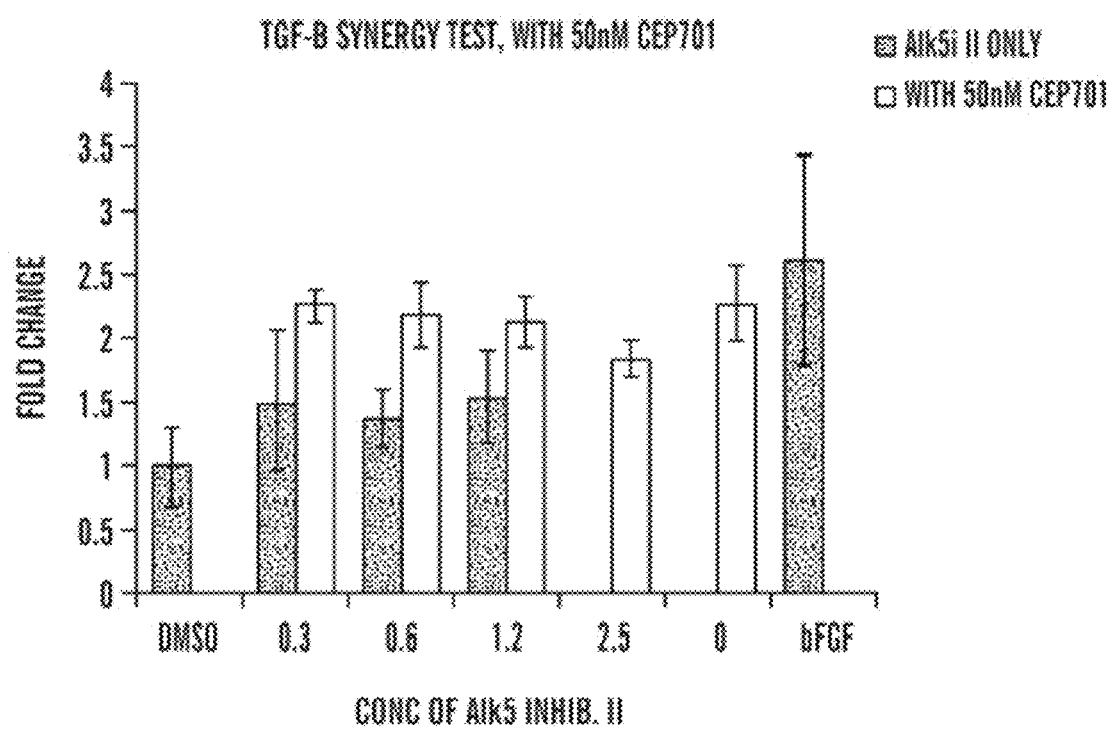

FIG. 21 is a bar graph showing the synergistic effect of CEP701 with a TGF-beta inhibitor (Alk5 inhibitor II).

Figure 22:
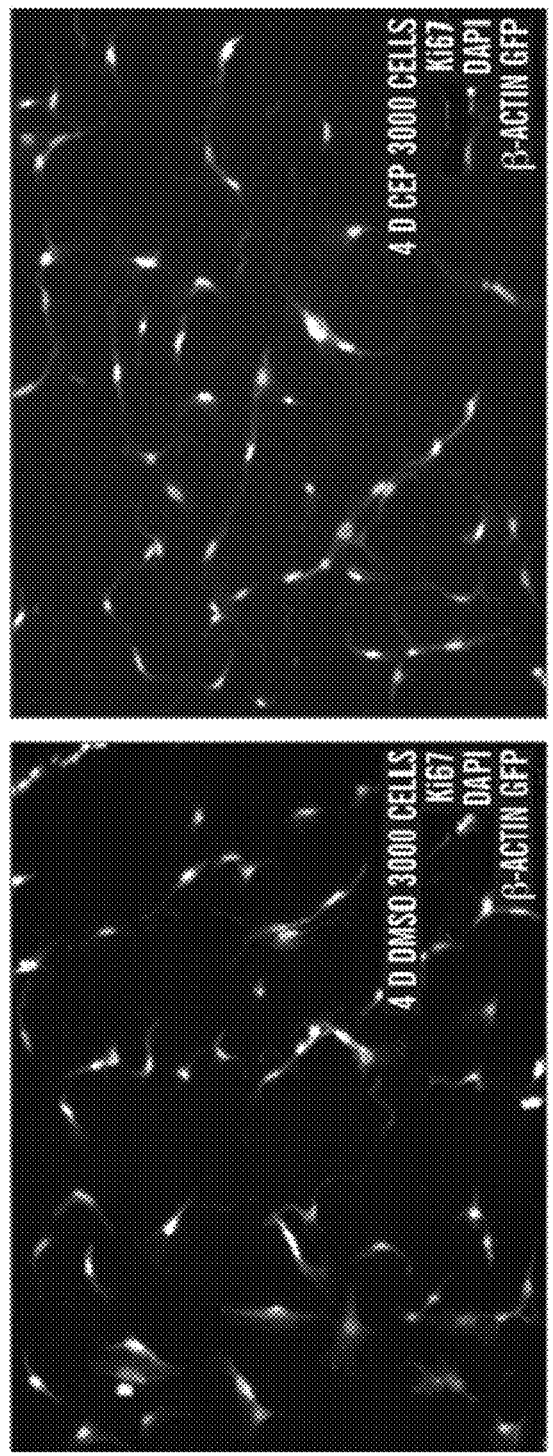

FIG. 22 shows specificity of CEP701 for proliferating satellite cells. Left panel: CEP701; right panel: DMSO.

Figure 23:
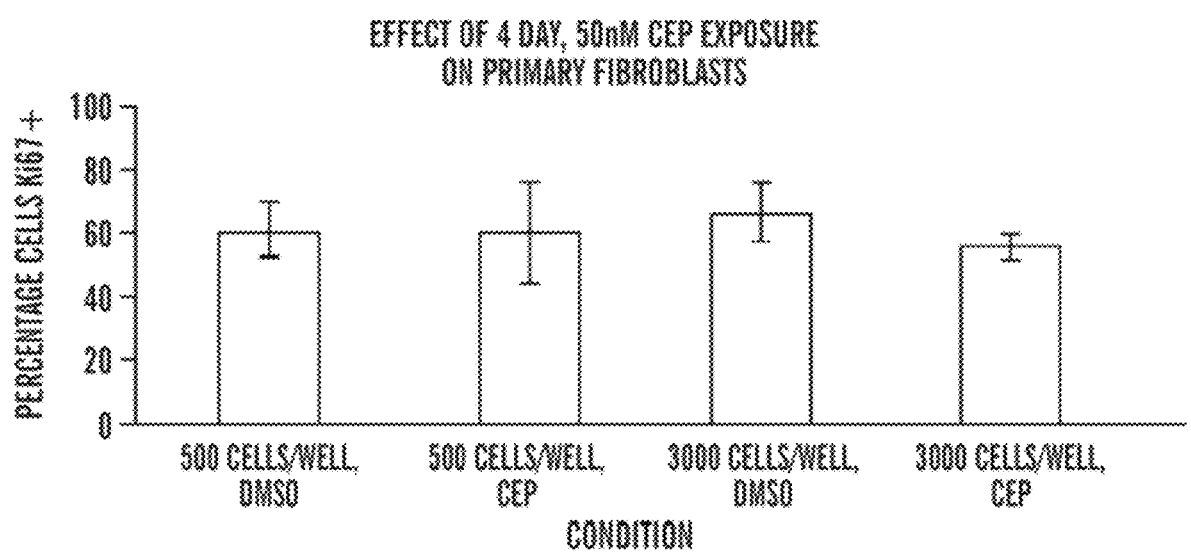

FIG. 23 is bar graph showing CEP701 has no effect on primary fibroblasts

Figure 24:
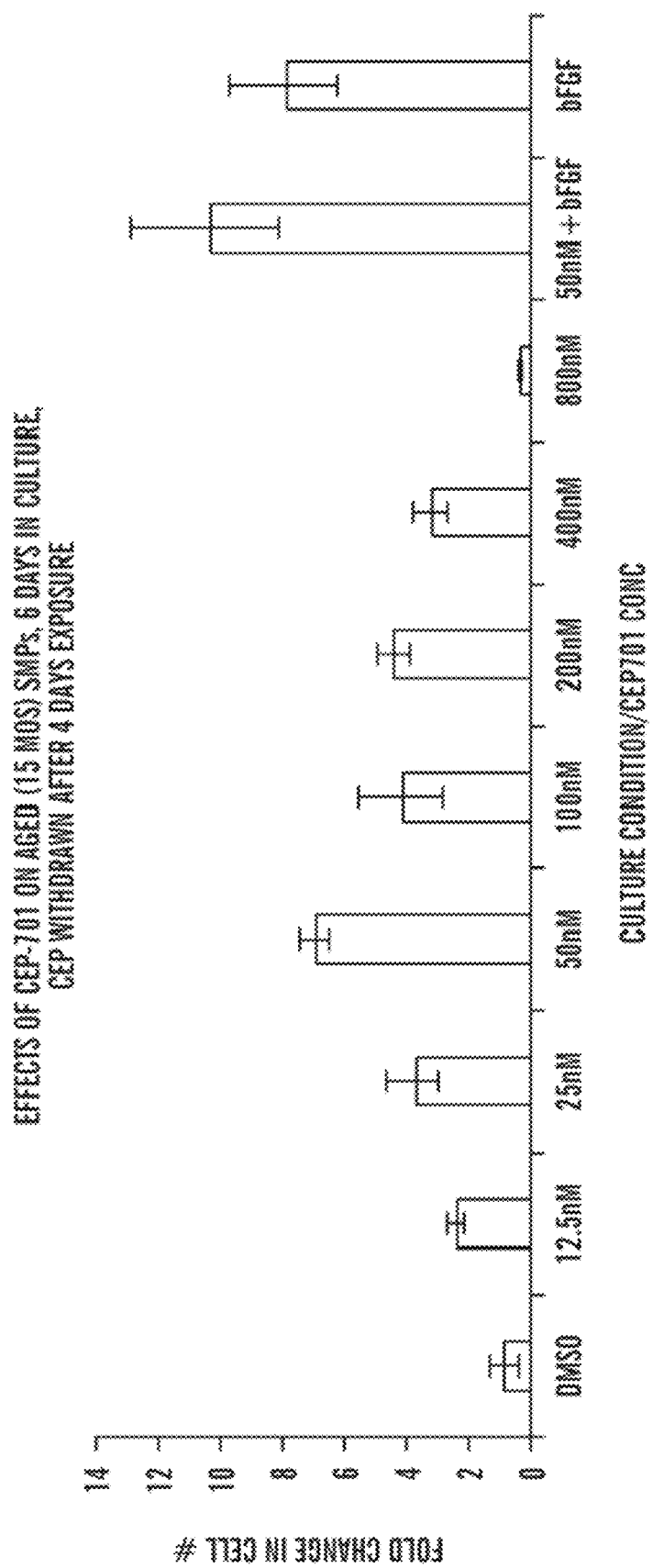
Figure 25:
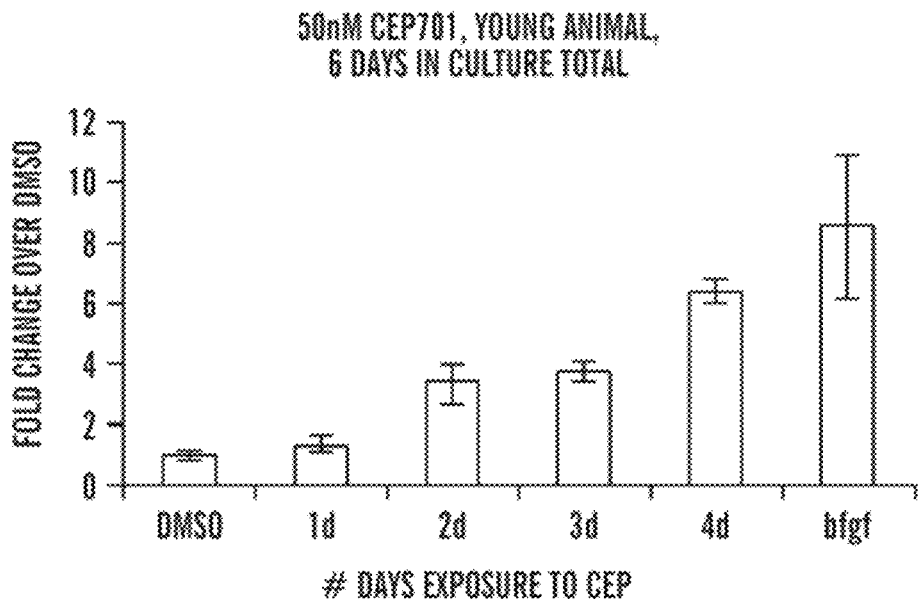

FIGS. 24 and 25 are bar graphs showing CEP701 is effective in both the aged (FIG. 24) and young (FIG. 25) tissue.

Figure 26:
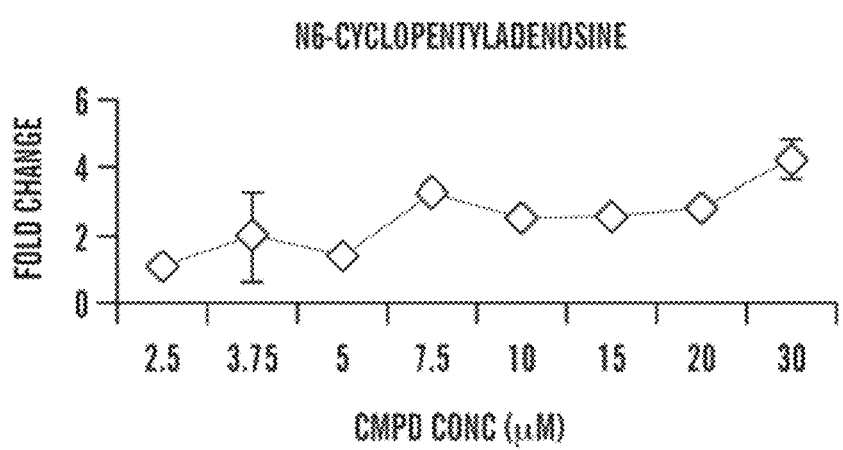
Figure 27:
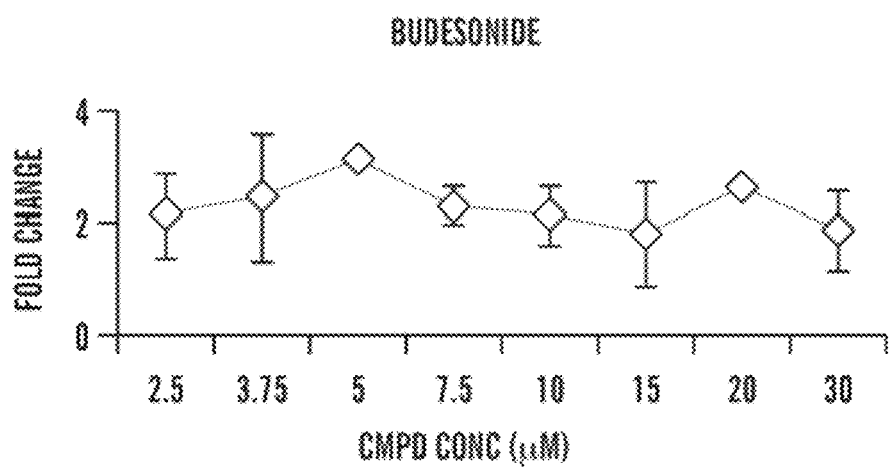

FIGS. 26 and 27 are line graph showing dose response curves for N6-cyclopentyladenosine (FIG. 26) and Budesonide (FIG. 27).

Figure 28:
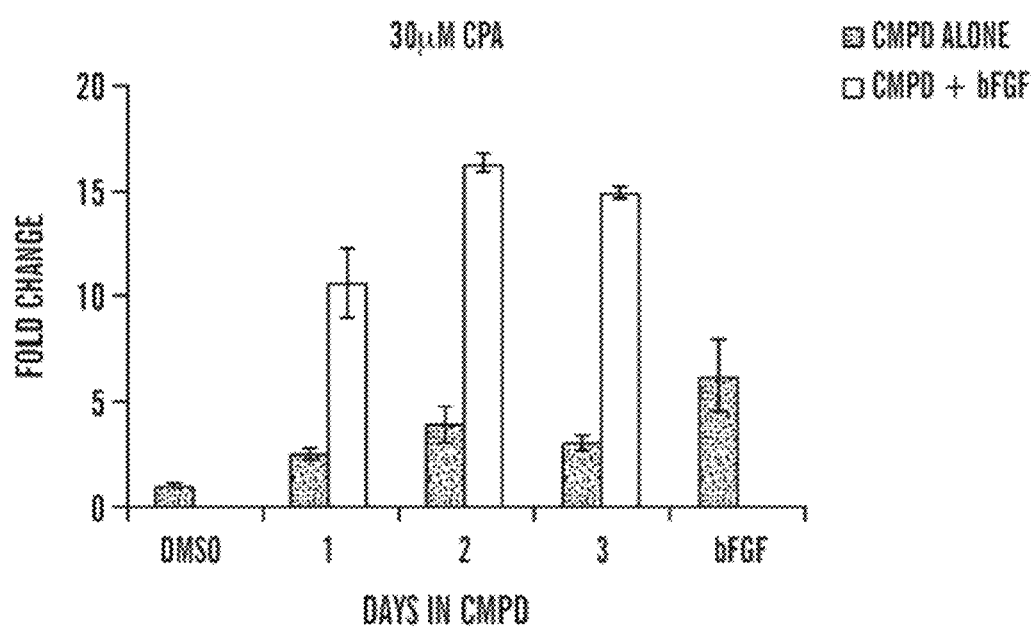
Figure 29:
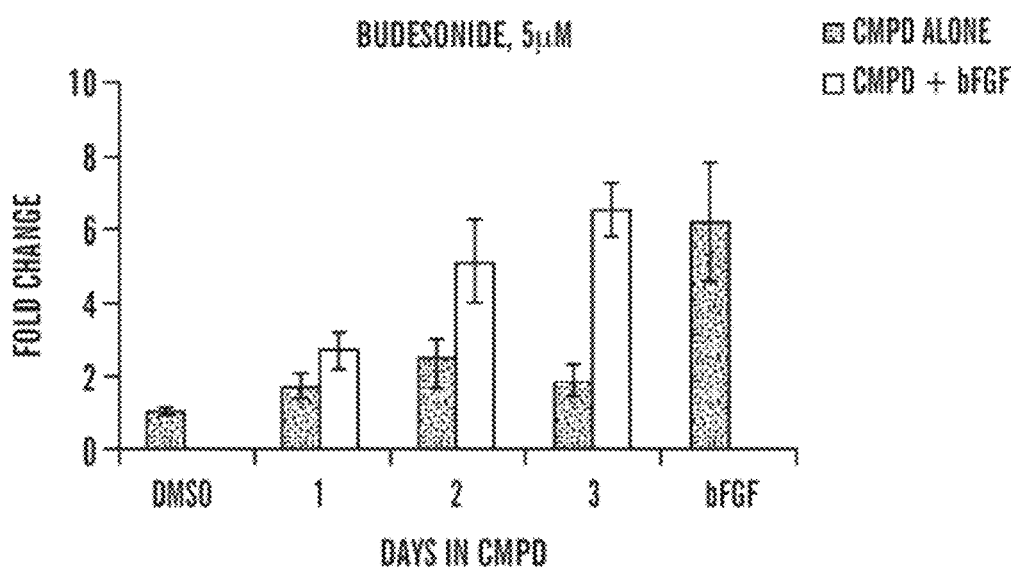

FIGS. 28 and 29 are bar graph showing the synergistic effect of bFGF with N6-cyclopentyladenosine (FIG. 28) and Budesonide (FIG. 29).

Figure 30:
Figure 31:
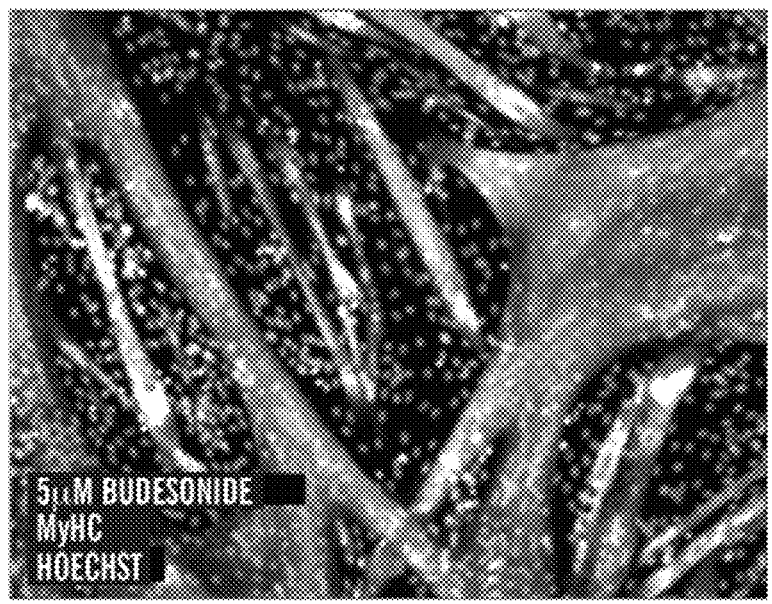

FIGS. 30 and 31 are photographs showing differentiation of satellite cells after treatment with N6-Cyclopentyladenosine (FIG. 30) and Budesonide (FIG. 31).

Figure 32:
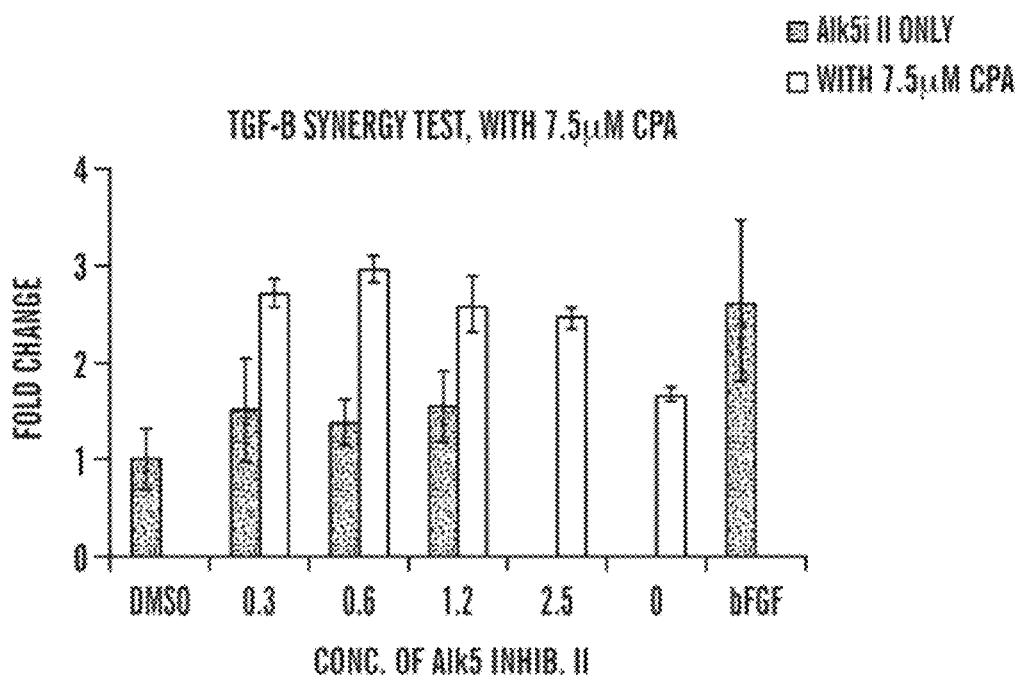

FIG. 32 is a bar graph showing the synergistic effect of N6-Cyclopentyladenosine with a TGF-beta inhibitor (Alk5 inhibitor II).

Figure 33:
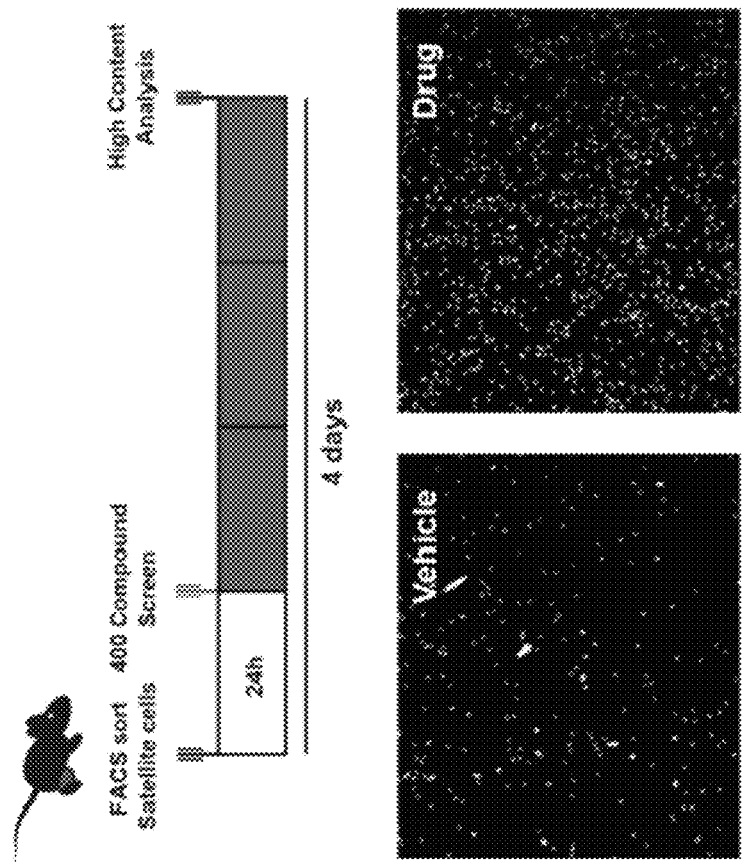

FIG. 33 illustrates the screening assay performed to identify those primary and secondary compounds that were shown to increase satellite cell proliferation in vitro.

Figure 34:
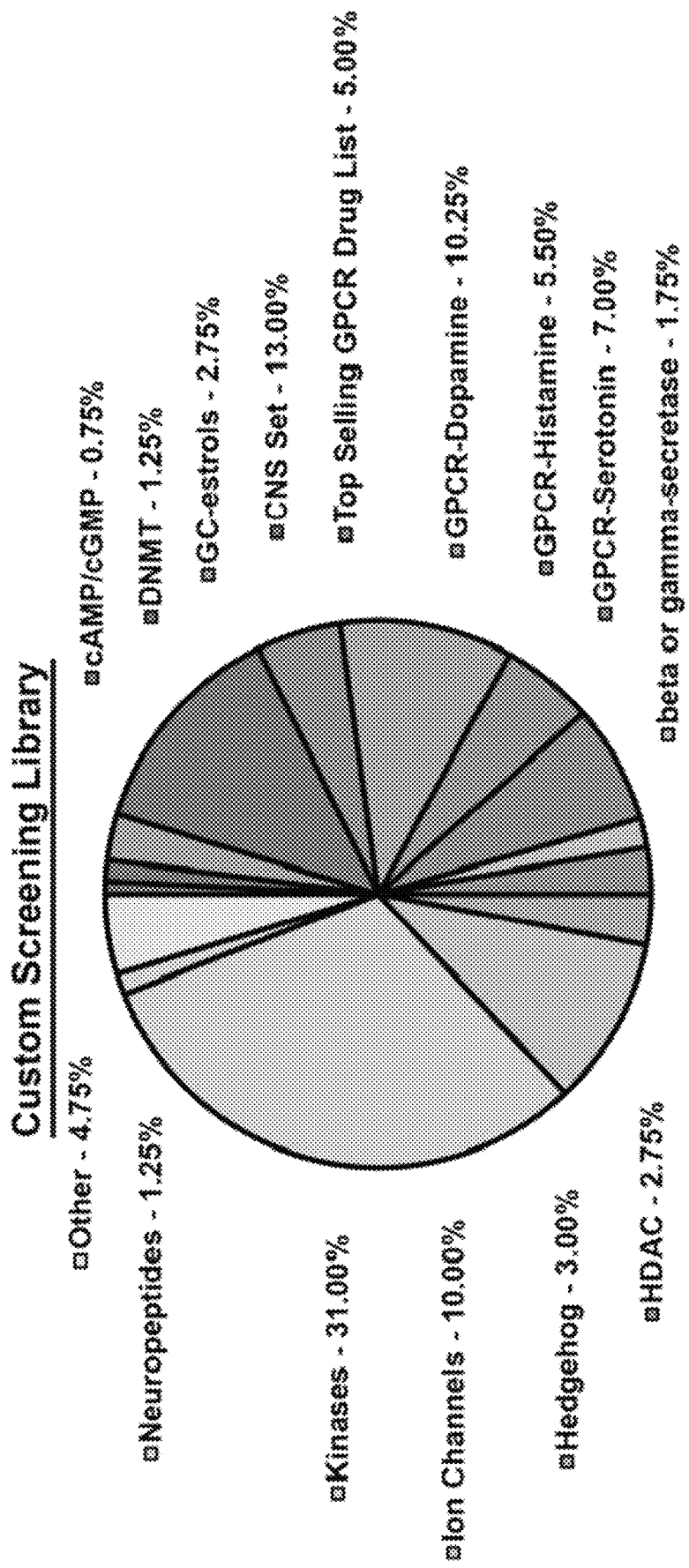

FIG. 34 depicts the customer screening library used by the present inventors to screen a set of approximately 400 compounds to identify those compounds that increase satellite cell proliferation.

Figure 35:
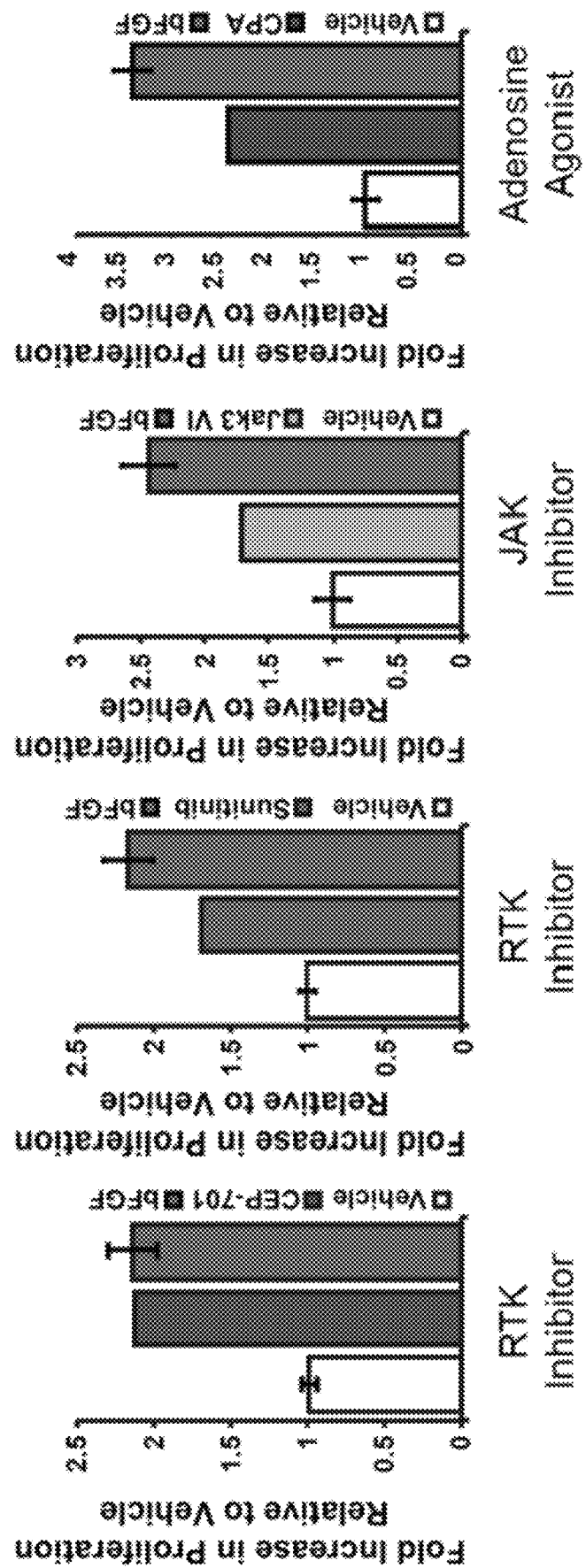

FIG. 35 illustrates the results of assays performed and that demonstrate that lestaurtinib (CEP701), Sunitinib (SU11248), JAK3 inhibitor VI, and N6-cyclopentyladenosine (CPA) were found to increase in vitro satellite cell proliferation. Lestaurtinib (CEP701) was identified as a top hit, was effective at nanomolar doses and had target overlap with several other hit compounds.

Figure 36:
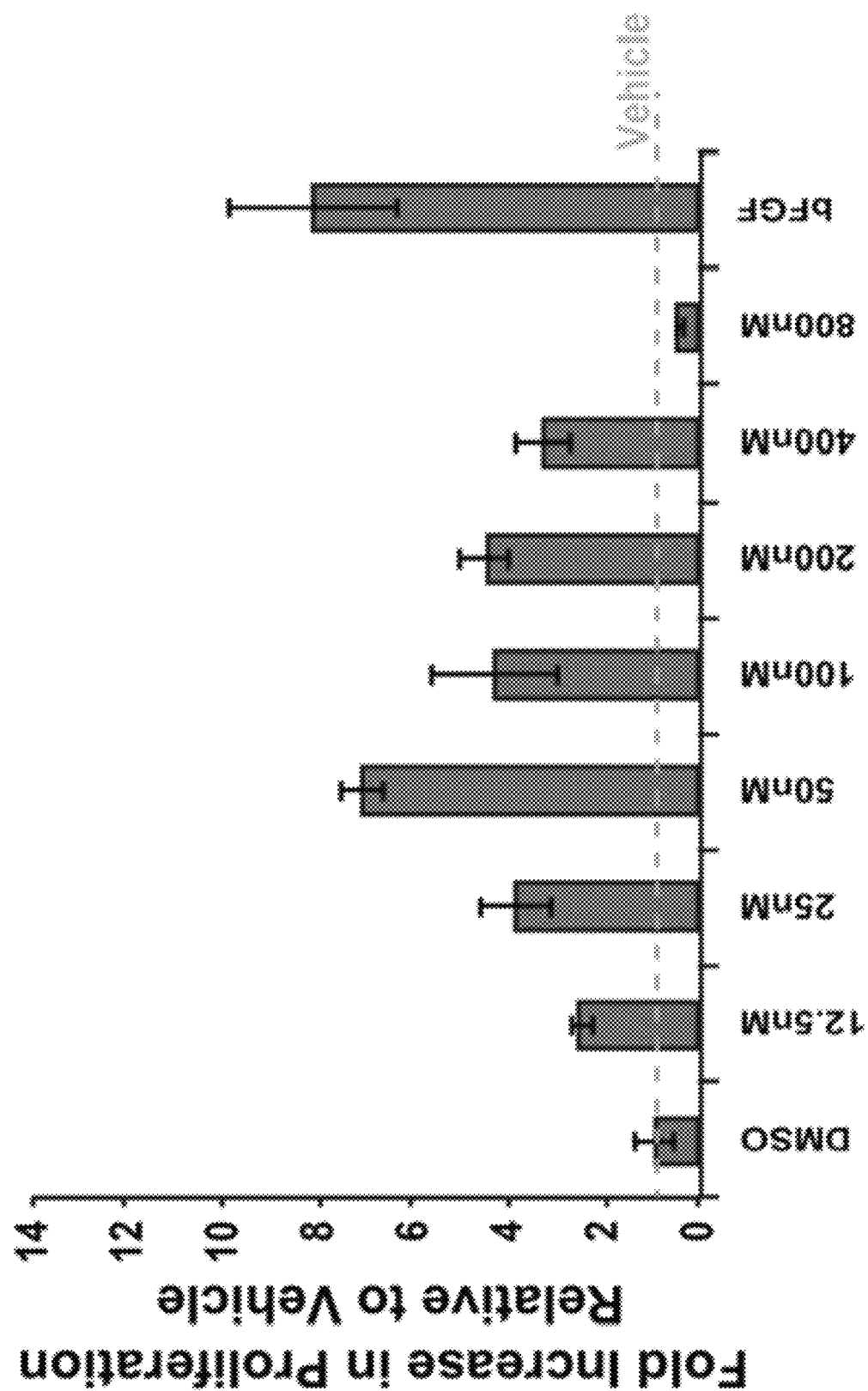

FIG. 36 illustrates the results of an assay performed and that evidence that lestaurtinib (CEP701) increased proliferation of aged satellite cells in vitro.

Figures 37A, 37B:
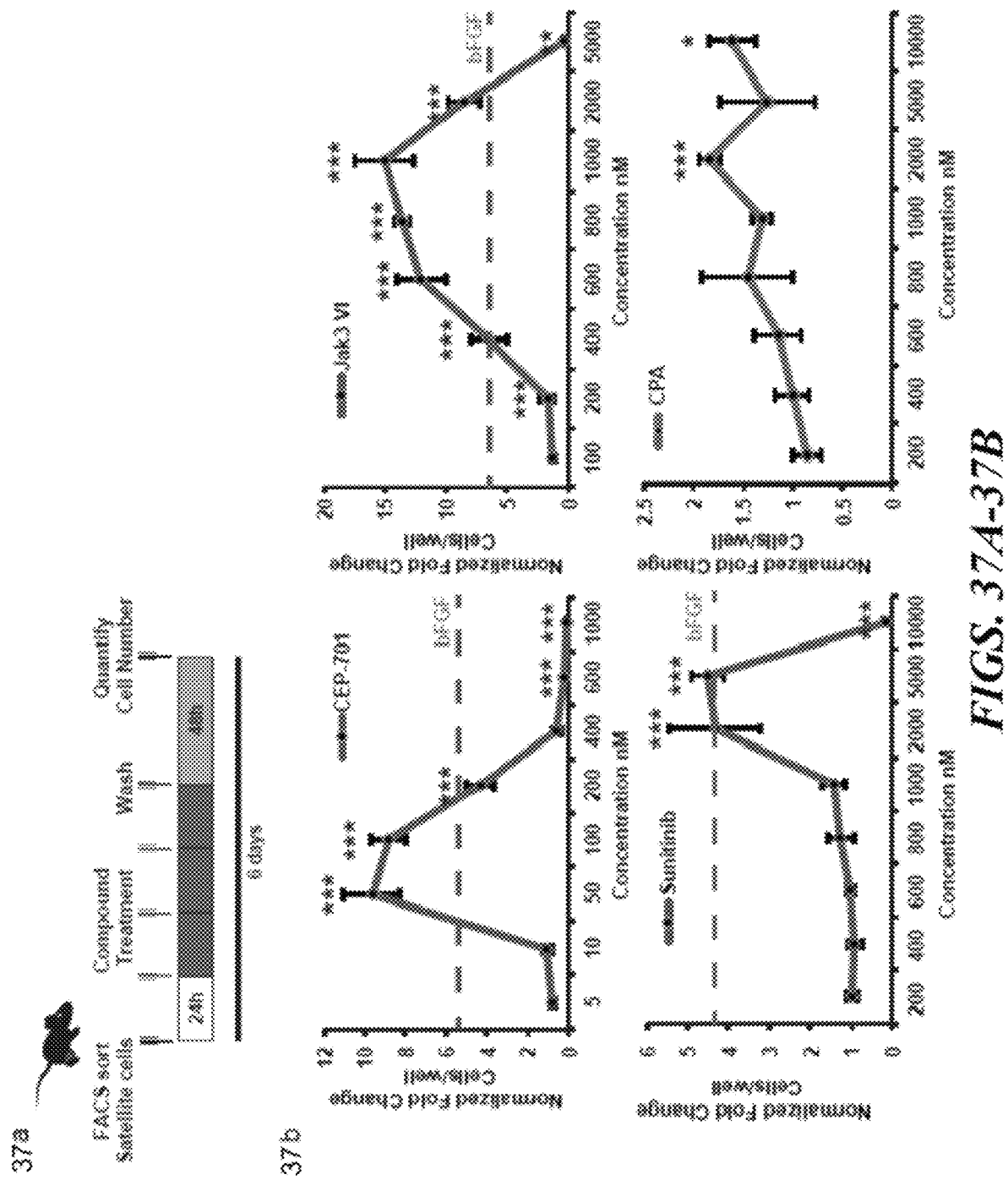

FIGS. 37A-37B illustrate a dose response assay (FIG. 37A) and the response curves for each of lestaurtinib (CEP701), sunitinib (SU11248), JAK3 inhibitor VI, and N6-cyclopentyladenosine (CPA) (FIG. 37B).

Figure 38:
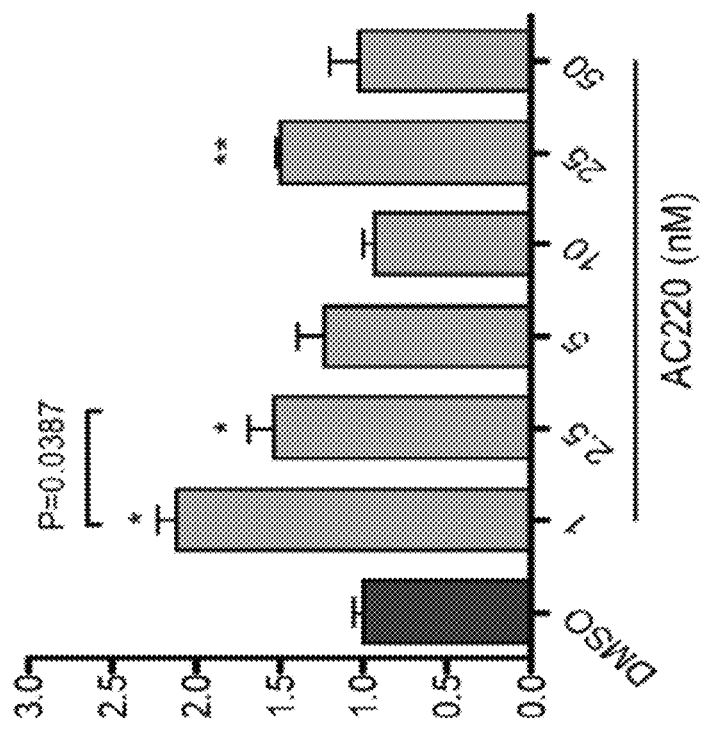
Figure 38:
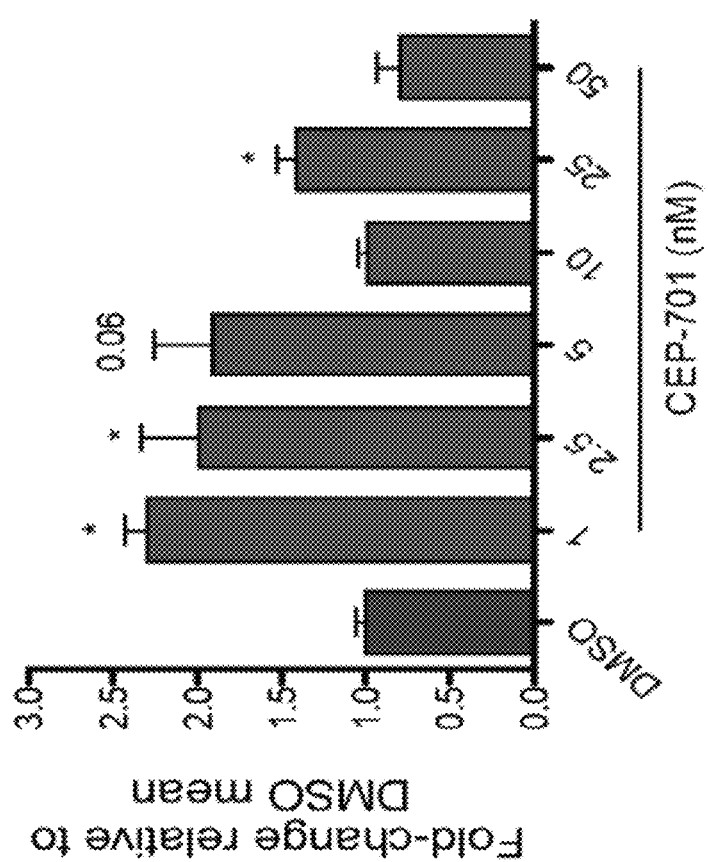

FIG. 38 demonstrates that both CEP-701 and AC220 increased human satellite cells by more than 2-fold at a concentration of 1 nM relative to control (DMSO).

Figure 39:
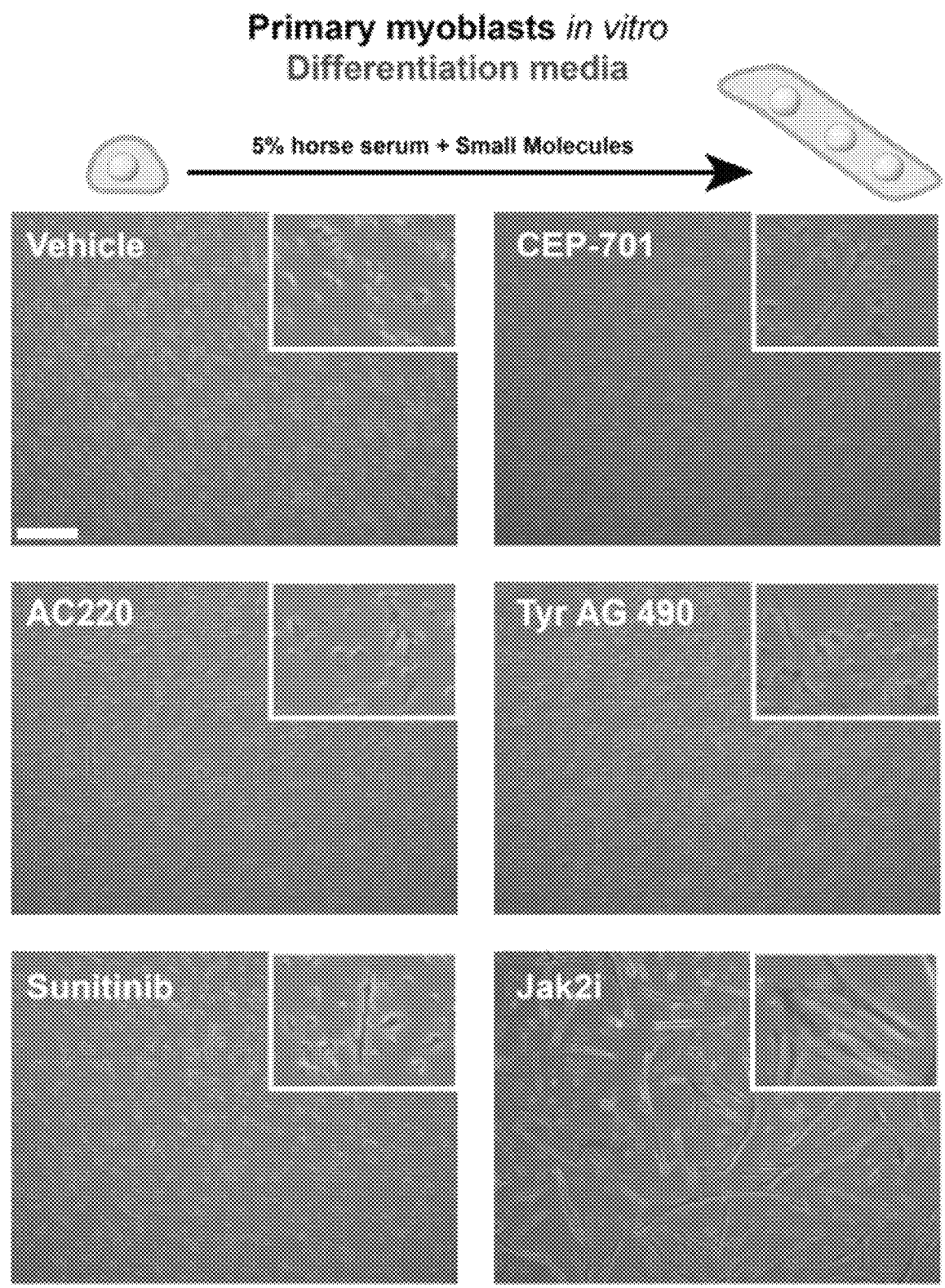

FIG. 39 presents the results of an assay performed and confirms that those compounds identified as hits (e.g., CEP701, SU11248, JAK3 inhibitor VI, CPA and Tyr AG490) drive myoblast differentiation.

Figure 40:
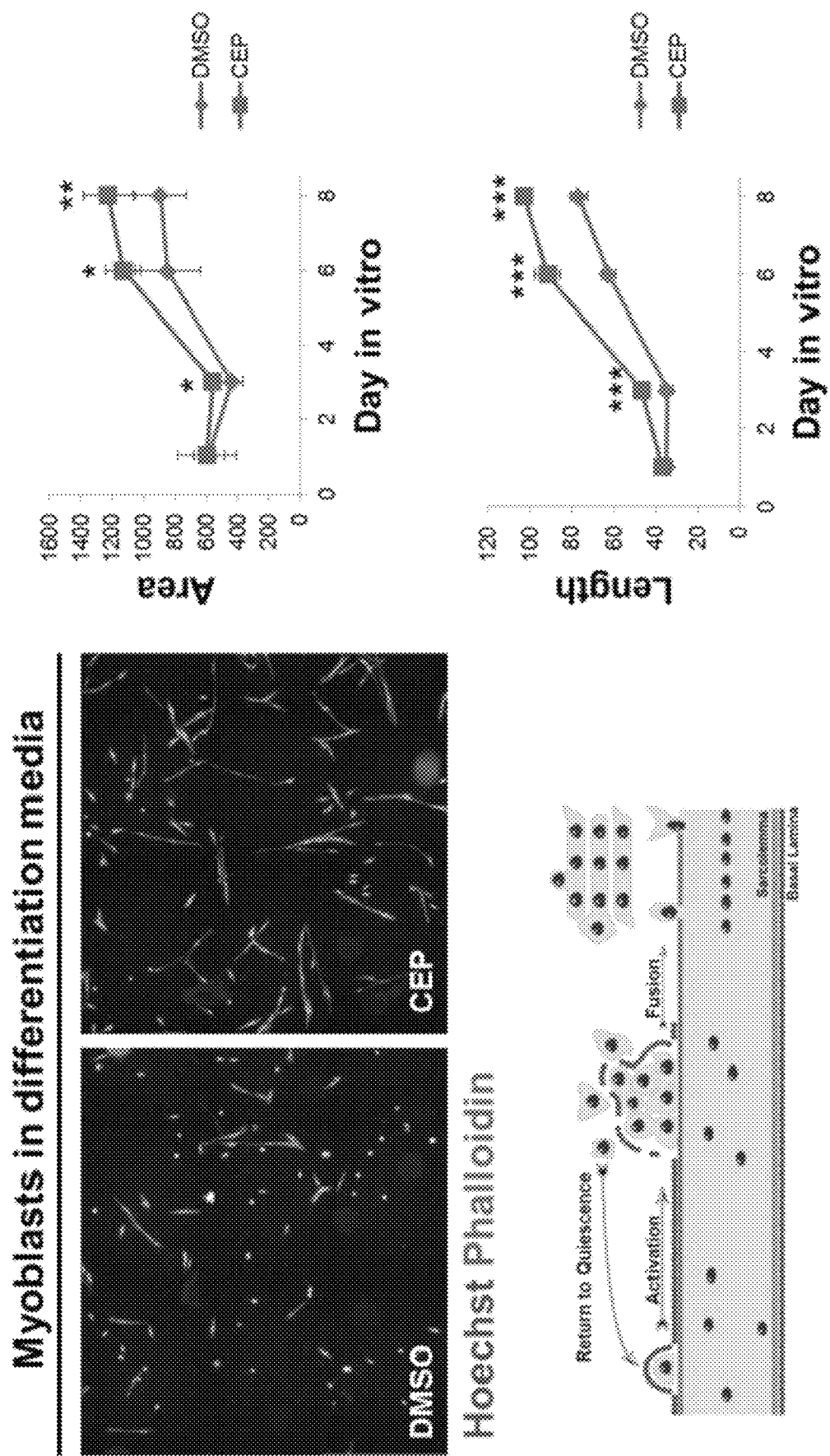

FIG. 40 demonstrates that CEP701 enhances myoblast differentiation in differentiation media relative to the DMSO control, as evidenced by the observed increase in both myoblast area and length.

Figures 41A, 41B:
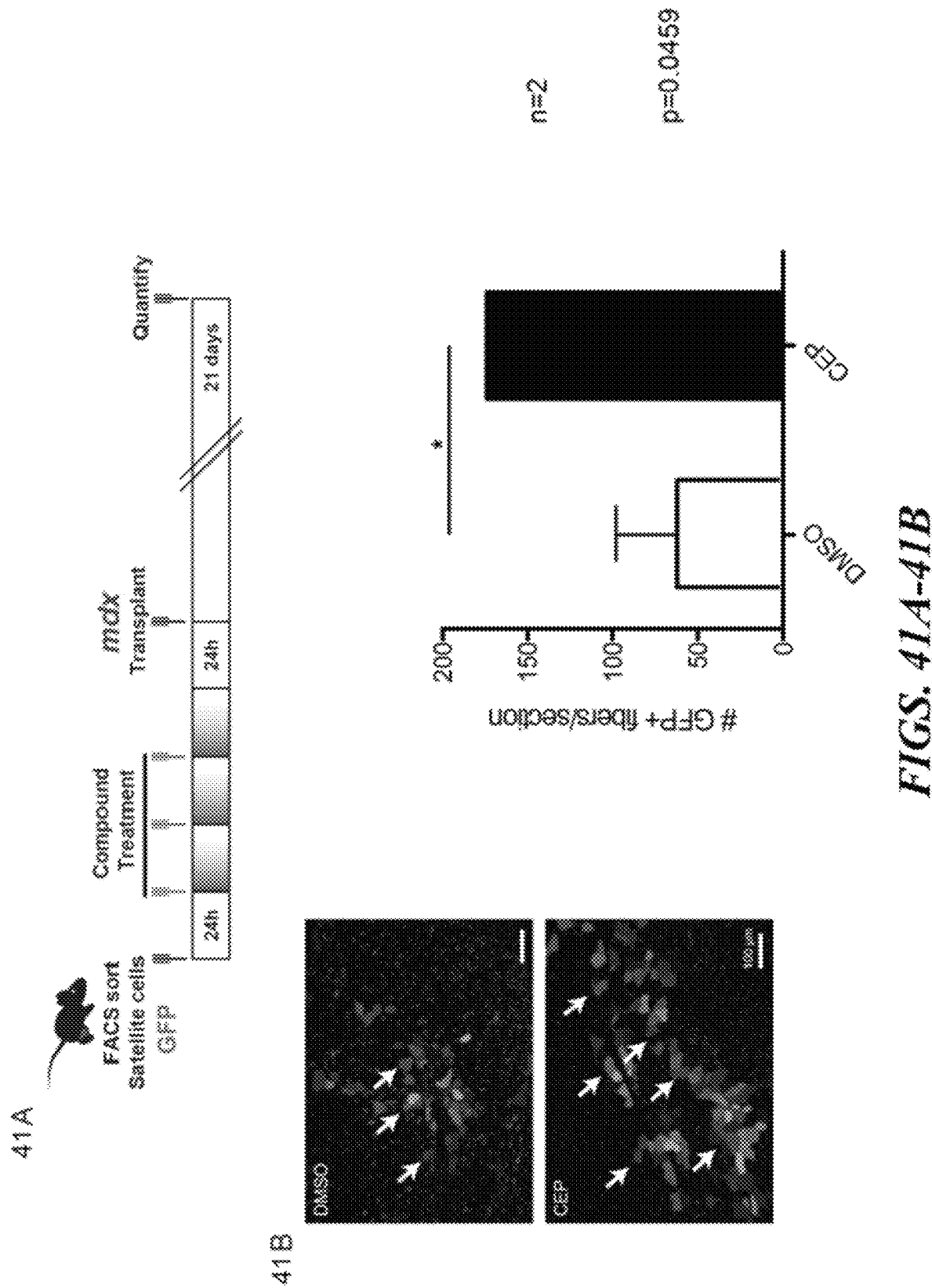

FIGS. 41A-41B depict an experimental protocol (FIG. 41A) and the results of that experiment (FIG. 41B) and which illustrates that CEP701 treatment of cells resulted in an increased number of GFP+ fibers per section, relative to control (DMSO).

Figures 42A, 42B:
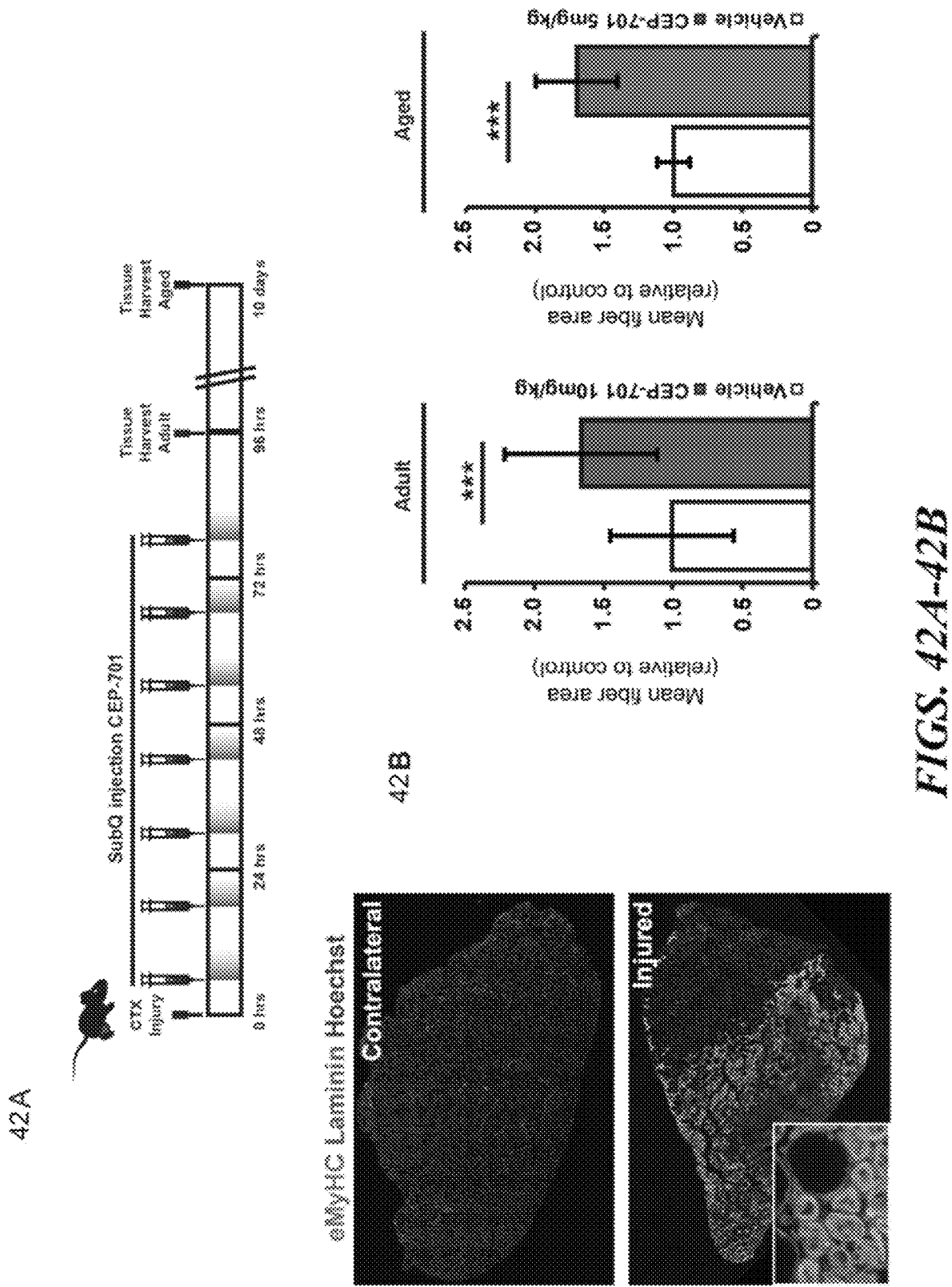
Figure 42C:
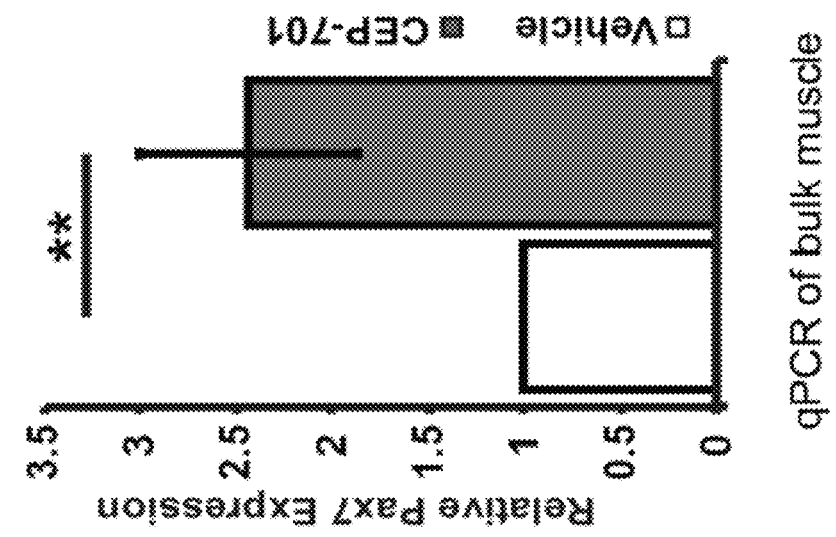
Figure 42D:
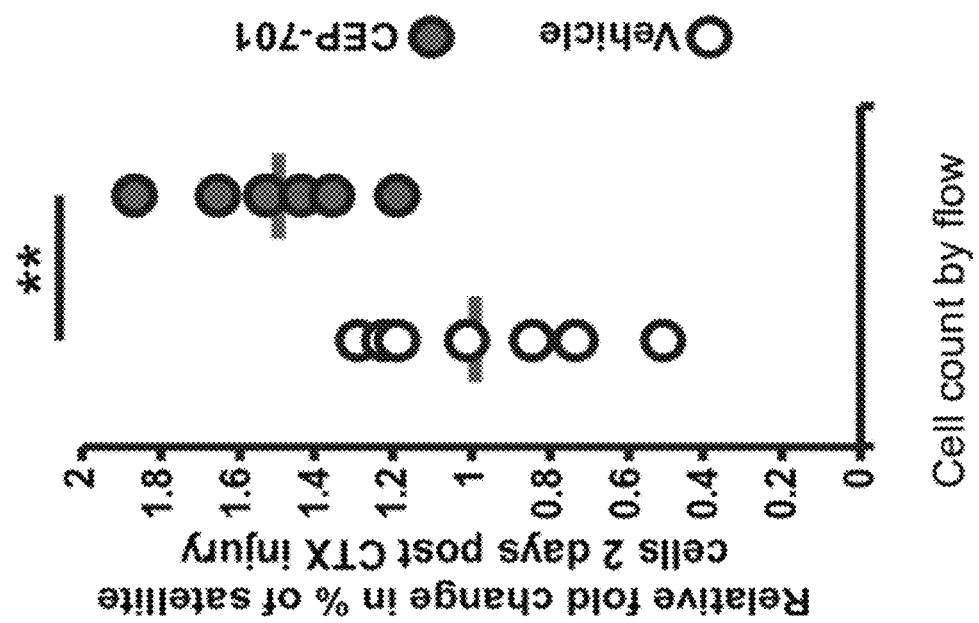

FIGS. 42A-42D depict an experimental protocol (FIG. 42A) and the corresponding results observed. As illustrated in FIGS. 42B-42D, treatment with CEP701 increased both regenerating fiber size and satellite cell number in vivo in both adult and aged mice.

Figures 43A, 43B:
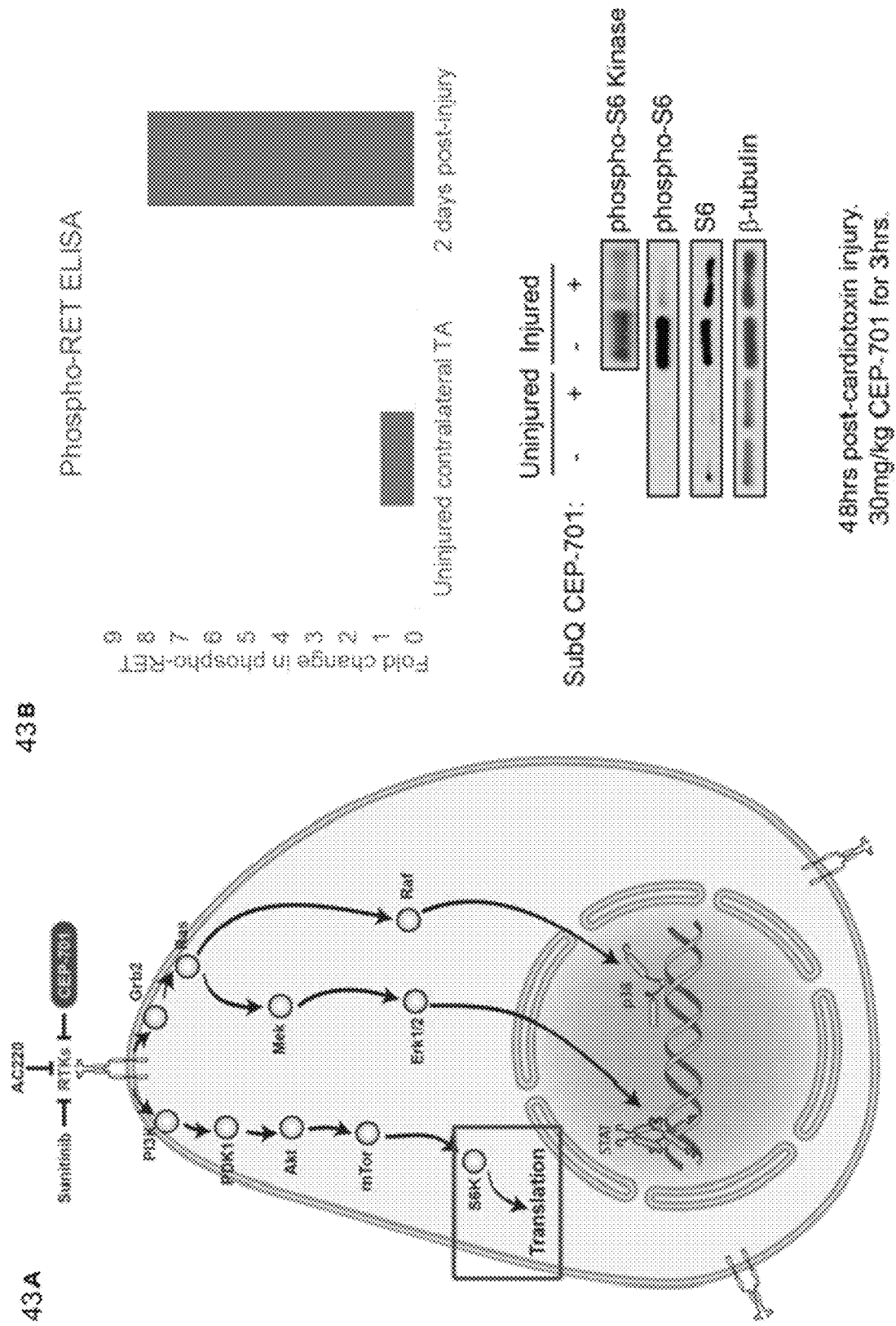

FIGS. 43A-43B illustrate the affect that the identified compounds have on RTKs (FIG. 43A) and, as illustrated in FIG. 43B, compares the fold change in phospho-RET in both uninjured contralateral tibialis anterior (TA) muscle to that observed 2 days post-cardiotoxin injury. As illustrated in FIG. 43B, 2 days post-cardiotoxin injury, an approximately 8-fold increase in phospho-RET was observed by ELISA relative to uninjured contralateral TA muscle.

Figure 44A:
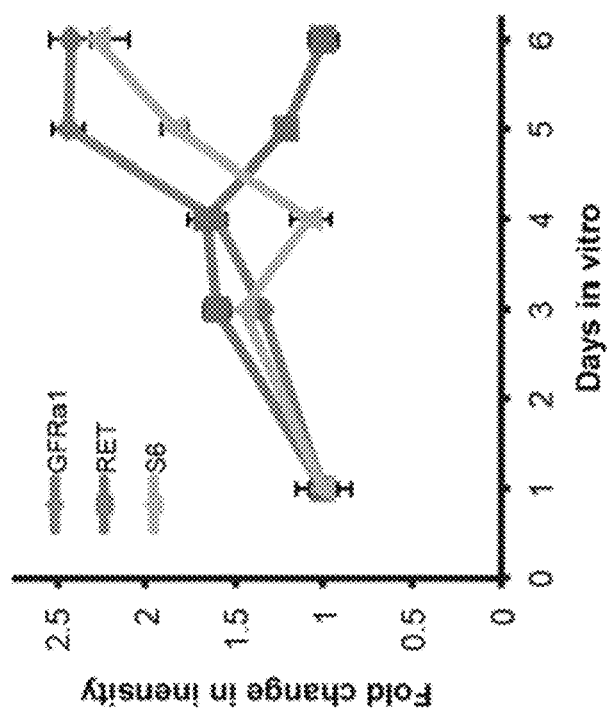
Figure 44B:
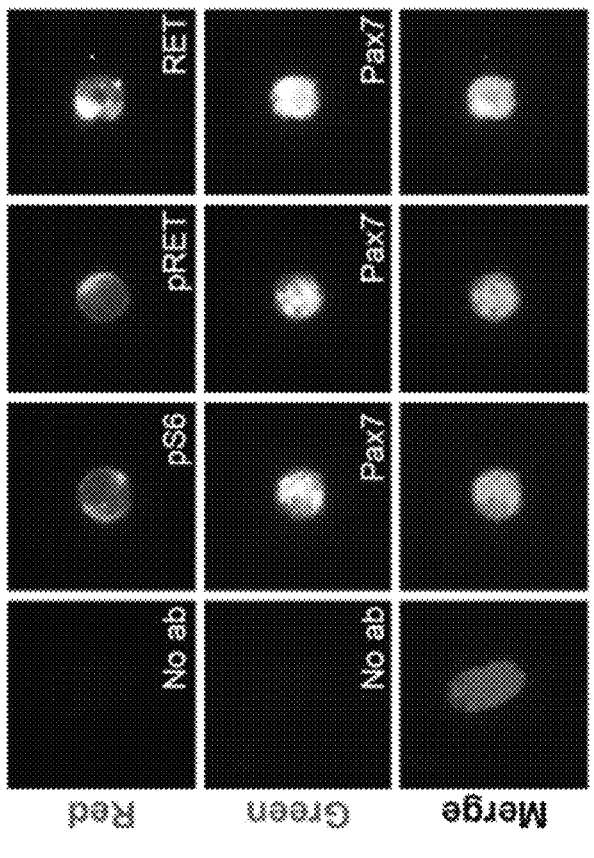
Figure 45A:
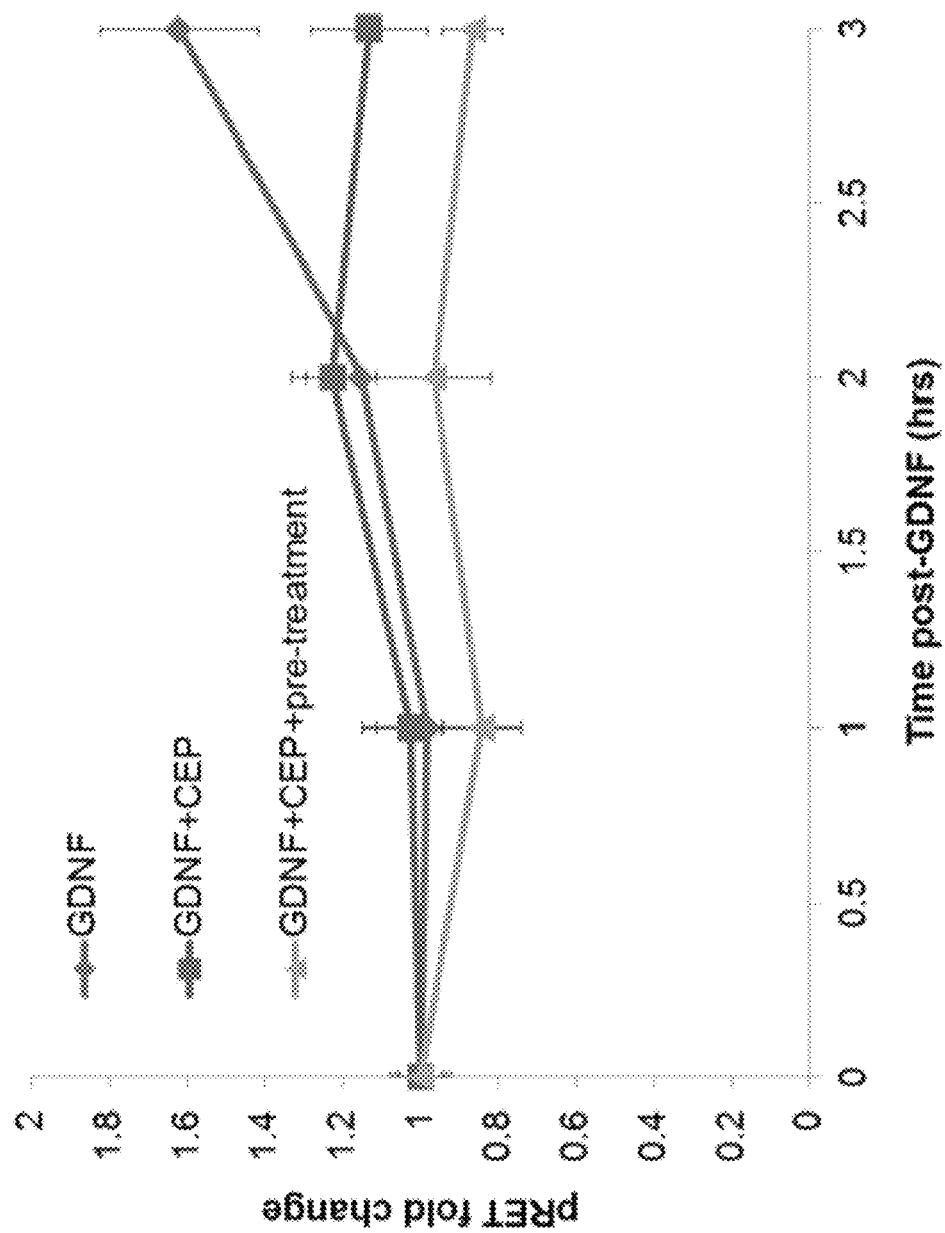
Figures 45B, 45C, 45D:
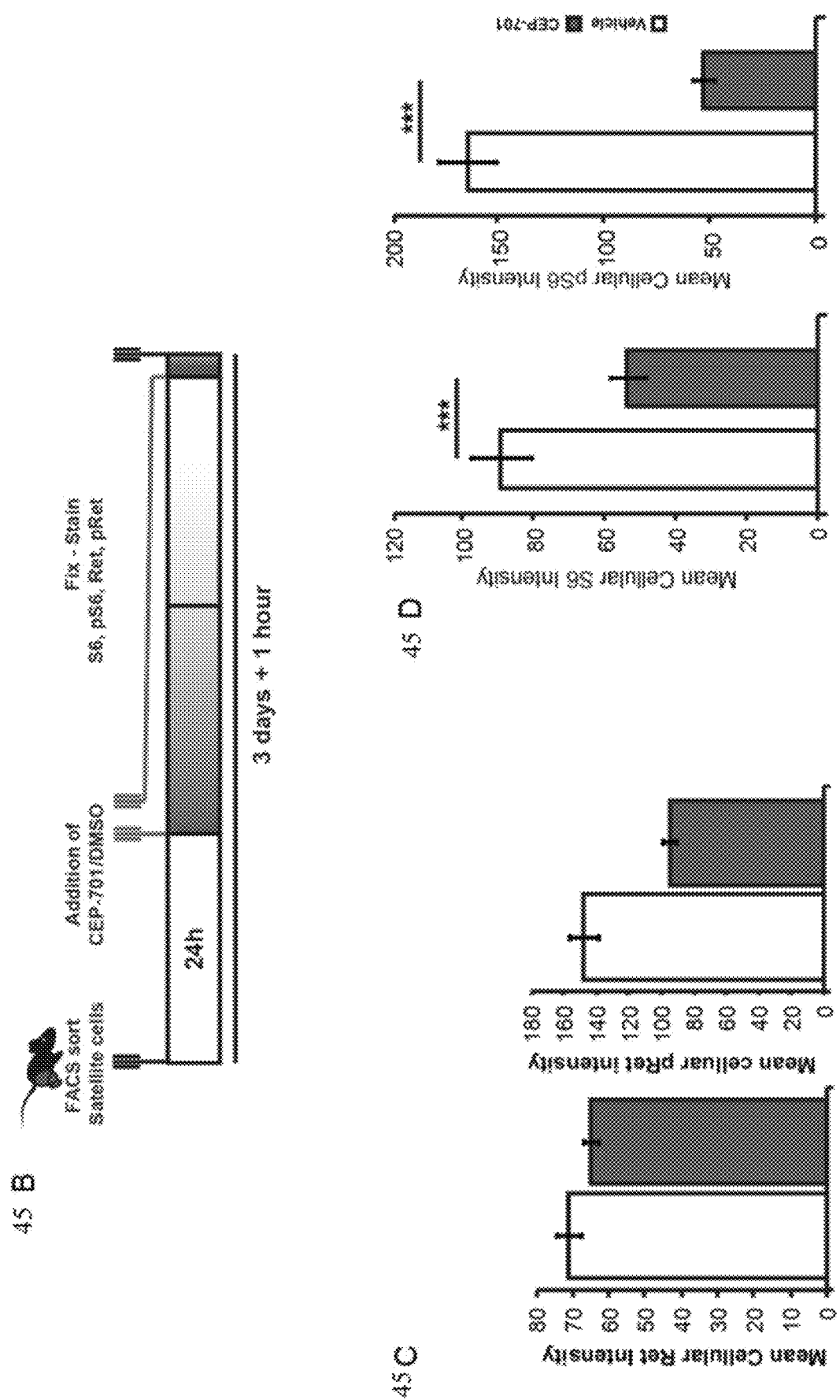

FIGS. 44A-44B illustrate that satellite cells express RET in vitro.

FIGS. 45A-45D illustrate that CEP701 treatment inhibits RET phosphorylation in vitro.

Figure 46:
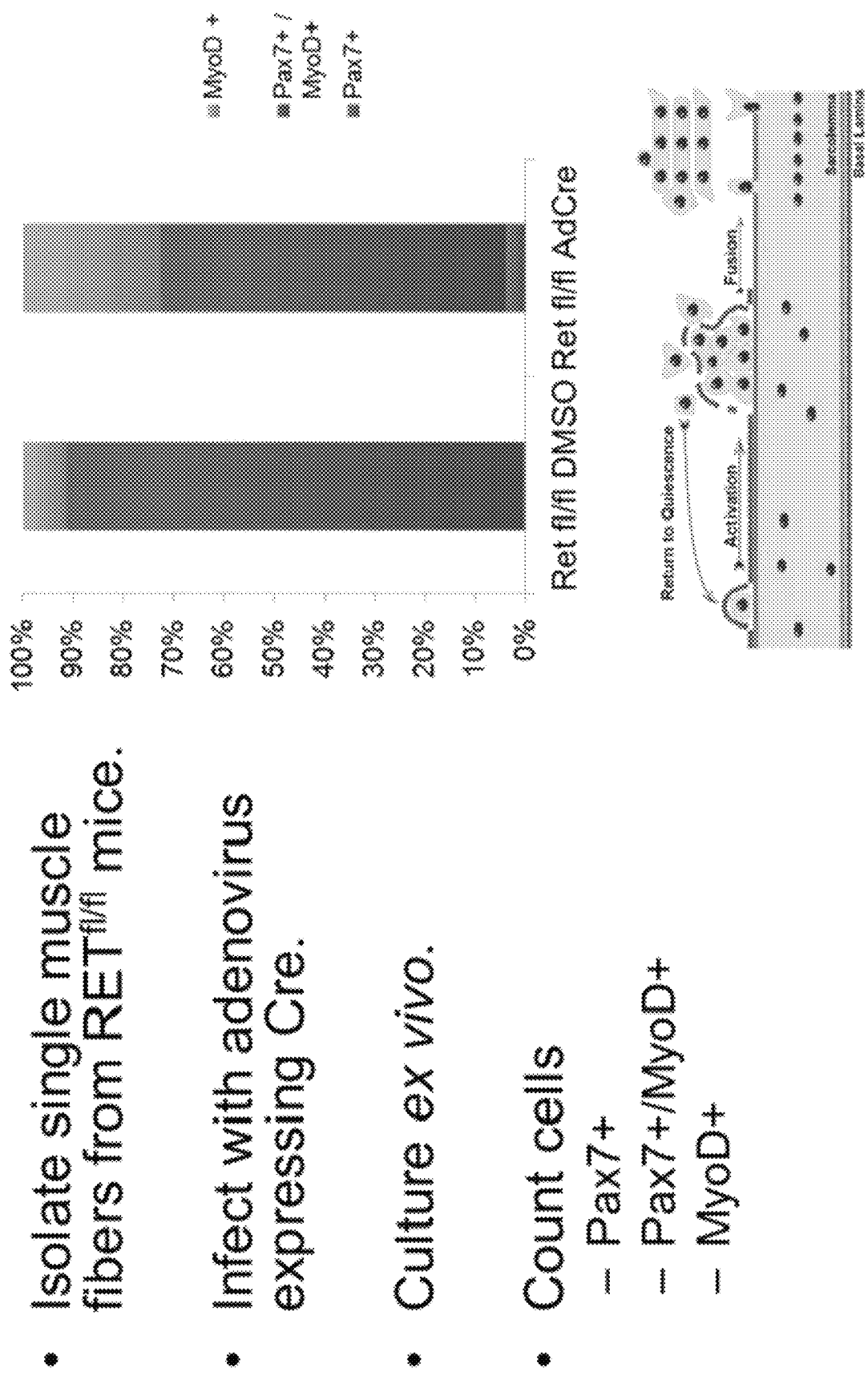

FIG. 46 shows the results of a study evaluating the effects of the in vitro deletion of RET.

Figure 47:
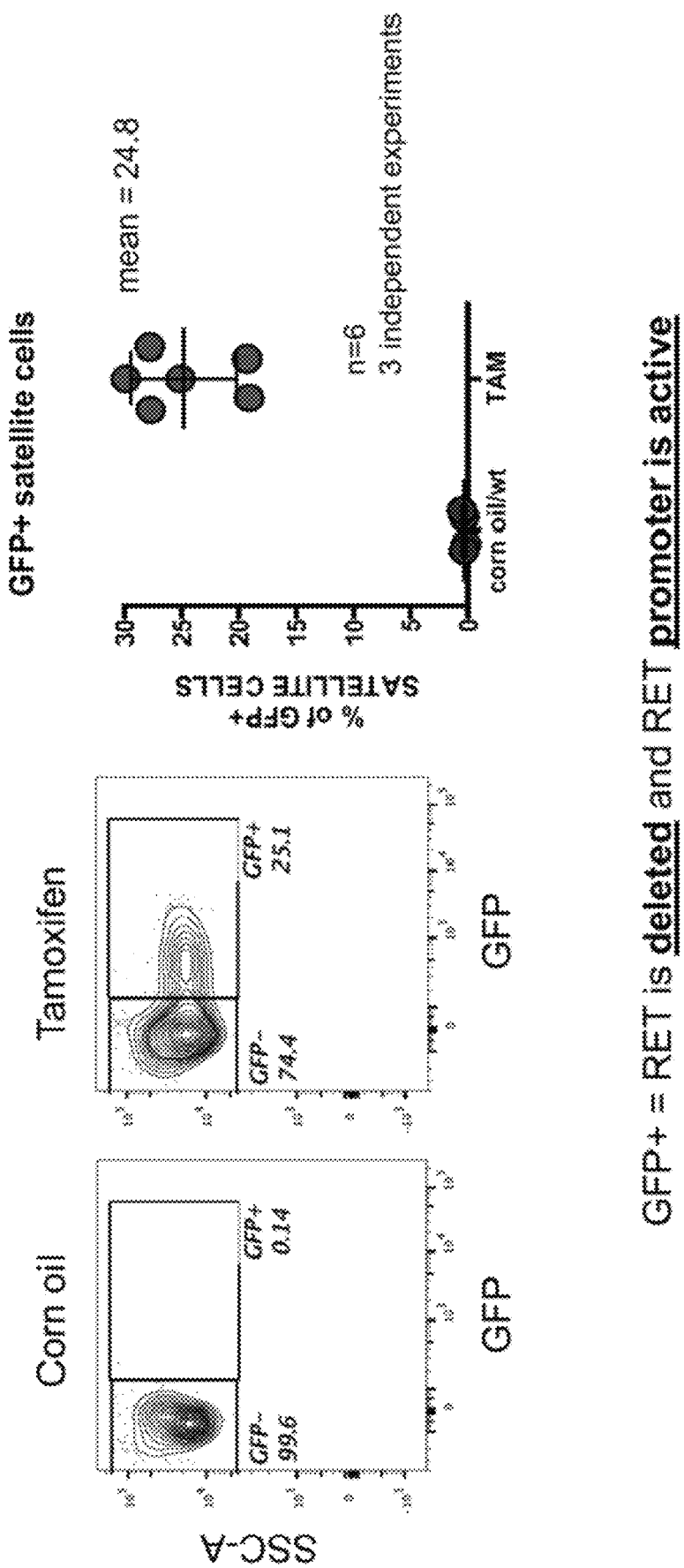

FIG. 47 illustrates that by using a conditional RET mutant and reporter, the present inventors were able to determine that the RET promoter is active in at least 25% of satellite cells.

Figure 48:
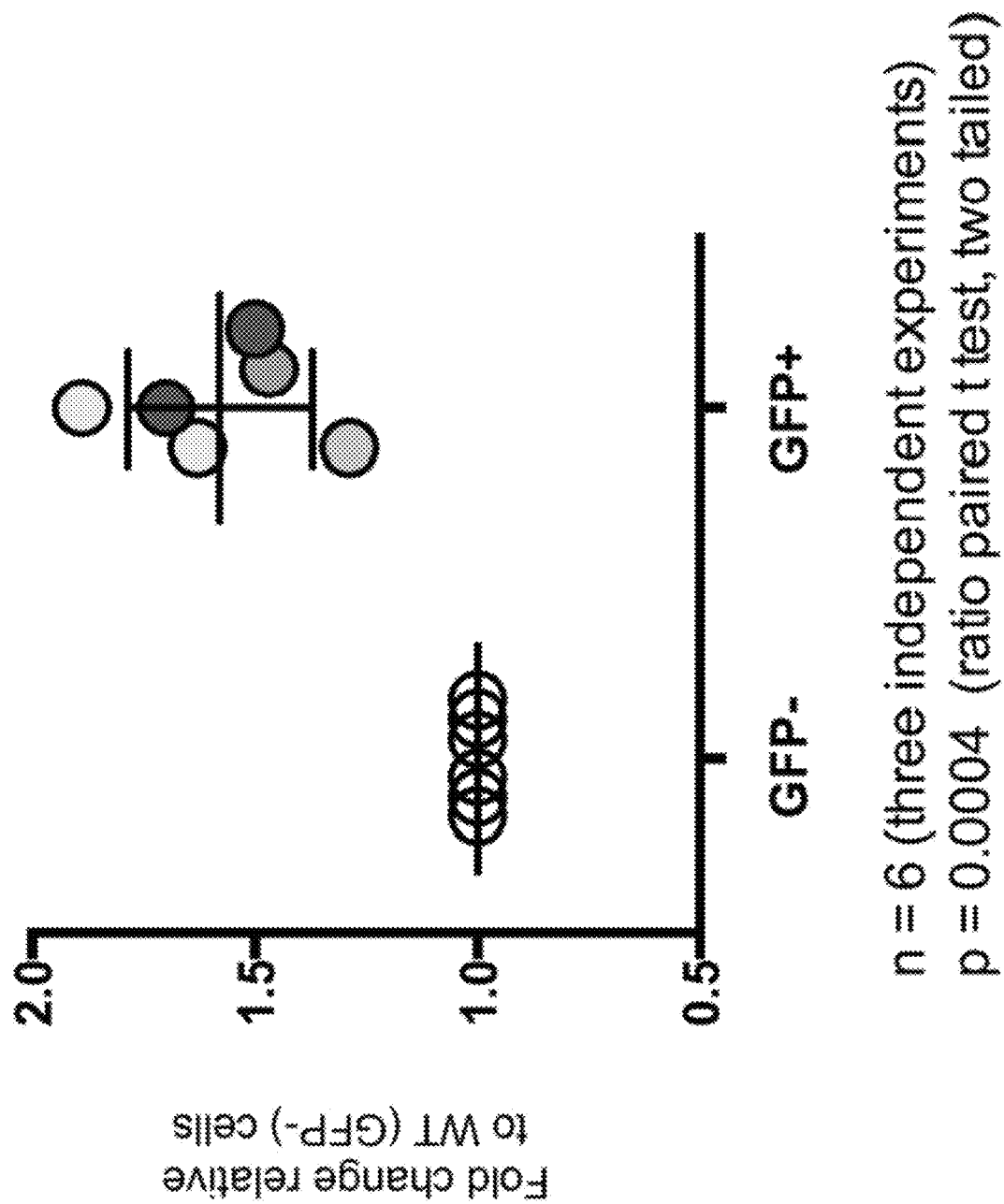

FIG. 48 shows that that RET knockout cells proliferate better than wild-type cells in vitro (n=6; p=0.0004).

Figure 49:
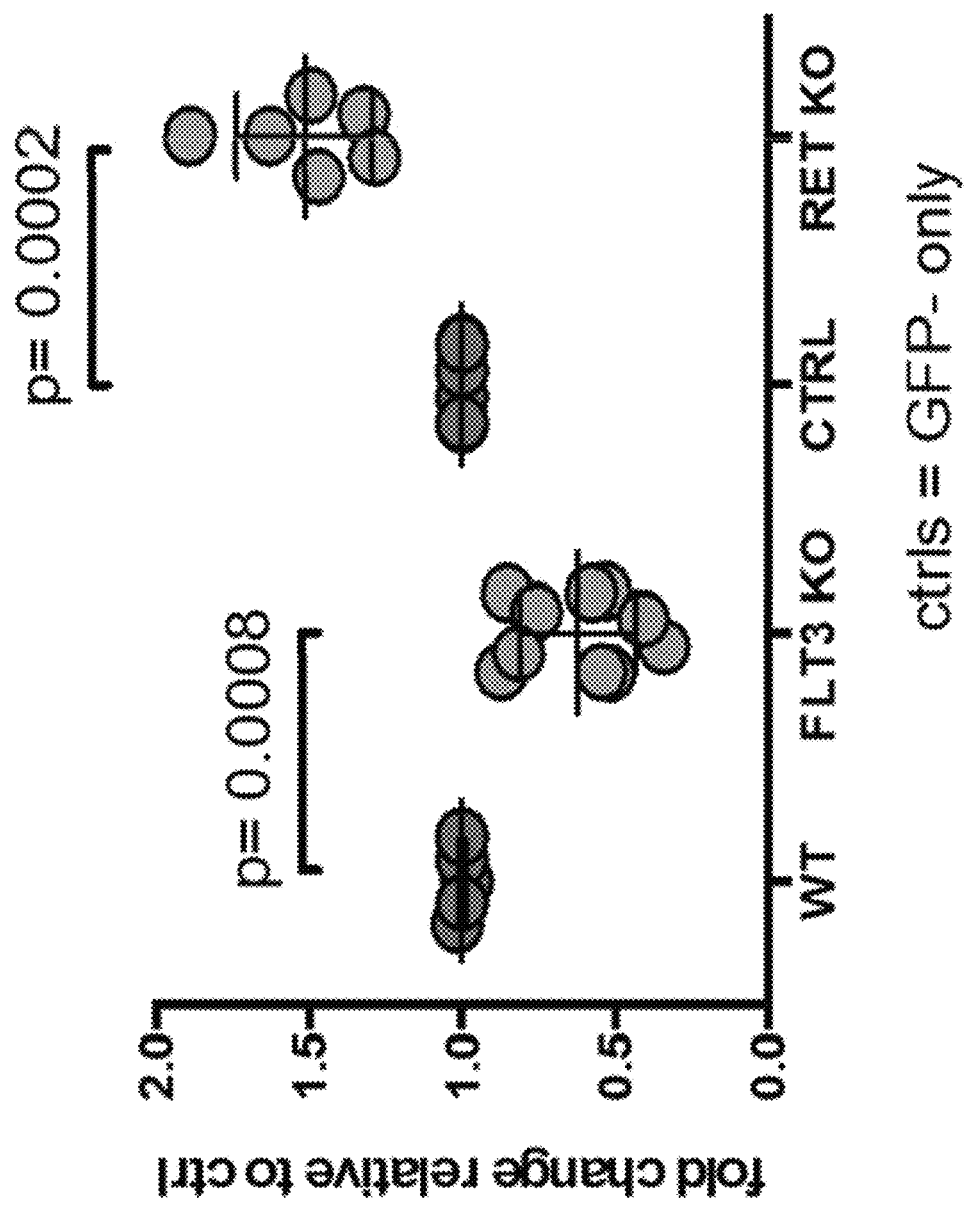

FIG. 49 demonstrates the fold change relative to control of untreated FLT3 and RET knockout cells.

DETAILED DESCRIPTION OF EXEMPLARY EMBODIMENTS

Provided herein is a method of increasing satellite cell proliferation. The method comprising contacting a satellite cell with a compound selected from the group consisting of kinase inhibitors, G protein coupled receptor (GPCR) modulators, histone deacetylase (HDAC) modulators, hedgehog signaling pathway modulators, neuropeptides, dopamine receptor modulators, serotonin receptor modulators, histamine receptor modulators, adenosine receptor agonists, ionophores, ion channel modulators, adenosine receptor modulators, gamma-secretase modulators, corticosteroids, any combination thereof.

As used herein, the term "proliferation" means growth and division of cells. In some embodiments, the term "proliferation" as used herein in reference to cells refers to a group of cells that can increase in number over a period of time.

As used herein, "inducing,", "enhancing," or "increasing" satellite cell proliferation means that satellite cells replicate at a faster rate and/or more frequently. In some embodiments of this and other aspects described herein, satellite cell proliferation is increased by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control. The % or fold increase in satellite cell proliferation can be determined by measuring number of replicating satellite cells while in contact with a compound described herein relative to a control where the satellite cells are not in contact with the compound. Increase in proliferation can also be based on ratios of replicating cells to total number of cells in the respective treated and untreated control. In some embodiments, total number of cells in the treated and untreated controls is used to determine the proliferation. Satellite cell proliferation can be determined using the BrdU incorporation method described in U.S. Patent Publication No. 2009/0136481, content of which is incorporated herein by reference.

Myosatellite cells or satellite cells are small mononuclear progenitor cells with virtually no cytoplasm found in mature muscle. They are found sandwiched between the basement membrane and sarcolemma (cell membrane) of individual muscle fibers, and can be difficult to distinguish from the sub-sarcolemmal nuclei of the fibers. Satellite cells are able to differentiate and fuse to augment existing muscle fibers and to form new fibers. These cells represent the oldest known adult stem cell niche, and are involved in the normal growth of muscle, as well as regeneration following injury or disease.

In undamaged muscle, the majority of satellite cells are quiescent; they neither differentiate nor undergo cell division. In response to mechanical strain, satellite cells become activated. Activated satellite cells initially proliferate as skeletal myoblasts before undergoing myogenic differentiation.

Markers characteristic of satellite cells include the expression of cell surface proteins or the encoding genes, the expression of intracellular proteins or the encoding genes, cell morphological characteristics, and the like. Those skilled in the art will recognize that known immunofluorescent, immunochemical, polymerase chain reaction, in situ hybridization, Northern blot analysis, chemical or radiochemical or biological methods can readily ascertain the presence or absence of satellite cell specific characteristics.

If desired, the type(s) of cells in a population of satellite can be determined using techniques that are well known in the art. For example, the use of cell-type specific stains. Alternatively, one can perform immunofluorescence staining using antibodies directed to various satellite cell specific proteins. In addition, a cell type can be determined by its morphology using techniques such as, for example, light microscopy, or electron microscopy.

Satellite cells express a number of distinctive genetic markers. For example, current thinking is that all satellite cells express PAX7 and PAX3 (F. Rlaix et al. Nature, 2005, 435(7044): 898-899). Activated satellite cells express myogenic transcription factors, such as Myf5 and MyoD. They also begin expressing muscle-specific filament proteins such as desmin as they differentiate.

Little is known of the regulation of satellite cells. Whilst together PAX3 and PAX7 currently form the definitive satellite markers, Pax genes can be poor transcriptional activators. The dynamics of activation and quiesence and the induction of the myogenic program through the myogenic regulatory factors, Myf5, MyoD, myogenin, and MRF4 remains to be determined. There is some research indicating that satellite cells are negatively regulated by a protein called myostatin. Increased levels of myostatin up-regulate a cyclin-dependent kinase inhibitor called p21 and thereby induce the differentiation of satellite cells.

In some embodiments, the satellite cells are in a stabilized state, e.g., the cells were taken from a subject and treated in such a manner as to allow them to be stored for some period of time. For example, the cells can be frozen, e.g., using methods known in the art for freezing primary cells, such that the cells are viable when thawed. For example, methods known in the art to freeze and thaw embryos to generate live mammals can be adapted for use in the present methods. Such methods can include the use of liquid nitrogen, e.g., with one or more cryoprotectants, e.g., agents that prevent freeze-thaw damage to the cell.

Kinase Inhibitors

As used herein, the term "kinase" means any phosphotransferase enzyme that transfers a phosphate group. In some embodiments, the kinase is a protein kinase. Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues.

Protein kinases include, for example, but are not limited to, members of the Protein Tyrosine Kinase family (PTKs), which in turn can be divided into the cytoplasmic PTKs and the receptor PTKs (RTKs). The cytoplasmic PTKS include the SRC family, (including: BLK; FOR; FYN; HCK; LCK; LYN; SRC; YES and YRK); the BRK Family (including: BRK; FRK, SAD; and SRM); the CSK family (including: CSK and CTK); the BTK family, (including: BTK; ITK;

TEC; MKK2 and TXK), the Janus kinase family, (including: JAKI, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRa, PDGFRl3, CSF1R, KIT, FLK2); the VEGF-Receptor family (including; FLT1, FLK1 and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO 10); the ROS family (including ROS); the RET family (including RET); the LTK family (including LTK and ALK); the ROR family (including ROR1 and ROR2); The Musk family (including Musk); the LMR family including LMR1, LMR2 and LMR3); and the SuRTK106 family (including SuRTK106).

Representative, non-limiting examples of kinases include Abl, Abl(T3151), ALK, ALK4, AMPK, Arg, Arg, ARKS, ASK1, Aurora-A, Axl, Blk, Bmx, BRK, BrSK1, BrSK2, BTK, CaMKI, CaMKII, CaMKIV, CDKl/cyclinB, CDK2/cyclinA, CDK2/cyclinE, CDK3/cyclinE, CDK5/p25, CDK5/p35, CDK6/cyclinD3, CDK7/cyclinH/MAT1, CDK9/cyclin Tl, CHK1, CHK2, CKl(y), CK18, CK2, CK2a2, cKit(D816V), cKit, c-RAF, CSK, cSRC, DAPK1, DAPK2, DDR2, DMPK, DRAK1, DYRK2, EGFR, EGFR(L858R), EGFR(L861Q), EphA1, EphA2, EphA3, EphA4, EphAS, EphAV, EphAS, EphB1, EphB2, EphB3, EphB4, ErbB4, Per, Fes, FGFR1, FGFR2, FGFR3, FGFR4, Fgr, Fill, Flt3 (D835Y), Flt3, Flt4, Fms, Fyn, GSK3(3, GSK3a, Hck, HIPK1, HIPK2, HIPK3, IGF-1R, IKK(3, IKKa, IR, IRAKI, IRAK4, IRR, ITK, JAK2, JAK3, JNKIal, JNK2a2, JNK3, KDR, Lck, LIMK1, LKB1, LOK, Lyn, Lyn, MAPK1, MAPK2, MAPK2, MAPKAP-K2, MAPKAP-K3, MARK1, MEK1, MELK, Met, MINK, MKK4, MKK6, MKK7(3, MLCK, MLK1, Mnk2, MRCK-beta, MRCKa, MSK1, MSK2, MSSK1, MST1, MST2, MST3, MuSK, NEK2, NEKS, NEK6, NEK7, NLK, p70S6K, PAK2, PAK3, PAK4, PAK6, PAR-lBa, PDGFR(3, PDGFRa, PDK1, PI3K beta, PI3K delta, PI3K gamma, Pim-1, Pim-2, PKA(b), PKA, PKB(3, PKBa, PKBy, PKC^i, PKC(3I, PKC(3II, PKCa, PKCy, PKC8, PKCe, PKC^, PKCr|, PKC9, PKCi, PKD2, PKG1(3, PKGla, Plk3, PRAK, PRK2, PrKX, PTK5, Pyk2, Ret, RIPK2, ROCK-I, ROCKII, ROCK-II, Ron, Ros, Rse, Rskl, Rskl, Rsk2, Rsk3, SAPK2a, SAPK2a(T106M), SAPK2b, SAPK3, SAPK4, SGK, SGK2, SGK3, SIK, Snk, SRPK1, SRPK2, STK33, Syk, TAKI, TBK1, Tie2, TrkA, TrkB, TSSK1, TSSK2, WNK2, WNK3, Yes, ZAP-70, ZIPK. In some embodiments, the kinases may be ALK, Aurora-A, Axl, CDK9/cyclin Tl, DAPK1, DAPK2, Per, FGFR4, GSK3 (3, GSK3a, Hck, JNK2a2, MSK1, p70S6K, PAK3, PI3K delta, PI3K gamma, PKA, PKB(3, PKBa, Rse, Rsk2, Syk, TrkA, and TSSK1. In yet other embodiments the kinase is selected from the group consisting of ABL, AKT, AURORA, CDK, DBF2/20, EGFR, EPH/ELK/ECK, ERK/MAPKFGFR, GSK3, IKKB, INSR, JAK DOM 1/2, MARK/ PRKAA, MEK/STE7, MEKK/STE11, MLK, mTOR, PAK/STE20, PDGFR, PI3K, PKC, POLO, SRC, TEC/ATK, and ZAP/SYK.

Similarly, the serine/threonine specific kinases comprise a number of distinct sub-families, including; the extracellular signal regulated kinases, (p42/ERK2 and p44/ERKI); c-Jun NH2-terminal kinase (JNK); cAMP-responsive element-binding protein kinases (CREBK); cAMP dependent kinase (CAPK); mitogen-activated protein kinase-activated protein kinase (MAPK and its relatives); stress-activated protein kinase-p38/SAPK2; mitogen-and stress-activated kinase (MSK); protein kinases, PKA, PKB and PKC inter alia.

In some embodiments, the kinase is a FMS-like tyrosine kinase 3 (Flt3), PDGFR/EGFR, Bcr-abl, Jak3, or SRC kinase inhibitor. Flt3 is also known as FLK2 (Fetal Liver Kinase-2) and STK1 (human Stem Cell Kinase-1).

As used herein, the term "kinase inhibitor" means any compound, molecule or composition that inhibits or reduces the activity, e.g., phosphotransferase activity, of a kinase. Without limitations, a kinase inhibitor can be selected from the group consisting of small or large organic or inorganic molecules; monosaccharides; disaccharides; trisaccharides; oligosaccharides; polysaccharides; biological macromolecules, e.g., proteins, peptides, peptide analogs and derivatives thereof, peptidomimetics, nucleic acids, nucleic acid analogs and derivatives, enzymes, antibodies, portion or fragments of antibodies; an extract made from biological materials such as bacteria, plants, fungi, or animal cells or tissues; naturally occurring or synthetic compositions; and any combinations thereof.

A wide variety of kinase inhibitors are known in the art and can be used in the compositions and methods described herein. A kinase inhibitor can be selected form the group consisting of FMS-like tyrosine kinase 3 inhibitor; Aurora kinase inhibitor; Aurora-B kinase inhibitor; Aurora-C kinase inhibitor; Beta-adrenergic receptor kinase inhibitor; Check point kinase inhibitor; Cyclin-dependent kinase 1 inhibitor; Cyclin-dependent kinase 2 inhibitor; Cyclin-dependent kinase 4 inhibitor; Cyclin-dependent kinase inhibitor; EphB2 kinase inhibitor; Epidermal growth factor receptor kinase inhibitor; N-acylmannosamine kinase inhibitor; MAP kinase inhibitor; Opheline kinase inhibitor; Phosphatidylinositol 3-kinase beta inhibitor; Phosphatidylinositol 3-kinase gamma inhibitor; Protein kinase (CK1) inhibitor; Protein kinase B inhibitor; Protein kinase C eta inhibitor; Protein-serine-threonine kinase inhibitor; Proto-oncogene tyrosine-protein kinase Fyn inhibitor; Proto-oncogene tyrosine-protein kinase Kit inhibitor; Pyridoxal kinase inhibitor; Raf kinase B inhibitor; Raf kinase inhibitor; Rho-associated kinase inhibitor; Ribosomal protein S6 kinase inhibitor; and any combination thereof.

In certain aspects, the compounds disclosed herein are RET kinase inhibitors. In certain aspects, the compounds disclosed herein (e.g., CEP-701 and/or AC220) are or comprise a RET inhibitor or otherwise inhibit RET phosphorylation. In certain aspects, the compounds disclosed herein (e.g., CEP-701 and/or AC220) are or comprise a C-RET inhibitor or otherwise inhibit C-RET phosphorylation.

Also contemplated are compounds and compositions that reduce RET kinase ligands. For example, in certain aspects the compounds and compositions disclosed comprise an antibody or agent that interferes with RET kinase activation, such as antibodies and agents that bind to or otherwise interfere with the binding of a C-RET ligand (e.g., GDNF) to C-RET.

Kinase inhibitors amenable to the compositions and methods described herein are also described, for example in U.S. Pat. Nos. 5,674,998; 5,795,977; 5,864,033; 6,194,939; 6,239,133; 6,346,625; 6,391,894; 6,448,277; 6,492,409; 6,498,165; 6,706,711; 6,723,726; 6,825,190; 6,825,355; 6,943,161; 6,951,859; 6,982,266; 6,982,266; 7,056,925; 7,101,884; 7,105,531; 7,105,531; 7,115,597; 7,153,856; 7,183,307; 7,196,090; 7,199,137; 7,199,147; 7,223,757; 7,232,826; 7,262,199; 7,265,134; 7,309,787; 7,314,940; 7,326,713; 7,326,713; 7,449,488; 7,456,169; 7,459,554; 7,470,693; 7,470,713; 7,488,826; 7,504,429; 7,511,040; 7,514,435; 7,517,882; 7,521,460; 7,528,132; 7,550,478; 7,550,598; 7,572,914; 7,582,652; 7,598,272; 7,601,852; 7,618,982; 7,635,703; 7,648,987; 7,662,977; 7,683,060; 7,687,506; 7,732,613; 7,749,994; 7,767,674; 7,790,739; 7,812,166; 7,820,662; 7,855,211; 7,872,031; 7,893,064; 7,893,081; 7,901,894; 7,915,443; 7,943,629; 7,968,546; 7,994,159; 7,998,507; 8,022,057; 8,024,821; 8,026,234; 8,026,246; 8,026,247; 8,044,221; 8,093,239; 8,093,383; 8,143,410; 8,148,361; and 8,152,630 and U.S. Patent Publication Nos. 20070161673; 20090181940; 20090215785; 20100097654; 20100234404; 20110008211; 20030044203; 20030065180; 20030087919; 20030119839; 20030139462; 20030187001; 20030199511; 20030199525; 20030216446; 20040034038; 20040034075; 20040082581; 20040180897; 20040192725; 20050043347; 20050096324; 20050131022; 20050153990; 20050171076; 20050187247; 20050192304; 20050203114; 20050215556; 20050239794; 20050239815; 20050261318; 20050267133; 20050277642; 20050277642; 20050288290; 20050288321; 20050288321; 20060019958; 20060058304; 20060058341; 20060079563; 20060122389; 20060122389; 20060148824; 20060178388; 20060217369; 20060264438; 20060270694; 20060276490; 20060281789; 20060287370; 20060287381; 20070049600; 20070054906; 20070060619; 20070078140; 20070099856; 20070099935; 20070123534; 20070173516; 20070173525; 20070185139; 20070191420; 20070191420; 20070203143; 20070213386; 20070254896; 20070259869; 20070270425; 20070280928; 20080027063; 20080108611; 20080153869; 20080161297; 20080167330; 20080207613; 20080207613; 20080207632; 20080255155; 20080255184; 20080269244; 20080293714; 20080293785; 20080312307; 20090054425; 20090054436; 20090105209; 20090124602; 20090131407; 20090131437; 20090131506; 20090149389; 20090162376; 20090175852; 20090197862; 20090215750; 20090221616; 20090233960; 20090264446; 20090286779; 20090298855; 20090318440; 20100004234; 20100041645; 20100041684; 20100041684; 20100048599; 20100081662; 20100093767; 20100099710; 20100113454; 20100120772; 20100120801; 20100144732; 20100144745; 20100160303; 20100168102; 20100179134; 20100179146; 20100190816; 20100204221; 20100222342; 20100234386; 20100298301; 20100317643; 20100324041; 20100331314; 20110009410; 20110070317; 20110077237; 20110118285; 20110124623; 20110136789; 20110190280; 20110195980; 20110257238; 20110269739; 20110269772; 20110275630; 20110281857; 20110281866; 20110288097; 20110293745; 20110294812; 20120015937; 20120041024; 20120053187; 20120065213; 20120071490; 20120071494; 20120077851; 20120095014; 20120095233; 20120212961; 20100267774; and 20100324074, content of all of which is incorporated herein by reference.
In some embodiments, the kinase inhibitor can be selected from the group consisting of
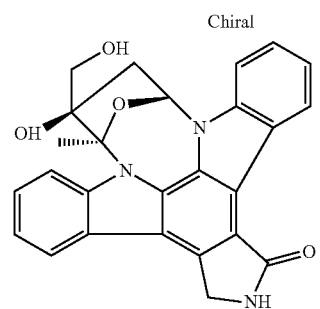
Lestaurtinib (CEP701, ),
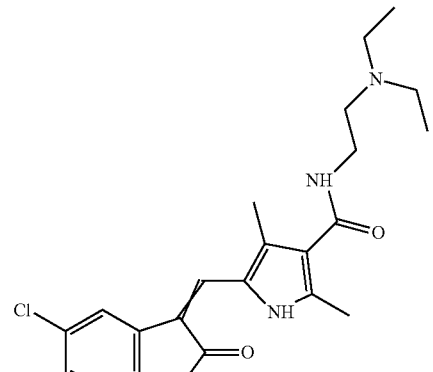
SU11652 ( ),
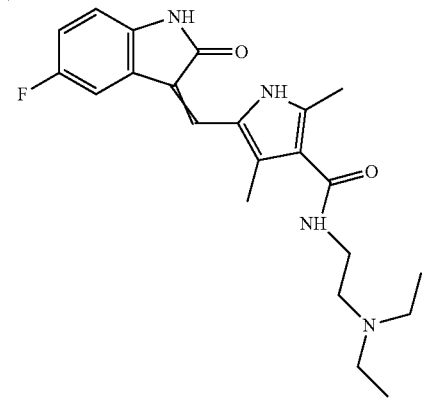
Sunitinib (SU 11248, ),
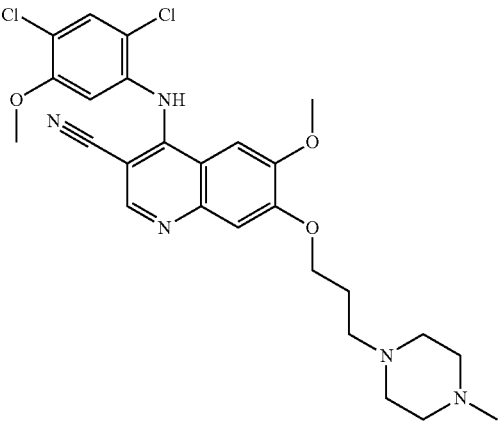
Bosutinib (SKI 606, ),

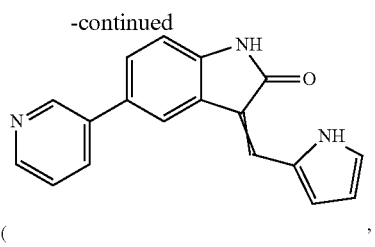

Jak3 Inhibitor VI (                    ), and any combination thereof.

In some embodiments, the kinase inhibitor is or comprises quizartinib (AC220), or any salt, ester or chelate thereof. In certain embodiments, the kinase inhibitor is (AC220)

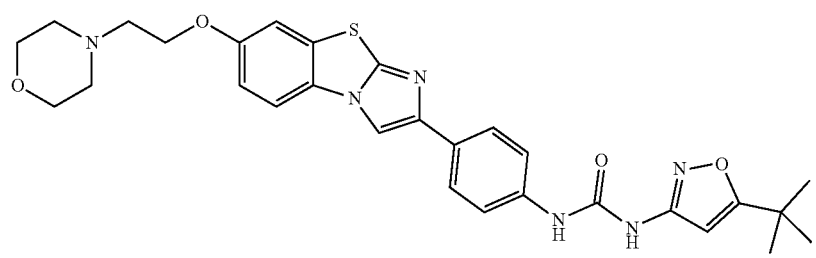

.

In some embodiments of this and other aspects described herein, activity of the kinase is inhibited or lowered by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control. Without wishing to be bound by theory, activity of a kinase can be determined using any assay known in the art for measuring the activity of the kinase, e.g., by measuring phosphorylation reactions.

Hedgehog Signaling Pathway Modulators

As used herein, the term "modulate," with reference to the Hedgehog signaling pathway, means to regulate positively or negatively the normal functioning of a component in the Hedgehog signaling pathway. Thus, the term modulate can be used to refer to an increase, decrease, masking, altering, overriding or restoring the normal functioning of a component in the Hedgehog signaling pathway.

In some embodiments of the aspects described herein, the modulator modulates at least one activity of the hedgehog signaling pathway by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

The term "Hedgehog signaling pathway", "Hedgehog pathway" and "Hedgehog signal transduction pathway" are all used to refer to the chain of events normally mediated by Hedgehog, smoothened, Ptch1, and Gli, among others, and resulting in a changes in gene expression and other phenotypic changes typical of Hedgehog activity. Activating a downstream component can activate the Hedgehog pathway even in the absence of a Hedgehog protein. For example, overexpression of smoothened will activate the pathway in the absence of Hedgehog, Gli and Ptch1 gene expression are indicators of an active Hedgehog-signaling pathway. Accordingly, compounds described herein can be used to overcome an inappropriate increase in Hedgehog signal transduction, whether said increase in signal transduction is the result in a mutation/lesion in a component of the Hedgehog signaling pathway (e.g., Ptch1, Gli1, Gli3, smoothened, etc.) or whether said increase in signal transduction occurs in the context of a cell which does not comprise a mutation/lesion in a component of the Hedgehog signaling pathway (e.g., a wildtype cell with respect to components of the Hedgehog signaling pathway). Thus, in some embodiments, the cell has a phenotype of smoothened gain-of-function, Hedgehog gain-of-function, patched (Ptc) loss-of-function, Gli gain-of-function, and/or over expression of Hedgehog ligands.

The term "smoothened gain-of-function" refers to an aberrant modification or mutation of a smo gene, or an increased level of expression of the gene, which results in a phenotype that resembles contacting a cell with a Hedgehog protein, e.g., aberrant activation of a Hedgehog pathway. While not wishing to be bound by any particular theory, it is noted that Ptch1 may not signal directly into the cell, but rather modulates the activity of smoothened, another membrane bound protein located downstream of Ptch1 in Hedgehog signaling (Marigo et al., (1996) Nature 384: 177-179; Taipale et al. (2002) Nature 418, 892-896). The gene smo is a segment polarity gene required for the correct patterning of every segment in *Drosophila* (Alcedo et al., (1996) *Cell* 86:221232). Human homologs of smo have been identified. See, for example, Stone et al. (1996) Nature 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. Ptc is a Hh receptor. Cells that express Smo fail to bind Hh, indicating that smo does not interact directly with Hh (Nusse, (1996) Nature 384: 119120). Rather, the binding of Sonic Hedgehog (SHH) to its receptor, PTCH is thought to prevent normal inhibition by PTCH of smoothened. Activating smoothened mutations are known to occur in sporadic basal cell carcinoma (Xie, et al., Nature, 1998, 391: 90-92), and in primitive neuroectodermal tumors of the central nervous system (Reifenberger, et al., *Cancer Res.*, 1998, 58:1798-1803).

The term "Hedgehog gain-of-function" refers to an aberrant modification or mutation of a Ptch1 gene, Hedgehog gene, or smoothened gene, or a decrease (or loss) in the level of expression of such a gene, which results in a phenotype which resembles contacting a cell with a Hedgehog protein, e.g., aberrant activation of a Hedgehog pathway. The gain-of-function may include a loss of the ability of the Ptch1 gene product to regulate the level of expression of Ci homolog genes, e.g., Gli 1, Gli2, and Gli3. The term "Hedgehog gain-of-function" is also used herein to refer to any similar cellular phenotype (e.g., exhibiting excess proliferation) that occurs due to an alteration anywhere in the Hedgehog signal transduction pathway, including, but not limited to, a modification or mutation of Hedgehog itself. For example, a tumor cell with an abnormally high proliferation rate due to activation of the Hedgehog signaling pathway would have a "Hedgehog gain-of-function" phenotype, even if Hedgehog is not mutated in that cell.

The term "patched loss-of-function" refers to an aberrant modification or mutation of a Ptch1 gene, or a decreased level of expression of the gene, which results in a phenotype which resembles contacting a cell with a Hedgehog protein, e.g., aberrant activation of a Hedgehog pathway. The loss-of-function may include a loss of the ability of the Ptch1 gene product to regulate the level of expression or activity of Ci homolog genes, e.g., Gli1, Gli2, and Gli3. The term 'Ptch1 loss-of function' is also used herein to refer to any similar cellular phenotype (e.g., exhibiting excess proliferation) that occurs due to an alteration anywhere in the Hedgehog signal transduction pathway, including, but not limited to, a modification or mutation of Ptch1 itself. For example, a tumor cell with an abnormally high proliferation rate due to activation of the Hedgehog signaling pathway would have a "Ptch1 loss-of-function" phenotype, even if Ptch1 is not mutated in that cell.

The term "Gli gain-of-function" refers to an aberrant modification or mutation of a Gli gene, or an increased level of expression of the gene, which results in a phenotype that resembles a cell responding to a Hedgehog protein, e.g., aberrant activation of a Hedgehog pathway.

The vertebrate family of Hedgehog genes includes three members that exist in mammals, known as Desert (Dhh), Sonic (Shh) and Indian (Ihh) Hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is processed to a repressor form and nuclear accumulation of activator forms prevented through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself. Increased levels of Hedgehog signaling are sufficient to initiate cancer formation and are required for tumor survival.

The Hedgehog signaling pathway modulator can be an agonist or antagonist of the hedgehog signaling pathway.

The term "hedgehog agonist" refers to an agent which antagonizes or blocks the bioactivity of patched, such as to increase transcription of target genes. The hedgehog antagonists can be used to overcome a ptc gain-of-function and/or a smoothened loss-of-function, the latter also being referred to as "smoothened agonists" The term "hedgehog antagonist" likewise refers not only to any agent that may act by directly inhibiting the normal function of the hedgehog protein, but also to any agent that inhibits the hedgehog signaling pathway, and thus recapitulates the function of ptc.

Exemplary hedgehog signaling pathway modulators include, but are not limited to, AY9944, triparanol, jervine, cyclopamine, tomatidine, and the like.

GPCR Modulators

As used herein, the term "modulate," with reference to the GPCRs, means to regulate positively or negatively the normal functioning of a GPCR signaling pathway. Thus, the term modulate can be used to refer to an increase, decrease, masking, altering, overriding or restoring the normal functioning of a GPCR. A GPCR modulator can be a GPCR agonist or a GPCR antagonist.

In some embodiments of the aspects described herein, the modulator modulates at least one activity of the GPCR by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

The G protein-coupled receptors (GPCRs) form a vast superfamily of cell surface receptors which are characterized by an amino-terminal extracellular domain, a carboxyl-terminal intracellular domain, and a serpentine structure that passes through the cell membrane seven times. Hence, such receptors are sometimes also referred to as seven transmembrane (7TM) receptors. These seven transmembrane domains define three extracellular loops and three intracellular loops, in addition to the amino- and carboxy-terminal domains. The extracellular portions of the receptor have a role in recognizing and binding one or more extracellular binding partners (e.g., ligands), whereas the intracellular portions have a role in recognizing and communicating with downstream molecules in the signal transduction cascade.

In all, GPCRs can be grouped into 6 classes based on sequence homology and functional similarity: Class A (or 1) (Rhodopsin-like); Class B (or 2) (Secretin receptor family); Class C (or 3) (Metabotropic glutamate/pheromone); Class D (or 4) (Fungal mating pheromone receptors); Class E (or 5) (Cyclic AMP receptors); and Class F (or 6) (Frizzled/Smoothened). The very large rhodopsin A group has been further subdivided into 19 subgroups (A1-A19). More recently, an alternative classification system called GRAFS (Glutamate, Rhodopsin, Adhesion, Frizzled/Taste2, Secretin) has been proposed.

As used herein, the term "GPCR ligand" refers to molecules that bind GPCRs. The G protein-coupled receptors bind a variety of ligands including calcium ions, hormones, chemokines, neuropeptides, neurotransmitters, nucleotides, lipids, odorants, and even photons, and are important in the normal (and sometimes the aberrant) function of many cell types. [See generally Strosberg, *Eur. J. Biochem.* 196:1-10 (1991) and Bohm et al, *Biochem J.* 322:1-18 (1997).] When a specific ligand binds to its corresponding receptor, the ligand typically stimulates the receptor to activate a specific heterotrimeric guanine-nucleotide-binding regulatory protein (G-protein) that is coupled to the intracellular portion of the receptor. The G protein in turn transmits a signal to an effector molecule within the cell, by either stimulating or inhibiting the activity of that effector molecule. These effector molecules include adenylate cyclase, phospholipases and ion channels. Adenylate cyclase and phospholipases are enzymes that are involved in the production of the second messenger molecules cAMP, inositol triphosphate and diacyglycerol. It is through this sequence of events that an extracellular ligand stimuli exerts intracellular changes through a G protein-coupled receptor. Each such receptor has its own characteristic primary structure, expression pattern, ligand-binding profile, and intracellular effector system.

GPCRs include receptors for sensory signal mediators (e.g., light and olfactory stimulatory molecules); adenosine, bombesin, bradykinin, endothelin, γ-aminobutyric acid (GABA), hepatocyte growth factor (HGF), melanocortins, neuropeptide Y, opioid peptides, opsins, somatostatin, GH, tachykinins, members of the vasoactive intestinal peptide family, and vasopressin; biogenic amines (e.g., dopamine, epinephrine, norepinephrine, histamine, glutamate (metabotropic effect), glucagon, acetylcholine (muscarinic effect), and serotonin); chemokines; lipid mediators of inflammation (e.g., prostaglandins, prostanoids, platelet-activating factor, and leukotrienes); and peptide hormones (e.g., calcitonin, C5a anaphylatoxin, follicle-stimulating hormone (FSH), gonadotropin-releasing hormone (GnRH), neurokinin, thyrotropin-releasing hormone (TRH), cannabinoids, and oxytocin). GPCRs that act as receptors for stimuli that have not yet been identified are known as orphan receptors.

Whereas, in other types of receptors that have been studied, wherein ligands bind externally to the membrane, the ligands of GPCRs typically bind within the transmembrane domain. However, protease-activated receptors are activated by cleavage of part of their extracellular domain.

Types of GPCR ligands include, but are not limited to: agonists which shift the equilibrium in favor of active states; inverse agonists which shift the equilibrium in favor of inactive states; and neutral antagonists which do not affect the equilibrium. When a GPCR in an active state encounters a G-protein, it can activate the G-protein. GPCRs are the target of about 40% of all prescription pharmaceuticals on the market. (Filmore, Modern Drug Discovery, November 2004, pp. 11). Examples of commonly prescribed GPCR-based drugs include Atenolol (TENORMIN®), Albuterol (VENTOLIN®), Ranitidine (ZANTAC®), Loratadine (CLARITIN®), Hydrocodone (VICODIN®) Theophylline (THEODUR®), and Fluoxetine (PROZAC®).

Exemplary GPCR modulators include, but are not limited to, corticotropin releasing factor (CRF), urocortin 1, urocortin 2, usorcortin 3, parathyroid hormone, PTH-related hormone, TIP39, calcitonin, amylin, CGRP (CALCA and CALCB), adrenomedullin, secretin, VIP, PACAP, glucagon, GHRH, GLP-1, GLP-2, Dynorphin A, Dynorphin A amide, Dynorphin A (1-6), Dynorphin A (1-13), Dynorphin A (2-13), Dynorphin A (2-17), MetEnk, Met-Enk-RF-amide, Met-Enk-Arg-Phe, Met-Enk-Glyleu, [D-pGlu1, D-Phe2, D-Trp3,6]-LH-RH, g1-MSH amide, g2-MSH, [N-MePhel, D-Pro4]-Morphiceptin (PLO17), ACTH (Human), Leu-Enk, Adrenomedullin (22-52), Adrenomedullin (26-52) (Human) (ADM antagonist), Agouti 1-40 Amide, Agouti Related Protein (87-132)-Amide, Alpha-MSH, Alpha-Neo-Endorphin, Amylin Amide, BAM(1-20), BAM(1-22), BAM(2-22), BAM(6-22), BAM(1-20), ANP (Atrial Natriuretic Peptide), Anti-Inflammatory Peptide 1, Anti-Inflammatory Peptide 2, (3-endorphin, Benzylureido-Met-Leu-Phe, Beta-ANP, Beta-Endorphin, Beta-MSH, Big Endothelin-1, Big Gastrin-1, BNP (Brain Natriuretic Peptide-32), BNP-45 (Cardiac Natriuretic Peptide, Bombesin, BAM(8-25), BAM (8-20), FLRF, Calcitonin Gene Related Peptide, NPFF, Calcitonin, Calcitonin Gene Related Peptide (8-37), CART (55-1,02), CART (55102)[Met(O)67, CART (61-102), CGRP (8-37), CGRP II, Cholecystokinin Octapeptide [CCK (26-33)], Cholecystokinin-33, CNP-22 (C-Type Natriuretic Peptide), Corticotropin Releasing Factor, Cortistatin-14, NPAF, SST, NPY, FMRFamide, OrpaninFQFMRF amide related peptide, YMRFamide, YLPLRFamide, YFMRFamide, LPLRFamide, dFMRFamide, W-Nle-R-F-amide, and ACEP.

Polypeptide modulators of GPCRs include, but are not limited to, vasopressin, oxytocin, somatostatin, neuropeptide Y, GnRH, leutinizing hormone, follicle stimulating hormone, parathyroid hormone, orexins, urotensin II, endorphins, enkephalins, and the like. A list of GPCR modulators is compiled on the web at pharminfo.pharm.kyoto-u.ac.jp/services/glida/ligand_classification.php In some embodiments, the GPCR modulator inhibits binding of a ligand by at least about or about any one of 10%, 20%, 30%, 40%, 50%, 60%, 70%, 80%, 90%, 95% or 100% relative to a control. Binding of a ligand to a GPCR can be determined by any method known to one of skill in the art.

In some embodiments, the GPCR modulator reduces an activity of a GPCR by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the GPCR modulator enhances an activity of a GPCR by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the GPCR modulator is capable of binding to the active site of a GPCR (e.g., a binding site for a ligand).

In some embodiments, the serotonin receptor modulator is capable of binding to an allosteric site of a GPCR.

In some embodiments of this and other aspects described herein, the GPCR antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the GPCR agonist has an EC50 of less than or equal to 500 nM, 250 nM, 100 nM, 50 nM, 10 nM, 1 nM, 0.1 nM, 0.01 nM or 0.001 nM.

In some embodiments the GPCR modulator can be selected from the group consisting of naltrindole

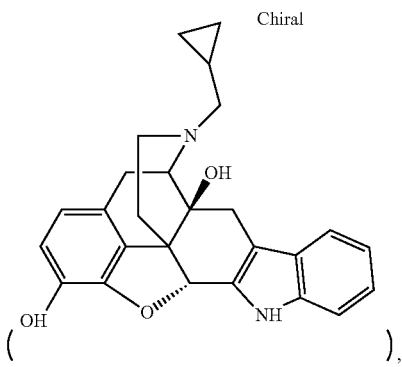

methoctramine tetrahydrochloride

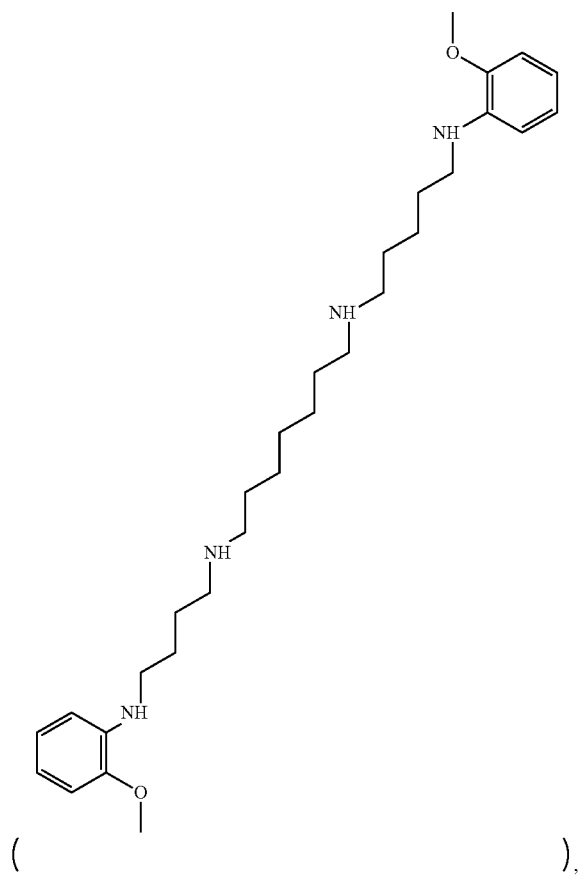

and any combination thereof.

Dopamine Receptor Modulators

As used herein, the term "dopamine receptor modulator" refers to compounds that modulate one or more dopamine receptors. A dopamine receptor modulator can be a dopamine agonist or a dopamine antagonist. As used herein, the term "dopamine agonist" refers to compounds that activate and/or stimulate one or more dopamine receptors and/or increase levels of dopamine (such as L-dopa or drugs which inhibit dopamine metabolism) and/or stimulate a dopamine signaling pathway and/or reduce levels of norepinephrine, and/or inhibit a norepinephrine signaling pathway. The term "dopamine agonist" also includes analogs of dopamine molecules which exhibit at least some biological activity in common with native human dopamine receptors. As such, the term "dopamine agonist" encompasses dopaminergic agents. As used herein the term "dopaminergic agent" refers to compounds which mimic the action of dopamine. Accordingly, the term dopaminergic agent is intended to encompass dopamine, derivatives of dopamine, and compounds which have dopamine like actions on dopamine receptors. Exemplary analogs of dopamine include the ergolines and the aporphines such an apomorphine, pergolide, bromocriptine and lisuride).

In some embodiments of the aspects described herein, the modulator modulates at least one activity of the dopamine receptor by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

Without wishing to be bound by a theory, a dopamine agonist can act via one of several pathways. For example, a dopamine agonist can activate or potentiate D1 dopamine receptors and/or Dj-like receptors such as D1 and D5 dopamine receptors and/or D2 dopamine receptors (e.g., D2, D2 short and D2 long receptors, D4, and D4 dopamine receptors) and/or D3 dopamine receptors and/or D4 dopamine receptors. A dopamine agonist can act by inhibiting one or more enzyme involved in biosynthesis and/or transformation and/or breakdown of dopamine.

Exemplary dopamine agonists include, but are not limited to, (−)-7-{[2-(4-Phenylpiperazin-1-yl)ethyl]propylamino}-5,6,7,8-tetrahydronaphthalen-2-ol; (+)-4-propyl-9-hydroxynaphthoxazine ((+)PHNO); (E)-1-aryl-3-(4-pyridinepiperazin-1-yl)propanone oximes; (R)-3-(4-Propylmorpholin-2-yl)phenol (PF-219,061); (R,R)—S32504; 2-(N-phenylethyl-N-propylamino)-5-hydroxytetralin; 2-bromo-a-ergocriptine (bromocriptine); 5,6,7,8-Tetrahydro-6-(2-propen-1-yl)-4H-thiazolo[4,5-d]azepin-2-amine (BHT-920); 5-HT uptake inhibitor; 5-HT-1A agonists (such as roxindole); 6-Br-APB; 6-methyl-8-a-(N-acyl)amino-9-ergoline; 6-methyl-8-a-(N-phenyl-acety)amino-9-ergoline; 6-methyl-8R-carbobenzyloxy-aminoethyl-10-a-ergoline; 7,8-Dihydroxy-5-phenyl-octahydrobenzo[h]isoquinoline; 8-acylaminoergoline; 9,10-dihydroergocomine; a2-adrenergic antagonist (such as terguride); A-412,997; A-68,930; A-77,636; A-86,929; ABT-670; ABT-724; AF-14; alaptide; amisulpride; any D-2-halo-6-alkyl-8-substituted ergoline; Aplindore; Apomorphine; Aripiprazole (Abilify in USA); benzazepine analogs; BP-897; Bromocriptine; bromocriptine mesylate; Cabergoline; cis-8-Hydroxy-3-(n-propyl)-1,2,3a,4,5,9b-hexahydro-1H- and trans-N-{4-[4-(2,3-Dichlorophenyl)-1-piperazinyl]cyclohexyl}-3-methoxybenzamide; clozapine; COMT inhibitors (such as CGP-28014, entacapone and tolcapone); CP-226,269; CP-96,345; CY-208,243; D-2-bromo-6-methyl-8-cyanomethylergoline; Dihydrexidine; dihydro-alpha-ergocriptine; dihydro-alpha-ergotoxine; dihydroergocriptine; dihydroergocryptine; dihydroergotoxine (hydergine); Dinapsoline; Dinoxyline; domperidone; Dopamine; dopamine D1 receptor agonists; dopamine D2 receptor agonists; dopamine D3 receptor agonists; dopamine D4 receptor agonists; dopamine D5 receptor agonists; dopamine uptake inhibitors (such as GBR-12909, GBR-13069, GYKI-52895, and NS-2141); doprexin; Doxanthrine; ER-230; erfotoxine; Ergocomine; ergoline derivatives; ergot alkaloid derivatives; eticlopride; etisulergine; FAUC 299; FAUC 316; Fenoldopam; Flibanserin; haloperidol; iloperidone; L-dopa; levodopa; Lisuride; lisuride; LSD; LU111995;

mazapertine; Methylphenidate; monoamine oxidase-B inhibitors (such as selegiline, N-(2butyl)-N-methylpropargylamine, N-methyl-N-(2-pentyl) propargylamine, AGN-1133, ergot derivatives, lazabemide, LU-53439, MD-280040 and mofegiline); N-0434; Naxagolide; olanzapine; opiate receptor agonists (such as NIH-10494); PD-118,440; PD-168,077; Pergolide (such as A-68939, A-77636, dihydrexine, and SKF-38393); PIP3EA; piribedil; Piribedil; Pramipexole; Quinagolide; Quinelorane; Quinpirole; racemic trans-10,11-dihydroxy 5,6,6a, 7,8,12b-hexahydro and related benzazepine analogs; raclopride; remoxipride; risperidone; Ro10-5824; Ropinirole; Rotigotine; Salvinorin A; SDZ-HDC-912; sertindole; SKF-38,393; SKF-75,670; SKF-81,297; SKF-82,526 (fenoldopam); SKF-82,598; SKF-82,957; SKF-82,958; SKF-38,393; SKF-77,434; SKF-81,297; SKF-82,958; SKF-89,145; SKF-89,626; spiperone; spiroperidol; sulpride; sumanirole; Talipexole; Terguride; tropapride; WAY-100635; YM 09151-2; zetidoline; β-adrenergic receptor agonists; and analogs, derivatives, enantiomers, metabolites, prodrugs, and pharmaceutically acceptable salts thereof.

Exemplary beta-3 adrenergic receptor agonists include, but are not limited to, DPDMS; dopexamine; AJ-9677; AZ-40140; BMS187413; BMS-194449; BMS-210285; BRL-26830A; BRL-28410; BRL-35135; BRL-37344; CGP 12177; CL-316243; CP-114271; CP-331648; CP-331679; D-7114; FR-149175; GW-2696; GW-427353; ICI-198157; L-750355; L-796568; LY-377604; N-5984; SB-226552; SR-58611A; SR-59062A; SWR0342SA; ZD-2079; and analogs, derivatives, enantiomers, metabolites, prodrugs, and pharmaceutically acceptable salts thereof.

In some embodiments, the dopamine agonist enhances an activity of a dopamine receptor by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the dopamine agonist inhibits the binding of a ligand to its receptor by at least about or about any one of 10%, 20%, 30%, 40%, 50%, 60%, 70%, 80%, 90%, 95% or 100% relative to a control.

In some embodiments, the dopamine receptor modulator is capable of binding to the active site of a dopamine receptor (e.g., a binding site for a ligand).

In some embodiments, the dopamine receptor modulator is capable of binding to an allosteric site of a dopamine receptor.

In some embodiments of this and other aspects described herein, the dopamine agonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the dopamine agonist has an EC50 of less than or equal to 500 nM, 250 nM, 100 nM, 50 nM, 10 nM, 1 nM, 0.1 nM, 0.01 nM or 0.001 nM.

In some embodiments, the dopamine agonist inhibits the dopamine beta-hydroxylase. Dopamine beta-hydroxylase converts dopamine to norepinephrine. Thus, by inhibiting dopamine beta-hydroxylase, intracellular dopamine is increased while norepinephrine is decreased.

Exemplary inhibitors of DBH include, but are not limited to fusaric acid; 1,1',1'',1'''-[disulfanediylbis-(carbonothioylnitrilo)]tetraethane (disulfiram); 2-Hydroxy-2,4,6-cycloheptatrien-1-one (tropolone, also referred to as 2-Hydroxytropone or Purpurocatechol); 5-(aminomethyl)-1-[(2S)-5,7-difluoro-1,2,3,4-tetrahydronaphthalen-2-yl]-1,3-dihydro-2H-imidazole-2-thione (Nepicastat, INN, or SYN117)); 1-(4-hydroxybenzyl)imidazole-2-thiol; FLA-63; diethyidithiocarbamate; betachlorophenethylamine; 4-hydroxybenzyl cyanide; 2-halo-3(p-hydroxyphenyl)-1-propene; 1-phenyl-1-propyne; 2-phenylallylamine; 2-(2-thienyl)allylamine; 2-thiophene-2(2-thienyl)allylamine; 3-phenylpropargylamine; 1-phenyl-1 (aminoethyl)ethane; N-(trifluoroacetyl)phenyl(aminoethyl) ethane; 5-picolinic acid substituted with an alkyl group containing up to 6 carbon atoms; 5-picolinic acid substituted with a halo alkyl group containing up to 6 carbon atoms; and analogs, derivatives, enantiomers, metabolites, prodrugs, and pharmaceutically acceptable salts thereof.

Other inhibitors of dopamine beta-hydroxylase include, but are not limited to U.S. Pat. Nos. 4,487,761; 4,634,711; 4,719,223; 4,743,613; 4,749,717; 4,761,415; 4,762,850; 4,798,843; 4,810,800; 4,835,154; 4,839,371; 4,859,779; 4,876,266; 4,882,348; 4,906,668; 4,935,438; 4,963,568; 4,992,459; 5,100,912; 5,189,052; 5,597,832; 6,407,137; 6,559,186; 7,125,904; 7,576,081, content of all of which is herein incorporated by reference in their entirety.

In some embodiments of this and other aspects of the invention, activity of the dopamine beta-hydroxylase is inhibited or lowered by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the dopamine beta-hydroxylase inhibitor has the desired activity at a concentration that is lower than the concentration of the inhibitor that is required to produce another, unrelated biological effect. In some exemplary embodiments, the concentration of the inhibitor required for dopamine beta-hydroxylase inhibitory activity is at least about 2-fold lower, or at least about 5-fold lower, or at least about 10-fold lower, or at least about 20-fold lower than the concentration required to produce an unrelated biological effect.

In some embodiments of this and other aspects described herein, the dopamine beta-hydroxylase inhibitor has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments, the dopamine receptor modulator inhibits binding of a ligand by at least about or about any one of 10%, 20%, 30%, 40%, 50%, 60%, 70%, 80%, 90%, 95% or 100% relative to a control. Binding of a ligand to a dopamine receptor can be determined by any method known to one of skill in the art.

In some embodiments, the dopamine receptor modulator reduces an activity of a dopamine receptor by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the dopamine receptor modulator enhances an activity of a dopamine receptor by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the dopamine receptor modulator is capable of binding to the active site of a dopamine receptor (e.g., a binding site for a ligand).

In some embodiments, the serotonin receptor modulator is capable of binding to an allosteric site of a dopamine receptor.

In some embodiments of this and other aspects described herein, the GPCR antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the GPCR agonist has an EC50 of less than or equal to 500 nM, 250 nM, 100 nM, 50 nM, 10 nM, 1 nM, 0.1 nM, 0.01 nM or 0.001 nM.

Serotonin Receptor Modulators

As used herein, the term "modulate," with reference to the serotonin receptors means to regulate positively or negatively the normal functioning of the serotonin receptor. Thus, the term modulate can be used to refer to an increase, decrease, masking, altering, overriding or restoring the normal functioning of a serotonin receptor. A serotonin receptor modulator can be an agonist or an antagonist of the serotonin receptor.

In some embodiments of the aspects described herein, the modulator modulates at least one activity of the serotonin receptor by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

Serotonin (5-hydroxytryptamine, 5-HT) is a major neurotransmitter eliciting effects via a multiplicity of receptors. To date, at least fifteen different 5-HT receptors have been identified, largely as the result of cloning cDNA's, and these receptors have been grouped into seven families (5-HT$_1$ through 5-HT$_7$). See, for example, Hoyer, et al., *Pharmacol. Biochem. Behav.* 2002, 71: 533-554. Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion, and cognition.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor or reduces or eliminates or increases or enhances or mimics an activity of a 5-HT1A and/or a 5-HT1B and/or a 5-HT2 A and/or a 5-HT2B and/or a 5-HT2C and/or a 5-HT3 and/or a 5-HT4 and/or a 5-HT6 and/or a 5-HT7 receptor in a reversible or irreversible manner.

In some embodiments, the serotonin modulator is a serotonin receptor antagonist.

Exemplary serotonin modulators include, but are not limited to, (−) cisapride; (−) norcisapride; (−) venlafaxine; (+) cisapride; (+) norcisapride; (+) venlafaxine; 1-(2-fluorophenyl)-3-(4-hy)-prop-2-en-1-one-O-(2-dimethylamino-ethyl)-oxime; [5[3-(4-methylsulphonylamino)-benzy-1-1,2,4-oxadiazol-5yl]-1H-indol-3-yl]ethanamine (L.694247); 2-hydroxymethylolanzapine; 2-Methyl-5-HT; 2C-B; 3-tropanyl-indole-3-carboxylate; 3-tropanyl-indole-3-carboxylate methiodide; 311C90; 5-CT; 5-MeO-DMT; 5-MT; 8-OH-DPAT; A-372,159; Agomelatine; AL-38022A; Almotriptan; alnitidan; alosetron; Alosetron; alpha-Me-5-HT; Alprenolol; Amitriptyline; AR-A000002; Aripiprazole; AS-19; Asenapine; BIMU-8; BMY 7378; BRL-15572; Bufotenin; Buspirone; BVT-933 (Biovitrum); BW-723C86; BZP; Cannabidiol; chlorpromazine; cilansetron; Cinitapride; Cisapride; citalopram; Clomipramine; Clozapine; enanserin; CP-93,129; CP-94,253; Cyanopindolol; Dazopride; demethylcitalopram; demethylsertraline; desipramine; desmethylolanzapine; Dihydroergotamine; Dimebolin; DMT; Dolasetron; DOM; EGIS-12233; Eletriptan; Eletriptan; EMD-386,088; EMDT; Eplivanserin; Etoperidone; Fenfluramine; Flesinoxan; Flibanserin; Fluoxetine; fluphenazine; fluvoxamine; Frovatriptan; Gepirone; GR 127935; Granisetron; haloperidol; homochlorcyclizine; hydrodolasetron; Iloperidone; Imipramine; Iodocyanopindolol; Ipsapirone; Ketanserin; 1-[5(2-thienylmethoxy)-1H-3-indolyl[propan-2-amine hydrochloride (BW723C86); L-Lysine; Lecozotan; Lisuride; Lorcaserin; loxapine; LSD; LY-278,584; LY-53,857; m-chlorophenylpiperazine (MCPP); MDL 11939; MDMA; Mefway; Memantine; Mescaline; Metergoline; Methiothepin; methiothepin; Methysergide; Metoclopramide; Mianserin; Mirtazapine; Mosapride; MS-245; Myristicin; NAN-190; Naratriptan; Naratriptan; Nefazodone; norcisapride; Norfenfluramine; norfluoxetine; nortriptaline; Olanzapine; Ondansetron; oxetorone; Oxprenolol; p-NPPL; paroxetine; perlapine; Piboserod; Pimavanserin; Pindolol; piperazine; Pizotifen; Propanolol; Prucalopride; Psilocin; Psilocybin; Quetiapine; Quetiapine; Risperidone; Quipazine; R-hydroxynefazodone; r(−) fluoxetine; r(+) ondansetron; Rauwolscine; Renzapride; renzapride; risatriptan; Risperidone; Ritanserin; Rizatriptan; Ro04-6790; Robalzotan; RS-56812; RS-67333; RU 24969; RU 24969; s(+) fluoxetine; S15535; SB 206553; SB 216641; SB 242084; SB-258,585; SB-269,970; SB-271,046; SB-357,134; SB-399,885; SB-699,551; SDZ-205,557; sertraline; sibutramine; Spiperone; Sumatriptan; Tandospiroe; Tegaserod; TFMPP; Trazodone; Tropisetron; Tryptamine; UH-301; Urapidil; Valerenic Acid; venlafaxine; WAY-100,135; WAY-100,635; Xaliproden; YM-348; Yohimbine; Zacopride; zalospirone; zatosetron; Ziprasidone; Zolmitriptan; and analogs, derivatives, enantiomers, prodrugs and pharmaceutically acceptable salts thereof.

Additional serotonin modulators include the compounds described in U.S. Pat. Nos. 4,737,496; 4,782,063; 4,788,290; 4,789,673; 4,797,406; 4,903,691; 5,001,133; 5,017,582; 5,130,313; 5,143,916; 5,202,318; 5,232,924; 5,260,303; 5,319,085; 5,356,934; 5,399,557; 5,434,161; 5,516,782; 5,591,749; 5,604,239; 5,612,366; 5,705,509; 5,728,835; 5,736,544; 5,874,429; 5,962,448; 6,187,772; 6,255,306; 6,235,745; 6,271,223; 6,288,101; 6,316,468; 6,353,008; 6,436,964; 6,638,934; 6,686,374; 6,743,913; 6,828,330; 6,911,452; 7,109,339; 7,244,722; 7,297,711; 7,351,707; 7,375,114; 7,592,355; 7,655,691; 7,772,239; 7,781,476; and 7,851,474, and U.S. Pat. App. Pub. No. 2003/0153576; No. 2005/0215555; No. 2006/0003990; No. 2006/0025601; No. 2006/0079567; No. 2006/0100266; No. 2006/0178366; No. 2007/0032481; No. 2007/0244086; No. 2010/0004264; and No. 2010/0069356, content of all of which is incorporated herein by reference in their entirety.

In some embodiments, the serotonin receptor modulator inhibits binding of a ligand by at least about or about any one of 10%, 20%, 30%, 40%, 50%, 60%, 70%, 80%, 90%, 95% or 100% relative to a control. Binding of a ligand to a serotonin receptor can be determined by an assay described, for example, in U.S. Pat. App. Pub. No. 2009/0239854, content of which is incorporated herein by reference in its entirety.

In some embodiments, the serotonin receptor modulator reduces an activity of a serotonin receptor by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the serotonin receptor modulator enhances an activity of a serotonin receptor by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the serotonin receptor modulator is capable of binding to the active site of a serotonin receptor (e.g., a binding site for a ligand).

In some embodiments, the serotonin receptor modulator is capable of binding to an allosteric site of a serotonin receptor.

In some embodiments of this and other aspects of the invention, the serotonin antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the serotonin agonist has an EC50 of less than or equal to 500 nM, 250 nM, 100 nM, 50 nM, 10 nM, 1 nM, 0.1 nM, 0.01 nM or 0.001 nM.

Histamine Receptor Modulators

As used herein, the term "modulate," with reference to the histamine receptors means to regulate positively or negatively the normal functioning of the histamine receptor. Thus, the term modulate can be used to refer to an increase, decrease, masking, altering, overriding or restoring the normal functioning of a histamine receptor. A histamine receptor modulator can be an agonist or an antagonist of the histamine receptor.

In some embodiments of the aspects described herein, the modulator modulates at least one activity of the histamine receptor by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

Histamine receptors belong to the superfamily of G protein-coupled seven transmembrane proteins with histamine as their endogenous ligand. G protein coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. There are four known histamine receptors, $H_1$, $H_2$, $H_3$ and $H_4$.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine H1 and/or H2 and/or H3 and/or H4 receptor or reduces or eliminates or increases or enhances or mimics an activity of a histamine H1 and/or H2 and/or H3 and/or H4 receptor in a reversible or irreversible manner.

In some embodiments, the histamine modulator is a histamine receptor antagonist. Exemplary histamine modulators include, but are not limited, A-349,821; ABT-239; Acrivastine; Alimemazine (trimeprazine); Antazoline; Astemizole; Azatadine; Azelastine; Bepotastine; Bilastine; Bisfentidine; BL-6341A; BL-6548; BMY-25271; BMY-25405; BMY-52368; Brompheniramine; Carbinoxamine; Cetirizine; Chlorcyclizine; Chlorphenamine (chlorpheniramine); Chlorpromazine; Cimetidine; Ciproxifan; Clemastine; Clobenpropit; Clozapine; Cyclizine; Cyproheptadine; D-16637; DA-4634; Desloratadine; Dexchlorpheniramine; Dimebon; Dimenhydrinate; Dimetindene; Diphenhydramine; donetidine; Ebastine; ebrotidine; Embramine; etintidine; Famotidine; famotidine; Fexofenadine; FRG-8701; FRG-8813; Haloperidol; HB-408; HE-30-256; Hydroxyzine; ICI-162846; ICIA-5165; impromidine; JNJ 7777120; Ketotifen; L-643728; Lafutidine; lamtidine; Levocabastine; Levocetirizine; Loratadine; loxtidine; lupitidine; Meclozine; Mepyramine; mifentidine; Mizolastine; Nizatidine; nizatidine; Olonzapin; Olopatadine; ORF-17578; Pheniramine; pifatidine; Promethazine; Quetiapine; Quifenadine; ramixotidine; Ranitidine; Ritanserin; roxatidine; SKF-94482; SR-58042; sufotidine; Terfenadine; Thioperamide; tiotidine; VUF-6002; Wy-45727; zaltidine; and analogs, derivatives, enantiomers, prodrugs and pharmaceutically acceptable salts thereof.

Additional histamine modulators include the compounds described in U.S. Pat. Nos. 3,932,644; 3,980,781; 4,060,621; 4,112,234; 4,117,131; 4,145,546; 4,153,793; 4,154,834; 4,159,329; 4,159,329; 4,218,452; 4,227,000; 4,234,588; 4,250,316; 4,255,248; 4,307,104; 4,309,433; 4,309,433; 4,318,913; 4,337,256; 4,338,328; 4,374,248; 4,374,248; 4,375,341; 4,380,639; 4,385,058; 4,385,058; 4,399,294; 4,432,983; 4,439,437; 4,442,110; 4,447,611; 4,481,199; 4,485,104; 4,496,567; 4,507,296; 4,520,025; 4,521,418; 4,522,943; 4,524,071; 4,526,973; 4,529,723; 4,543,352; 4,551,466; 4,608,380; 4,638,001; 4,645,110; 4,670,487; 4,681,883; 4,694,008; 4,738,969; 4,745,110; 4,764,612; 4,777,179; 4,812,451; 4,812,452; 4,952,589; 5,273,984; 5,486,526; 5,541,343; 5,639,775; 5,753,671; 6,420,560; 6,552,047; 6,936,627; 7,115,600; 7,205,316; 7,256,205, and U.S. Pat. App. Pub. No. 2002/0086859; No. 2004/0138234; No. 2005/0070525; No. 2006/0047114; No. 2006/0069087; No. 2007/0238771; No. 2008/0015200; No. 2009/0239854; No. 2009/0325927; and No. 2010/0022580, content of all which is incorporated herein by reference in their entirety.

In some embodiments, the histamine receptor modulator inhibits binding of a ligand by at least about or about any one of 10%, 20%, 30%, 40%, 50%, 60%, 70%, 80%, 90%, 95% or 100% relative to a control.

In some embodiments, the histamine receptor modulator reduces an activity of a histamine receptor by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the histamine receptor modulator enhances an activity of a histamine receptor by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the histamine receptor modulator is capable of binding to the active site of a histamine receptor (e.g., a binding site for a ligand).

In some embodiments, the histamine receptor modulator is capable of binding to an allosteric site of a histamine receptor.

In some embodiments of this and other aspects of the invention, the histamine antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the histamine agonist has an EC50 of less than or equal to 500 nM, 250 nM, 100 nM, 50 nM, 10 nM, 1 nM, 0.1 nM, 0.01 nM or 0.001 nM.

In some embodiments, the histamine receptor modulator can be methylhistamine dihydrochloride, i.e., histamine R(-)-alpha-methyl-dihydrochloride

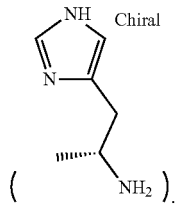

HDAC Modulators

As used herein, the term "modulate," with reference to the HDAC means to regulate positively or negatively the normal functioning of the HDAC. Thus, the term modulate can be used to refer to an increase, decrease, masking, altering, overriding or restoring the normal functioning of a HDAC. A HDAC modulator can be an agonist or an antagonist of the serotonin receptor.

In some embodiments of the aspects described herein, the modulator modulates at least one activity of the HDAC by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

The HDACs are a family including at least eighteen enzymes, grouped in three classes (Class I, II and III). Class I HDACs include, but are not limited to, HDACs 1, 2, 3, and 8. Class I HDACs can be found in the nucleus and are believed to be involved with transcriptional control repressors. Class II HDACs include, but are not limited to, HDACs 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7.

The term "HDAC modulator" as used herein refers to a compound that has the ability to modulate transcriptional activity.

In some embodiments, the HDAC modulator is a HDAC inhibitor. The term "HDAC inhibitor" as used herein refers to a compound that has the ability to inhibit histone deacetylase activity. This therapeutic class is able to block angiogenesis and cell cycling, and promote apoptosis and differentiation. HDAC inhibitors both display targeted anticancer activity by itself and improve the efficacy of existing agents as well as other new targeted therapies.

As used herein, the term "selective HDAC inhibitor" refers to an HDAC inhibitor that does not significantly interact with all three HDAC classes. As used herein, a "Class I selective HDAC" refers to an HDAC inhibitor that interacts with one or more of HDACs 1, 2, 3 or 8, but does not significantly interact with the Class II HDACs (i.e., HDACs 4, 5, 6, 7 and 9).

A number of compounds with HDAC inhibitory activity are known in the art (see e.g., Marks et al., J. Natl. Cancer Inst. 92; 1210-1216 (2000) and Miller et al, J. Med. Chem, 46(24); 5097-5115 (2003), incorporated herein by reference) and can used as an HDAC inhibitory agent of the disclosure. An HDAC inhibitor can be a short-chain fatty acid, such as butyric acid, phenylbutyrate (PB), 4-phenylbutyrate (4-PBA), pivaloyloxymethyl butyrate (Pivanex, AN-9), isovalerate, valerate, valproate, valproic acid, propionate, butyramide, isobutyramide, phenylacetate, 3-bromopropionate, or tributyrin as non-limiting examples. Short-chain fatty acid compounds having HDac inhibitory activity are described in U.S. Pat. Nos. 4,988,731, 5,212,326, 4,913,906, 6,124,495, 6,110,970 6,419,953, 6,110,955, 6,043,389, 5,939455, 6,511,678, 6,528,090, 6,528,091, 6,713,086, 6,720,004, U.S. Patent Publication No. 20040087652, Intl. Publication No. WO 02/007722, and in Phiel et al, J Biol Chem, 276(39):36734-41 (2001), Rephaeli et al, Int J Cancer, 116(2):226-35 (2005), Reid et al. Lung Cancer, 45(3): 381-6 (2004), Gottlicher et al, 2001, EMBO J, 22(13):3411-20 (2003), and Vaisburg et al, Bioorg Med Chem Lett, 14(1):283-7 (2004). An HDac inhibitor can be compound bearing a hydroxyamic acid group, such as suberoylanlide hydroxamic acid (SAHA), trichostatin A (TSA), trichostatin C (TSC), salicylhydroxamic acid, oxamflatin, suberic bishydroxamic acid (SBHA), m-carboxycinnamic acid bishydroxamic acid (CBHA), pyroxamide (CAS RN 382180-17-8), diethyl bis-(pentamethylene-N,Ndimethylcarboxamide) malonate (EMBA), azelaic bishydroxamic acid (ABHA), azelaic-1-hydroxamate-9-anilide (AAHA), 6-(3-Chlorophenylureido) carpoic hydroxamic acid, or A-161906 as non-limiting examples.

Hydroxyamic acid compounds having HDac inhibitory activity are described in U.S. Pat. Nos. 6,800,638, 6,784, 173, 6,531,472, 6,495,719, 6,512,123, and 6,511,990, U.S. Patent Publication Nos. 20060004041, 20050227976, 20050187261, 20050107348, 20050131018, 20050124679, 20050085507, 20040266818, 20040122079, 20040024067, and 20030018062, Intl. Publication Nos. EP1174438, WO/2004092115, WO/2005019174, WO0052033, WO018045, WO018171, WO0138322, WO0170675, WO9735990, WO9911659, WO0226703, WO0230879 and WO0226696, and in Butler et al, Clin Cancer Res., 7: 962-970 (2001), Richon et al, Proc. Natl. Acad. Sci. USA: 95; 3003-3007 (1998), Kim et al. Oncogene: 18(15); U.S. Pat. No. 24,612,470 (1999), Klan et al, Biol Chem., 384(5): 777-85 (2003), Yoshida et al, J Biol Chem., 265(28): 17174-9 (1990), Suzuli et al, Bioorg Med Chem Lett., 15(2):331-5 (2005), Kelly et al, J Clin Oncol., 23(17):3923-31 (2005), Kelly et al, Clin Cancer Res., 9(10 Pt 1):3578-88 (2003), Sonoda et al. Oncogene, 13(1):143-9 (1996), Richon et al, Proc Natl Acad Sci USA., 93(12):5705-8 (1996), Jung et al, J. Med. Chem., 42; 4669-4679. (1999), Jung et al, Bioorg. Med. Chem. Lett, 7(13); 1655-1658 (1997), Lavoie et al, Bioorg. Med. Chem. Letters 11, 2847-2850 (2001), Remiszewski et al, J. Med. Chem. 45, 4, 753-757 (2002), Sternson et al. Org. Lett. 3, 26, 4239-4242 (2001), Bouchain et al, *J Med Chem.*, 46(5):820-30 (2003), and Woo et al, *J Med Chem.*, 45(13):2877-85 (2002).

An HDAC inhibitor can be a cyclic tetrapeptide, such as Depsipeptide (FK228), FR225497, trapoxin A, apicidin, chlamydocin, or HC-toxin as non-limiting examples. Cyclic tetrapeptides having HDAC inhibitory activity are described in U.S. Pat. Nos. 5,922,837, 6,403,555, 6,656,905, 6,399,568, 6,825,317, 6,831,061, U.S. Patent Publication Nos. 20050209134, 20040014647, 20030078369, and 20020120099, and in Kijima et al, *J Biol Chem,* 268(30): 22429-35 (1993), Jose et al, *Bioorg Med Chem* Ze #, 14(21):5343-6 (2004), Xiao et al. *Rapid Commun Mass Spectrom.*, 17(8):757-66 (2003), Furumai et al. *Cancer Res.,* 62(17):4916-21 (2002), Nakajima et al, *Exp. Cell Res.,* 241; 126-133 (1998), Sandor et al, *Clin Cancer Res.,* 8(3):718-28 (2002), Jung et al, *J. Med. Chem.,* 42; 4669-4679. (1999), and Jung et al, *Bioorg. Med. Chem. Lett,* 7(13); 1655-1658 (1997).

An HDAC inhibitor can be a benzamide, such as MS-275. Benzamides having HDAC inhibitory activity are described in U.S. Pat. Nos. 6,174,905 and 6,638,530, U.S. Patent Publication Nos. 2004005513, 20050171103, 20050131018, and 20040224991, Intl. Publication Nos. WO/2004082638, WO/2005066151, WO/2005065681, EP 0847992 and JP 258863/96, and in Saito et al, *Proc. Natl. Acad. Sci. USA,* vol. 96, pp. 45924597 (1999); Suzuki et al, *J. Med. Chem.*, vol. 42, pp. 3001-3003 (1999), Ryan et al, *J Clin Oncol,* 23(17):391222 (2005), Pauer et al. *Cancer Invest.* 22(6): 886-96 (2004), and Undevia et al, *Ann Oncol,* 15(11): 1705-11 (2004).

An HDAC inhibitor can be a depudecin, a sulfonamide anilide (e.g., diallyl sulfide), BL1521, curcumin (diferuloylmethane), CI-994 (N-acetyldinaline), spiruchostatin A, Scriptaid, carbamazepine (CBZ), or a related compound. These and related compounds having HDac inhibitory activity are described in U.S. Pat. No. 6,544,957, and in Lea et al. *Int. J. Oncol,* 15, 347-352 (1999), Ouwehand et al, *FEBS Lett.,* 579(6):1523-8 (2005), Kraker et al, *Mol Cancer Ther.* 2(4):401-8 (2003), de Ruijter et al, *Biochem Pharmacol,* 68(7): 1279-88 (2004), Liu et al. *Acta Pharmacol Sin.,* 26(5):603-9 (2005), Fournel et al. *Cancer Res.,* 62: 4325-4330 (2002), Yurek-George et al, *J Am Chem Soc,* 126(4): 1030-1 (2004), Su et al. *Cancer Res.,* 60(12):3137-42 (2000), Beutler et al. *Life Sci.,* 76(26):3107-15 (2005), and Kwon et al, *Proc. Natl. Acad. Sci. USA* 95, 3356-3361 (1998).

An HDAC inhibitor can be a compound comprising a cyclic tetrapeptide group and a hydroxamic acid group. Examples of such compounds are described in U.S. Pat. Nos. 6,833,384 and 6,552,065, and in Nishino et al, *Bioorg Med Chem.,* 12(22):5777-84 (2004), Nishino et al. *Org Lett,* 5(26):5079-82 (2003), Komatsu et al. *Cancer Res.,* 61(11): 4459-66 (2001), Furumai et al, *Proc Natl Acad Sci USA.,* 98(1):87-92 (2001), Yoshida et al. *Cancer Chemotherapy and Pharmacology,* 48 Suppl. 1; S20-S26 (2001), and Remiszeski et al, *J Med Chem.,* 46(21):4609-24 (2003).

An HDAC inhibitor can be a compound comprising a benzamide group and a hydroxamic acid group. Examples of such compounds are described in Ryu et al. *Cancer Lett.* Jul. 9, 2005 (epub), Plumb et al, *Mol Cancer Ther,* 2(8):721-8 (2003), Ragno et al, *J Med Chem.,* 47(6):1351-9 (2004), Mai et al, *J Med Chem.,* 47(5):1098109 (2004), Mai et al, *J Med Chem.,* 46(4):512-24 (2003), Mai et al, *J Med Chem.,* 45(9):1778-84 (2002), Massa et al, *J Med Chem.,* 44(13): 2069-72 (2001), Mai et al, *J Med Chem.,* 48(9):3344-53 (2005), and Mai et al, *J Med Chem.,* 46(23):4826-9 (2003).

An HDAC inhibitor can be a compound described in U.S. Pat. Nos. 6,897,220, 6,888,027, 5,369,108, 6,541,661, 6,720,445, 6,562,995, 6,777,217, or 6,387,673, 6,693,132, or U.S. Patent Publication Nos. 20060020131, 20060058553, 20060058298, 20060058282, 20060052599, 2006004712, 20060030554, 20060030543, 20050288282, 20050245518, 20050148613, 20050107348, 20050026907, 20040214880, 20040214862, 20040162317, 20040157924, 20040157841, 20040138270, 20040072849, 20040029922, 20040029903, 20040023944, 20030125306, 20030083521, 20020143052, 20020143037, 20050197336, 20050222414, 20050176686, 20050277583, 20050250784, 20050234033, 20050222410, 20050176764, 20050107290, 20040043470, 20050171347, 20050165016, 20050159470, 20050143385, 20050137234, 20050137232, 20050119250, 20050113373, 20050107445, 20050107384, 20050096468, 20050085515, 20050032831, 20050014839, 20040266769, 20040254220, 20040229889, 20040198830, 20040142953, 20040106599, 20040092598, 20040077726, 20040077698, 20040053960, 20040002506, 20030187027, 20020177594, 20020161045, 20020119996, 20020115826, 20020103192, or 20020065282.

An HDAC inhibitor can be inhibitor is selected from the group consisting of FK228, AN-9, MS-275, CI-994, LAQ-824, SAHA, G2M-777, PXD-101, LBH-589, MGCD-0103, MK0683, pyroxamide, sodium phenylbutyrate, CRA-024781, and derivatives, salts, metabolites, prodrugs, and stereoisomers thereof.

Additional non-limiting examples include a reported HDAC inhibitor selected from ONO-2506 or arundic acid (CAS RN 185517-21-9); MGCD0103 (see Gelmon et al. "Phase I trials of the oral histone deacetylase (HDac) inhibitor MGCD0103 given either daily or 3× weekly for 14 days every 3 weeks in patients (pts) with advanced solid tumors." *Journal of Clinical Oncology,* 2005 ASCO Annual Meeting Proceedings. 23(16S, June 1 Supplement), 2005: 3147 and Kalita et al. "Pharmacodynamic effect of MGCD0103, an oral isotype-selective histone deacetylase (HDac) inhibitor, on HDac enzyme inhibition and histone acetylation induction in Phase I clinical trials in patients (pts) with advanced solid tumors or non-Hodgkin's lymphoma (NHL)" *Journal of Clinical Oncology,* 2005 ASCO Annual Meeting Proceedings. 23(16S, Part I of II, June 1 Supplement), 2005: 9631), a reported thiophenyl derivative of benzamide HDac inhibitor as presented at the 97th American Association for Cancer Research (AACR) Annual Meeting in Washington, D.C. in a poster titled "Enhanced Isotype-Selectivity and Antiproliferative Activity of Thiophenyl Derivatives of BenzamideHDac Inhibitors In Human Cancer Cells," (abstract #4725), and a reported HDac inhibitor as described in U.S. Pat. No. 6,541,661; SAHA or Vorinostat (CAS RN 149647-78-9); PXD101 or PXD 101 or PX 105684 (CAS RN 414864-00-9), CI-994 or Tacedinaline (CAS RN 112522-64-2), MS-275 (CAS RN 209783-80-2), or an inhibitor reported in WO2005/108367.

An HDAC inhibitor can be a novel HDac inhibitor identified using structure-activity relationships and teachings known in the art and described, e.g., in Miller et al., *J. Med. Chem.,* 46(24); 5097-5115 (2003) and Klan et al., *Biol Chem.,* 384(5):777-85 (2003)), all of which are incorporated herein by reference in their entirety. Methods to assess histone deacetylase activity are known in the art, and are described, e.g., in Richon et al., *Methods Enzymol,* 376:199-205 (2004), Wegener et al., *Mol Genet Metab.,* 80(1-2): 138-47 (2003), U.S. Pat. No. 6,110,697, and U.S. Patent Publication Nos. 20050118596, 20050227300, 20030161830, 20030224473, 20030082668, 20030013176, and 20040091951), all of which are incorporated herein by reference in their entirety.

Antisense oligonucleotides and ribozymes that inhibit transcription and/or translation of one or more HDacs are described in U.S. Pat. No. 6,953,783, and U.S. Patent Publication Nos. 20050171042, 20040266718, 20040204373, 20040077578, 20040077084, 20040077083, 20040072770, 20030236204, 20030216345, 20030152557, 20030148970, 20030078216, 20020137162, 20020164752, 20020115177, and 20020061860.

Some exemplary inhibitors of HDAC include small molecular weight carboxylates (e.g., less than about 250 amu), hydroxamic acids, benzamides, epoxyketones, cyclic peptides, and hybrid molecules. (See, for example, Drummond D. C., et al. Annu. Rev. Pharmacol. Toxicol. (2005) 45: 495-528, (including specific examples therein) which is hereby incorporated by reference in its entirety). Non-limiting examples HDAC inhibitors include, but are not limited to, Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (i.e., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (i.e., 6-(3-chlorophenylureido)caproic hydroxamic acid), AOE (2-amino-8-oxo-9,10-epoxydecanoic acid), CHAP31 and CHAP 50. Other inhibitors include, for example, dominant negative forms of the HDACs (e.g., catalytically inactive forms) siRNA inhibitors of the HDACs, and antibodies that specifically bind to the HDACs. HDAC inhibitors are commercially available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich. Further HDAC inhibitors amenable to the invention include, but are not limited to, those that are described in U.S. Pat. Nos. 7,183,298; 6,512,123; 6,541,661; 6,531472; 6,960,685; 6,897,220; 6,905,669; 6,888,207; 6,800,638 and 7,169,801, and U.S. patent application Ser. Nos. 10/811,332; 12/286,769; 11/365,268; 11/581,570; 10/509,732; 10/546,153; 10/381,791 and 11/516,620, the contents of which each are incorporated herein by reference in their entirety.

In some embodiments, the HDAC modulator inhibits binding of a ligand by at least about or about any one of 10%, 20%, 30%, 40%, 50%, 60%, 70%, 80%, 90%, 95% or 100% relative to a control.

In some embodiments, the HDAC modulator reduces an activity of a HDAC by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the HDAC modulator enhances an activity of a HDAC by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the HDAC modulator is capable of binding to the active site of a HDAC (e.g., a binding site for a ligand).

In some embodiments, the HDAC modulator is capable of binding to an allosteric site of a HDAC.

In some embodiments of this and other aspects of the invention, the HDAC antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the HDAC agonist has an EC50 of less than or equal to 500 nM, 250 nM, 100 nM, 50 nM, 10 nM, 1 nM, 0.1 nM, 0.01 nM or 0.001 nM.

Neuropeptides

Neuropeptides are small protein-like molecules used by neurons to communicate with each other, distinct from the larger neurotransmitters. They are neuronal signaling molecules, influence the activity of the brain in specific ways and are thus involved in particular brain functions, like analgesia, reward, food intake, learning and memory. Neuropeptides are expressed and released by neurons, and mediate or modulate neuronal communication by acting on cell surface receptors. The human genome contains about 90 genes that encode precursors of neuropeptides. At present about 100 different peptides are known to be released by different populations of neurons in the mammalian brain.

Exemplary neuropeptides include, but are not limited to, hypothalamic hormones such as oxytocin and vasopressin; hypothalamic releasing and inhibiting hormones such as corticotropin releasing hormone (CRH), growth hormone releasing hormone (GHRH), luteinizing hormone releasing hormone (LHRH), somatostatin growth hormone release inhibiting hormone and thyrotropin releasing hormone; tachykinins such as neurokinin a (substance K), neurokinin b, neuropeptide K and substance P; opioid peptides such as b-endorphin, dynorphin and met- and leu-enkephalin; NPY and related peptides such as neuropeptide tyrosine (NPY), pancreatic polypeptide and peptide tyrosine-tyrosine (PYY); VIP-glucagon family members such as glucogen-like peptide-1 (GLP-1), peptide histidine isoleucine (PHI), pituitary adenylate cyclase activating peptide (PACAP) and vasoactive intestinal polypeptide (VIP); as well as many other peptides such as brain natriuretic peptide), calcitonin gene-related peptide (CGRP) (a- and b-form), cholecystokinin (CCK) and other forms, galanin, islet amyloid polypeptide (LAPP) or amylin, melanin concentrating hormone (MCH), melanocortins (ACTH, a-MSH and others), neuropeptide FF (F8Fa), neurotensin, parathyroid hormone related protein, Agouti gene-related protein (AGRP), cocaine and amphetamine regulated transcript (CART)/peptide, endomorphin-1 and -2, 5-HT-moduline, hypocretins/orexins, nociceptin/orphanin FQ, nocistatin, prolactin releasing peptide, secretoneurin and urocortin; Neurotensin; Neuropeptide Y; Neurotensin; Substance P; TRH; Enkephalin; and the like In some embodiments, the neuropeptide can PD160170

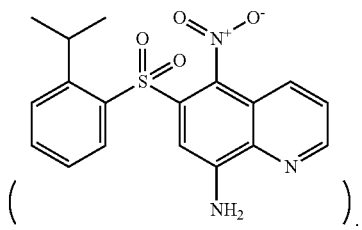

Ionophores

As used herein, the term "ionophore" includes molecules capable of forming a complex with a particular ion, in some instances to the substantial exclusion of others. Generally, an ionophore facilitates transmission of an ion across a lipid barrier by combining with the ion or by increasing the permeability of the barrier to it.

Without limitations, an ionophore can be selected from the group consisting of small or large organic or inorganic molecules; monosaccharides; disaccharides; trisaccharides; oligosaccharides; polysaccharides; biological macromolecules, e.g., proteins, peptides, peptide analogs and derivatives thereof, peptidomimetics, nucleic acids, nucleic acid analogs and derivatives, enzymes, antibodies, portion or fragments of antibodies; an extract made from biological materials such as bacteria, plants, fungi, or animal cells or tissues; naturally occurring or synthetic compositions; and any combinations thereof.

Exemplary potassium ion ionophores include, but are not limited to, valinomycin, crown ethers, e.g., dimethyldibenzo-30-crown-10, dicyclohexyl-18-crown, dimethyldicyclohexyl-18-crown-6, tetraphenyl borate, tetrakis(chlorophenyl)borate. Sodium ion ionophores include, for example, methyl monensin, N,N',N"-triheptyl-N,N',N"trimethyl-4,4', 4"-propylidintris-(3-oxabutyramide), N,N,N,N'-tetracyclohexyl-1,2-phenylenedioxydiacetamide, 4-octadecanoyloxymethyl-N,N,N',N'-tetracyclohexyl-1,2-phenylenedioxydiacetamide, bis [(12-crown-4)methyl] dodecylmethylmalonate. Exemplary calcium ion ionophores include, but are not limited to, bis(didecylphosphate), bis (4-octylphenylphosphate), bis(4-(1, 1,3,3-tetramethylbutyl) phenylphosphate tetracosamethylcyclododecasiloxane, N,N'-di(1,1,3,3ethoxycarbonyl)undecyl)-N,N',4, 5-tetramethyl-3,6dioxaoctane diamide, calcium ionophore A23187 (also known as C-7522), calcium ionophore II 21193, and calcium ionophore IV 21198. Exemplary barium ion ionophores include, but are not limited to, calcium di(2-ethylhexyl)phosphate+decan-1-ol, barium complex of nonylphenoxypoly(ethyleneoxy)ethanol in ortho-nitrodiphenyl ether. Exemplary chloride ion ionophores include, but are not limited to, {u-[4,5-dimethyl-3,6-bis(octyloxy)-1, 2-phenylene]}bis(trifluoroacetato-0)dimercuri (ETH 9009), {(x-[4,5-dimethyl-3,6-bis(dodecyloxy)-1,2-phenylene]}bis (mercury chloride) (ETH 9033), 5,10,15,20-tetraphenyl21H, 23H-porphin manganese (III) chloride (MnTPPCl), tributyltin chloride (TBTCl) and trioctyltin chloride (TOTCl). Bicarbonate ion ionophores include, for example, quaternary ammonium ion exchanger p-octodecyloxy-meta-chlorophenyl-hydrazone-mesoxalonitrile. Ammonium ion ionophores include, for example, nonactin and monactin. Nitrate ion ionophores include, for example, tridodecylhexadecylammonium nitrate+n-octylortho-nitrophenyl, 1:10 phenanthroline nickel (II) nitrate+ para-nitrocymene. Lithium ion ionophores include, for example, N,N'-diheptyl-N,N',5,5-tetramethyl-3,7-dioxononanediamide), 12-crown-4,6,6-dibenzyl-14-crown-4. Another non-limiting exemplary list of ionophores includes: for potassium, valinomycin, dicyclohexano-18-crown-6, dibenzo-18-crown-6, tetraphenyl borate, tetrakis (chlorophenyl) borate; for calcium, bis(didecylphosphate), bis(4-octylphenylphosphate), bis(4-(1,1,3,3-tetramethylbutyl) phenylphosphate tetracosamefhylcyclododecasiloxane, N, N'-di(ll-ethoxycarbonyl) undecyl)-N, N',4,5-tetramethyl-3,6-dioxaoctane diamide; for hydrogen, tridodecylamine, N-methyl N-octadecyl (1-methyl, 2-hydroxy, 2-phenyl) ethylamine, N-octadecyl 3-hydroxy n-propylamine, N, N' bis (octadecyl ethylene amine), p-octadecyloxy-m-chlorophenylhydrazonemeso oxalonitrile; for sodium, monensin, N,N',N"-triheptyl-N, N, N"-trimethyl-4, 4', 4"-propylidintris-(3-oxabutyramide), N,N,N',N'-tetracyclohexyl-1,2-phenylenedioxydiacetamide, 4-octadecanoyloxymethyl-N,N,N',N',-tetracyclohexyl-1,2-phenylenedioxydiacetamide, bis[(12-crown-4)methyl] dodecylmethylmalonate; for lithium, N, N'-diheptyl-N, N, 5,5-tetramethyl-3,7-dioxononanediamide), 12-crown-4, 6,6dibenzyl-14 crown-4; for chloride, quaternary ammonium chloride, tributyl tin chloride. Other suitable ionophores include ionomycin, monensin, lasalocid, laidlomycin, and the like Ion Channel Modulators As used herein, the term "ion-channel modulator" refers to a compound that modulates at least one activity of an ion-channel. The term "ion-channel modulator" as used herein is intended to include agents that interact with the channel pore itself, or that may act as an allosteric modulator of the channel by interacting with a site on the channel complex. The term "ion-channel modulator" as used herein is also intended to include agents that modulate activity of an ion-channel indirectly. By "indirectly," as used in reference to modulator interactions with ion-channel, means the ion-channel modulator does not directly interact with the ion-channel itself, i.e., ion-channel modulator interacts with the ion-channel via an intermediary. Accordingly, the term "indirectly" also encompasses the situations wherein the ion-channel modulator requires another molecule in order to bind or interact with the ion-channel.

Without limitations, an ion-channel modulator can be selected from the group consisting of small or large organic or inorganic molecules; monosaccharides; disaccharides; trisaccharides; oligosaccharides; polysaccharides; biological macromolecules, e.g., proteins, peptides, peptide analogs and derivatives thereof, peptidomimetics, nucleic acids, nucleic acid analogs and derivatives, enzymes, antibodies, portion or fragments of antibodies; an extract made from biological materials such as bacteria, plants, fungi, or animal cells or tissues; naturally occurring or synthetic compositions; and any combinations thereof.

In some embodiments of the aspects described herein, the ion-channel modulator modulates the passage of ions through the ion-channel.

In some embodiments of the aspects described herein, the modulator is an inhibitor or antagonist of the ion-channel. As used herein, the term "inhibitor" refers to compounds which inhibit or decrease the flow of ions through an ion-channel.

In some embodiments of the aspects described herein, the modulator is an agonist of the ion-channel. As used herein, the term "agonist" refers to compounds which increase the flow of ions through an ion-channel.

In some embodiments of the aspects described herein, the modulator modulates at least one activity of the ion-channel by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

In some embodiments of the aspects described herein, at least one activity of the ion-channel is inhibited or lowered by at least 5%, at least 10%, at least 15%, at least 20%, at least 25%, at least 30%, at least 40%, at least 50%, at least 60%, at least 70%, at least 80%, at least 90%, at least 95%, at least 98%, or 100% (e.g. complete loss of activity) relative to control with no modulator.

In some embodiments of the aspects described herein, the ion-channel modulator has an $IC_{50}$ of less than or equal to 500 nM, 250 nM, 100 nM, 50 nM, 10 nM, 1 nM, 0.1 nM, 0.01 nM or 0.001 nM.

In some embodiments of the aspects described herein, the ion-channel modulator inhibits the flow of ions through the ion-channel by at least 5%, at least 10%, at least 15%, at least 20%, at least 25%, at least 30%, at least 40%, at least 50%, at least 60%, at least 70%, at least 80%, at least 90%, at least 95%, at least 98%, or 100% (e.g. complete stop of ion flow through the channel) relative to a control with no modulator.

In some embodiments of the aspects described herein, the ion-channel modulator increases the flow of ions through the ion-channel by at least 5%, at least 10%, at least 15%, at least 20%, at least 25%, at least 30%, at least 40%, at least 50%, at least 60%, at least 70%, at least 80%, at least 90%, at least 100%, at least 1.5 fold, at least by 2-fold, at least 3-fold, at least 4-fold, or at least 5-fold or more relative to a control with no modulator.

In some embodiments of the aspects described herein, the ion-channel modulator increases concentration of ions, e.g. sodium, in a cell by at least 5%, at least 10%, at least 15%, at least 20%, at least 25%, at least 30%, at least 40%, at least 50%, at least 60%, at least 70%, at least 80%, at least 90%, at least 100%, at least 1.5 fold, at least by 2-fold, at least 3-fold, at least 4-fold, or at least 5-fold or more relative to a control with no modulator.

Without wishing to be bound by a theory, an ion-channel modulator can modulate the activity of an ion-channel through a number of different mechanisms. For example, a modulator can bind with the ion-channel and physically block the ions from going through the channel. An ion-channel modulator can bring about conformational changes in the ion-channel upon binding, which may increase or decrease the interaction between the ions and the channel or may increase or decrease channel opening.

A modulator can modulate the energy utilizing activity, e.g. ATPase activity, of the ion-channel. In some embodiments of the aspects described herein, the ion-channel modulator inhibits the ATPase activity of the ion-channel.

In some embodiments of the aspects described herein, an ion-channel modulator inhibits ATPase activity of the $Na^+$/$K^+$-ATPase by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 98%, or 100% (complete inhibition) relative to a control without the modulator. Without wishing to be bound by theory, ATPase activity can be measured by measuring the dephosphorylation of adenosine-triphosphate by utilizing methods well known to the skilled artisan for measuring such dephosphorylation reactions.

In some embodiments of the aspects described herein, an ion-channel modulator inhibits RIG-I activation by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 98%, or 100% (complete inhibition) relative to a control without the modulator.

In some embodiments of the aspects described herein, an ion-channel modulator inhibits ATPase activity of RIG-I by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 98%, or 100% (complete inhibition) relative to a control without the modulator.

Without limitation, the ion-channel modulator can be a small organic molecule, small inorganic molecule, a polysaccharide, a peptide, a protein, a nucleic acid, an extract made from biological materials such as bacteria, plants, fungi, animal cells, animal tissue, and any combinations thereof.

In some embodiments of the aspects described herein, the ion-channel modulator is a cardiac glycoside. As used herein, the term "cardiac glycoside" refers to the category of compounds that have a positive inotropic effect on the heart. Cardiac glycosides are also referred to as cardiac steroids in the art. They are used in treatment of heart diseases, including cardiac arrhythmia and have a rate dependent effect upon AV nodal conduction. As a general class of compounds, cardiac glycosides comprise a steroid core with either a pyrone or butenolide substituent at C17 (the "pyrone form" and "butenolide form"). Additionally, cardiac glycosides may optionally be glycosylated at C3. The form of cardiac glycosides without glycosylation is also known as "aglycone." Most cardiac glycosides include one to four sugars attached to the 3R—OH group. The sugars most commonly used include L-rhamnose, D-glucose, D-digitoxose, D-digitalose, D-digginose, D-sarmentose, L-vallarose, and D-fructose. In general, the sugars affect the pharmacokinetics of a cardiac glycoside with little other effect on biological activity. For this reason, aglycone forms of cardiac glycosides are available and are intended to be encompassed by the term "cardiac glycoside" as used herein. The pharmacokinetics of a cardiac glycoside may be adjusted by adjusting the hydrophobicity of the molecule, with increasing hydrophobicity tending to result in greater absorption and an increased half-life. Sugar moieties may be modified with one or more groups, such as an acetyl group.

A large number of cardiac glycosides are known in the art. Exemplary cardiac glycoside include, but are not limited to, bufalin, ouabain, digitoxigenin, digoxin, lanatoside C, Strophantin K, uzarigenin, desacetyllanatoside A, digitoxin, actyl digitoxin, desacetyllanatoside C, strophanthoside, scillarenin, scillaren A, proscillaridin, proscillaridin A, BNC-1, BNC-4, digitoxose, gitoxin, strophanthidiol, oleandrin, acovenoside A, strophanthidine digilanobioside, strophanthidin-d-cymaroside, digitoxigenin-L-rhamnoside, digitoxigenin theretoside, strophanthidin, strophanthidine, strophanthidine digilanobioside, strophanthidin-Dcymaroside, digoxigenin, digoxigenin 3,12-diacetate, gitoxigenin, gitoxigenin 3-acetate, gitoxigenin 3,16-diacetate, 16-acetyl gitoxigenin, acetyl strophanthidin, ouabagenin, 3-epigoxigenin, neriifolin, acetylneriifolin cerberin, theventin, somalin, odoroside, honghelin, desacetyl digilanide, calotropin, calotoxin, lanatoside A, uzarin, strophanthidine-3β-digitoxoside, strophanthidin a-L-rhamnopyranoside, and analogs, derivatives, pharmaceutically acceptable salts, and/or prodrugs thereof.

More than a hundred cardiac glycosides have been identified as secondary metabolites in plants, with most belonging to the angiosperms. See for example, Melero, C. P., Medardea, M. & Feliciano, A. S. A short review on cardiotonic steroids and their aminoguanidine analogues. Molecules 5, 51-81 (2000), content of which is herein incorporated by reference. Generally, cardiac glycosides are found in a diverse group of plants including *Digitalis purpurea* and *Digitalis lanata* (foxgloves), *Nerium oleander* (common oleander), *Thevetia peruviana* (yellow oleander), *Convallaria majalis* (lily of the valley), *Urginea maritima* and *Urginea indica* (squill), and *Strophanthus gratus* (ouabain). Recently, however, cardiac glycosides of the bufadienolide class were identified in the skin and the carotid gland of animals, and mainly in the venom of several toad species. See Steyn, P. S. & van Heerden, F. R. Bufadienolides of plant and animal origin. Nat. Prod. Rep. 15, 397-413 (1998), content of which is herein incorporated by reference.

In some embodiments of the aspects described herein, the ion-channel modulator is a sodium pump blocker. As used herein, the terms "sodium pump blocker," "sodium pump inhibitor," and "sodium pump antagonist" refer to compounds that inhibit or block the flow of sodium and/or potassium ions across a cell membrane.

In some embodiments of the aspects described herein, the ion-channel modulator is a calcium channel blocker. As used herein, the terms "calcium channel blocker," "calcium channel inhibitor," and "calcium channel antagonist" refer to compounds that inhibit or block the flow of calcium ions across a cell membrane. Calcium channel blockers are also known as calcium ion influx inhibitors, slow channel blockers, calcium ion antagonists, calcium channel antagonist drugs and as class IV antiarrhythmics. Exemplary calcium channel blocker include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil, verapamil, and analogs, derivatives, pharmaceutically acceptable salts, and/or prodrugs thereof.

In some embodiments of the aspects described herein, the calcium channel blocker is a beta-blocker. Exemplary beta-blockers include, but are not limited to, Alprenolol, Bucindolol, Carteolol, Carvedilol (has additional α-blocking activity), Labetalol, Nadolol, Penbutolol, Pindolol, Propranolol, Timolol, Acebutolol, Atenolol, Betaxolol, Bisoprolol, Celiprolol, Esmolol, Metoprolol, Nebivolol, Butaxamine, and ICI-118,551 (3-(isopropylamino)-1-[(7-methyl-4-indanyl)oxy]butan-2-ol), and analogs, derivatives, pharmaceutically acceptable salts, and/or prodrugs thereof.

Exemplary $K^+$ ion-channel modulators include, but are not limited to, 2,3-Butanedione monoxime; 3-Benzidino-6-(4-chlorophenyl)pyridazine; 4-Aminopyridine; 5-(4-Phenoxybutoxy)psoralen; 5-Hydroxydecanoic acid sodium salt; L-α-Phosphatidyl-D-myo-inositol; 4,5-diphosphate, dioctanoyl; Aa1; Adenosine 5'-(β,γ-imido)triphosphate tetralithium salt hydrate; Agitoxin-1; Agitoxin-2; Agitoxin-3; Alinidine; Apamin; Aprindine hydrochloride; BDS-I; BDS-II; BL-1249; BeKm-1; CP-339818; Charybdotoxin; Charybdotoxin; Chlorzoxazone; Chromanol 293B; Cibenzoline succinate; Clofilium tosylate; Clotrimazole; Cromakalim; CyPPA; DK-AH 269; Dendrotoxin-I; Dendrotoxin-K; Dequalinium chloride hydrate; DPO-1 needles; Diazoxide; Dofetilide; E-4031; Ergtoxin; Glimepiride; Glipizide; Glybenclamide; Heteropodatoxin-2; Hongotoxin-1; ICA-105574; IMID-4F hydrochloride; Iberiotoxin; Ibutilide hemifumarate salt; Isopimaric Acid; Kaliotoxin-1; Levcromakalim; Lq2; Margatoxin; Mast Cell Degranulating Peptide; Maurotoxin; Mephetyl tetrazole; Mepivacaine hydrochloride; Minoxidil; Minoxidil sulfate salt; N-Acetylprocainamide hydrochloride; N-Salicyloyltryptamine; NS 1619; NS1643; NS309; NS8593 hydrochloride; Nicorandil; Noxiustoxin; Omeprazole; PD-118057; PNU-37883A; Pandinotoxin-Kα; Paxilline; Penitrem A; Phrixotoxin-2; Pinacidil monohydrate; Psora-4; Quinine; Quinine hemisulfate salt monohydrate; Quinine hydrobromide; Quinine hydrochloride dehydrate; Repaglinide; Rutaecarpine; S(+)-Niguldipine hydrochloride; SG-209; Scyllatoxin; Sematilide monohydrochloride monohydrate; Slotoxin; Stromatoxin-1; TRAM-34; Tamapin; Tertiapin; Tertiapin-Q trifluoroacetate salt; Tetracaine; Tetracaine hydrochloride; Tetraethylammonium chloride; Tityustoxin-Kα; Tolazamide; UCL 1684; UCL-1848 trifluoroacetate salt; UK-78282 monohydrochloride; VU 590 dihydrochloride hydrate; XE-991; ZD7288 hydrate; Zatebradine hydrochloride; α-Dendrotoxin; β-Dendrotoxin; δ-Dendrotoxin; γ-Dendrotoxin; β-Bungarotoxin; and analogs, derivatives, pharmaceutically acceptable salts, and/or prodrugs thereof.

In some embodiments of the aspects described herein, the ion-channel modulator is a potassium channel agonist. As used herein, a "potassium channel agonist" is a $K^+$ ion-channel modulator which facilitates ion transmission through $K^+$ ion-channels. Exemplary potassium channel agonists include, but are not limited to diazoxide, minoxidil, nicorandil, pinacidil, retigabine, flupirtine, lemakalim, L-735534, and analogs, derivatives, pharmaceutically acceptable salts, and/or prodrugs thereof.

In some embodiments of the aspects described herein, the ion-channel modulator is selected from the group consisting of bufalin; digoxin; ouabain; nimodipine; diazoxide; digitoxigenin; ranolazine; lanatoside C; Strophantin K; uzarigenin; desacetyllanatoside A; actyl digitoxin; desacetyllanatoside C; strophanthoside; scillaren A; proscillaridin A; digitoxose; gitoxin; strophanthidiol; oleandrin; acovenoside A; strophanthidine digilanobioside; strophanthidin-d-cymaroside; digitoxigenin-L-rhamnoside; digitoxigenin theretoside; strophanthidin; digoxigenin-3,12-diacetate; gitoxigenin; gitoxigenin 3-acetate; gitoxigenin-3,16-diacetate; 16-acetyl gitoxigenin; acetyl strophanthidin; ouabagenin; 3-epigoxigenin; neriifolin; acetyhieriifolin cerberin; theventin; somalin; odoroside; honghelin; desacetyl digilanide; calotropin; calotoxin; convallatoxin; oleandrigenin; periplocyrnarin; strophanthidin oxime; strophanthidin semicarbazone; strophanthidinic acid lactone acetate; ernicyrnarin; sannentoside D; sarverogenin; sarmentoside A; sarmentogenin; proscillariditi; marinobufagenin; Amiodarone; Dofetilide; Sotalol; Ibutilide; Azimilide; Bretylium; Clofilium; N-[4-[[1-[2-(6-Methyl-2-pyridinyl)ethyl]-4-piperidinyl]carbonyl]phenyl]methanesulfonamide (E-4031); Nifekalant; Tedisamil; Sematilide; Ampyra; apamin; charybdotoxin; 1-Ethyl-2-benzimidazolinone (1-EBIO); 3-Oxime-6,7-dichloro-1H-indole-2,3-dione (NS309); Cyclohexyl-[2-(3,5-dimethyl-pyrazol-1-yl)-6-methyl-pyrimidin-4-yl]-amine (CyPPA); GPCR antagonists; ifenprodil; glibenclamide; tolbutamide; diazoxide; pinacidil; halothane; tetraethylammonium; 4-aminopyridine; dendrotoxins; retigabine; 4-aminopyridine; 3,4-diaminopyridine; diazoxide; Minoxidil; Nicorandi; Retigabine; Flupirtine; Quinidine; Procainamide; Disopyramide; Lidocaine; Phenytoin; Mexiletine; Flecainide; Propafenone; Moricizine; atenolol; ropranolol; Esmolol; Timolol; Metoprolol; Atenolol; Bisoprolol; Amiodarone; Sotalol; Ibutilide; Dofetilide; Adenosine; Nifedipine; δ-conotoxin; κ-conotoxin; ω-conotoxin; ω-conotoxin; ω-conotoxin GVIA; ω-conotoxin ω-conotoxin CNVIIA; ω-conotoxin CVIID; ω-conotoxin AM336; cilnidipine; L-cysteine derivative 2A; ω-agatoxin IVA; N,N-dialkyl-dipeptidyl-amines; SNX-111 (Ziconotide); caffeine; lamotrigine; 202W92 (a structural analog of lamotrigine); phenytoin; carbamazepine; 1,4-dihydro-2,6-dimethyl-5-nitro-4-[thieno[3,2-c]-pyridin-3-yl]-3-pyridinecarboxylic acid, 1-phenylethyl ester; 1,4-dihydro-2,6-dimethyl-5-nitro-4-[thieno[3,2-c]-pyridin-3-yl]-3-pyridinecarboxylic acid, 1-methyl-2-propynyl ester; 1,4-dihydro-2,6-dimethyl-5-nitro-4-[3,2-c]pyridin-3-yl]-3-pyridinecarboxylic acid, cyclopropylmethyl ester; 1,4-dihydro-2,6-dimethyl-5-nitro-4-[thieno(3,2-c)pyridin-3-yl]-3-pyridinecarboxylic acid, butyl ester; (S)-1,4-Dihydro-2,6-dimethyl-5-nitro-4-[thieno[3,2c]pyridin-3-yl]-3-pyridinecarboxylic acid, 1-methylpropyl ester; 1,4-Dihydro-2,6-dimethyl-5-nitro-4-thieno[3,2-c]pyridin-3-yl]-3-pyridinecarboxylic acid, methyl ester; 1,4-Dihydro-2,6-dimethyl-5-nitro-4-[thieno[3,2-c]pyridin-3-yl]-3-pyridinecarboxylic acid, 1-methylethyl ester; 1,4-Dihydro-2,6-dimethyl-5-nitro-4-[thieno[3,2-c]pyridin-3-yl]-3-pyridinecarboxylic acid, 2-propynyl ester; 1,4-Dihydro-2,6-dimethyl-5-nitro-4-[thieno[3,2-c]pyridin-3-yl]-3-pyridinecarboxylic acid, 1-methyl-2propynyl ester; 1,4-Dihydro-2,6-dimethyl-5-nitro-4-[thieno[3,2-c]pyridin-3-yl]-3-pyridinecarboxylic acid, 2-butynyl este; 1,4-Dihydro-2,6-dimethyl-5-nitro-4-[thieno[3,2-c]pyridin-3-yl]-3-pyridinecarboxylic acid, 1-methyl-2butynyl este; 1,4-Dihydro-2,6-dimethyl-5-nitro-4-[thieno[3,2-c]pyridin-3-yl]-3-pyridinecarboxylic acid, 2,2-dimethylpropyl ester; 1,4-Dihydro-2,6-dimethyl-5-nitro-4-thieno[3,2-c]pyridin-3-yl]-3-pyridinecarboxylic acid, 3-butynyl ester; 1,4-Dihydro-2,6-dimethyl-5-nitro-4-[thieno3,2-c]pyridin-3-yl]-3-pyridinecarboxylic acid, 1,1-dimethyl-2propynyl ester; 1,4-Dihydro-2,6-dimethyl-5-nitro-4-[thieno3,2-c]pyridin-3-yl-3-pyridinecarboxylic acid, 1,2,2-trimethylpropyl ester; R(+)-1,4-Dihydro-2,6-dimethyl-5-nitro-4[thieno[3,2-c]pyridin-3-yl]-3-pyridinecarboxylic (2Amethyl-1-phenylpropyl) ester; S-(−)-1,4-Dihydro-2,6-dimethyl-5-nitro-4[thieno[3,2-c]pyridin-3-yl]-3-pyridinecarboxylic acid, 2-methyl-1-phenylpropyl ester; 1,4-Dihydro-2,6-dimethyl-5-nitro-4-[thieno[3,2c]-pyridin-3-yl]-3-pyridinecarboxylic acid, 1-methylphenylethyl ester; 1,4-Dihydro-2,6-dimethyl-5-nitro-4-[thieno[3,2-c]-pyridin-3-yl]-3-pyridinecarboxylic acid, 1-phenylethyl ester; 1,4-Dihydro-2,6-dimethyl-5-nitro-4-[thieno[3,2c]-pyridin-3-yl]-3-pyridinecarboxylic acid, (1-phenylpropyl)ester; 1,4-Dihydro-2,6-dimethyl-5-nitro-4-[thieno[3,2c]-pyridin-3-yl]-3-pyridinecarboxylic acid, (4-methoxyphenyl)methyl ester; 1,4-Dihydro-2,6-dimethyl-5-nitro-4-[thieno[3,2c]-pyridin-3-yl]-3-pyridinecarboxylic acid, 1-methyl-2phenylethyl ester; 1,4-Dihydro-2,6-dimethyl-5-nitro-4-[thieno[3,2c]-pyridin-3-yl]-3-pyridinecarboxylic acid, 2-phenylpropyl ester; 1,4-Dihydro-2,6-dimethyl-5-nitro-4-[thieno[3,2c]-pyridin-3-yl]-3-pyridinecarboxylic acid, phenylmethyl ester; 1,4-Dihydro-2,6-dimethyl-5-nitro-4-[thieno[3,2c]-pyridin-3-yl]-3-pyridinecarboxylic acid, 2-phenoxyethyl ester; 1,4-Dihydro-2,6-dimethyl-5-nitro-4-thieno3,2-c]pyridin-3-yl]-3-pyridinecarboxylic acid, 3-phenyl-2propynyl este; 1,4-Dihydro-2,6-dimethyl-5-nitro-4-[thieno[3,2c]-pyridin-3-yl]-3-pyridinecarboxylic acid, 2-methoxy2-phenylethyl ester; (S)-1,4-Dihydro-2,6-dimethyl-5-nitro-4-[thieno[3,2-c]pyridin-3-yl]-3-pyridinecarboxylic acid, 1phenylethyl este; (R)-1,4-Dihydro-2,6-dimethyl-5-nitro-4-[thieno[3,2-c]pyridin-3-yl]-3-pyridinecarboxylic acid, 1phenylethyl este; 1,4-Dihydro-2,6-dimethyl-5-nitro-4-[thieno[3,2c]-pyridin-3-yl]-3-pyridinecarboxylic acid, cyclopropylmethyl ester; 1,4-Dihydro-2,6-dimethyl-5-nitro-4-thieno[3,2-c]pyridin-3-yl]-3-pyridinecarboxylic acid, 1-cyclopropylethyl este; 1,4-Dihydro-2,6-dimethyl-5-nitro-4-[thieno[3,2c]-pyridin-3-yl]-3-pyridinecarboxylic acid, 2-cyanoethyl ester; 1,4-Dihydro-4-(2-{5-[4-(2-methoxyphenyl)-1-1piperazinyl]pentyl}-3-furanyl)-2,6-dimethyl-5-nitro3-pyridinecarboxylic acid, methyl ester; 4-(4-Benzofurazanyl)-1,4-dihydro-2,6-dimethyl-5-nitro-3-pyridinecarboxylic acid, {4-[4-(2-methoxyphenyl)-1-piperazinyl]butyl} ester; 1,4-Dihydro-2,6-dimethyl-5-nitro-4-(3-pyridinyl)-3-pyridinecarboxylic acid, {4-[4-(2-pyrimidinyl)-1-piperazinyl]butyl} ester; 4-(3-Furanyl)-1,4-dihydro-2,6-dimethyl-5-nitro-3pyridinecarboxylic acid, {2-[4-(2-methoxyphenyl)-1piperazinyl]ethyl} ester; 4-(3-Furanyl)-1,4-dihydro-2,6-dimethyl-5-nitro-3pyridinecarboxylic acid, {2-[4-(2-pyrimidinyl)-1piperazinyl]ethyl} ester; 1,4-Dihydro-2,6-dimethyl-4-(1-methyl-1H-pyrrol-2-yl)-5-nitro-3-pyridinecarboxylic acid, {4-[4-(2-methoxyphenyl) 1-piperazinyl]butyl} ester; 1,4-Dihydro-2,6-dimethyl-4-(1-methyl-1H-pyrrol-2yl)-5-nitro-3-pyridinecarboxylic acid, {4-[4-(2pyrimidinyl)-1-piperazinyl]butyl} ester; 1,4-Dihydro-2,6-dimethyl-5-nitro-4-(3-thienyl)-3-pyridinecarboxylic acid, {2-[4-(2-methoxyphenyl)-1-piperazinyl]ethyl} ester; 1,4-Dihydro-2,6-dimethyl-5-nitro-4-(3-thienyl)-3-pyridinecarboxylic acid, {2-[4-(2-pyrimidinyl)-1-piperazinyl]ethyl} ester; 4-(3-Furanyl)-1,4-dihydro-2,6-dimethyl-5-nitro-3-pyridinecarboxylic acid, {4-[4-(2-pyrimidinyl)-1-piperazinyl]butyl} ester; (4-(2-Furanyl)-1,4-dihydro-2,6-dimethyl-5-nitro-3-pyridinecarboxylic acid, {4-[4-(2-pyrimidinyl)-1-piperazinyl]butyl} ester; 1,4-Dihydro-2,6-dimethyl-5-nitro-4-(2-thienyl)-3-pyridinecarboxylic acid, {2-[4-(2-methoxyphenyl)-1-piperazinyl]ethyl} ester; 1,4-Dihydro-2,6-dimethyl-4-(1-methyl-1H-pyrrol-2-yl)-5-nitro-3-pyridinecarboxylic acid, {2-[4-(2methoxyphenyl)-1-piperazinyl]ethyl} ester; 1,4-Dihydro-2,6-dimethyl-4-(1-methyl-1H-pyrrol-2-yl)-5-nitro-3-pyridinecarboxylic acid, {2-[4-(2pyrimidinyl) 1-piperazinyl]ethyl} ester; 5-(4-Chlorophenyl)-N-(3,5-dimethoxyphenyl)-2-furancarboxamide (A-803467); and analogs, derivatives, pharmaceutically acceptable salts, and/or prodrugs thereof.

In some embodiments of the aspects described herein, the ion-channel modulator is bufalin or analogs, derivatives, pharmaceutically acceptable salts, and/or prodrugs thereof. Exemplary bufalin analogs and derivatives include, but are not limited to, 7β-Hydroxyl bufalin; 3-epi-7β-Hydroxyl bufalin; 1β-Hydroxyl bufalin; 15α-Hydroxyl bufalin; 15β-Hydroxyl bufalin; Telocinobufagin (5-hydroxyl bufalin); 3-epi-Telocinobufagin; 3-epi-Bufalin-3-O-β-d-glucoside; 1 IP-Hydroxyl bufalin; 12β-Hydroxyl bufalin; 1β,7β-Dihydroxyl bufalin; 16α-Hydroxyl bufalin; 7β,16α-Dihydroxyl bufalin; 1β,12β-Dihydroxyl bufalin; resibufogenin; norbufalin; 3-hydroxy-14(15)-en-19-norbufalin-20,22-dienolide; 14-dehydrobufalin; bufotalin; arenobufagin; cinobufagin; marinobufagenin; proscillaridin; scillroside; scillarenin; and 14,15-epoxy-bufalin. Without limitation, analogs and derivatives of bufalin include those that can cross the blood-brain barrier. Herein, bufadienolides and analogs and derivatives thereof are also considered bufalin analogs or derivatives thereof. Further bufalin or bufadienolide analogs and derivatives amenable to the present invention include those described in U.S. Pat. Nos. 3,080,362; 3,136,753; 3,470,240; 3,560,487; 3,585,187; 3,639,392; 3,642,770; 3,661,941; 3,682,891; 3,682,895; 3,687,944; 3,706,727; 3,726,857; 3,732,203; 3,80,6502; 3,812,106; 3,838,146; 4,001,401; 4,102,884; 4,175,078; 4,242,33; 4,380,624; 5,314,932; 5,874,423; and 7,087,590 and those described in Min, et al., *J. Steroid. Biochem. Mol. Biol.*, 91(1-2): 87-98 (2004); Kamano, Y. & Pettit, G. R. *J. Org. Chem.*, 38 (12): 2202-2204 (1973); Watabe, et al., *Cell Growth Differ,* 8(8): 871 (1997); and Mahringer et al., *Cancer Genomics and Proteomics,* 7(4): 191-205 (2010). Content of all of the patents and references listed in the above paragraphs is herein incorporated by reference.

Adenosine Receptor Modulators

As used herein, the term "adenosine receptor modulator" refers to a compound that modulates at least one activity of an adenosine receptor. The term "adenosine receptor modulator" as used herein is intended to include agents that interact with the adenosine receptor itself, or that can act as an allosteric modulator of the receptor by interacting with a site on the channel complex. The term "adenosine receptor modulator" as used herein is also intended to include agents that modulate activity of an adenosine receptor indirectly. By "indirectly," as used in reference to modulator interactions with adenosine receptor, means the modulator does not directly interact with the receptor itself, i.e., modulator interacts with the receptor via an intermediary. Accordingly, the term "indirectly" also encompasses the situations wherein the modulator requires another molecule in order to bind or interact with the receptor.

Adenosine receptors are proteins found in animals and humans that can bind the ligand, adenosine, causing a physiological response. Adenosine receptors have been located in a variety of tissues and cells, including hippocampus, adipocytes, atrioventricle node, striatum, platelets, neutrophils, coronary vasculature and olfactory tubercule.

Four adenosine receptors are commonly referred to as A1, A2A, A2B, and A3. The stimulation of A1 receptors, among other things, can inhibit nerve cells, lower heart rate, slowAV nodal conduction, and promote vasoconstriction. The stimulation of A2A receptors is generally anti-inflammatory, and can be used to sense excessive tissue inflammation, and promote coronary vasodilatation. The stimulation of A2B generally promotes vasodilatation. The stimulation of A3 receptors, among other things, can both stimulate and inhibit cell growth, and promote tumor growth and angiogenesis. Numerous documents describe the current knowledge on adenosine receptors. These include Bioorganic & Medicinal Chemistry, 6, (1998), 619-641, Bioorganic & Medicinal Chemistry, 6, (1998), 707-719, J. Med. Chem., (1998), 41, 2835-2845, J. Med. Chem., (1998), 41, 3186-3201, J. Med. Chem., (1998), 41, 2126-2133, J. Med. Chem., (1999), 42, 706-721, J. Med. Chem., (1996), 39, 1164-1171, Arch. Pharm. Med. Chem., 332, 39^1, (1999), Am. J. Physiol., 276, H1113-1116, (1999) and Naunyn Schmied, Arch. Pharmacol. 362, 375-381, (2000), content of all of which is incorporated herein by reference.

As used herein, the term "modulate" refers to a change or alternation in at least one biological activity of the adenosine receptor. Modulation can be an increase or a decrease in activity, a change in binding characteristics, or any other change in the biological, functional, or immunological properties of the receptor. Ligands that bind to the adenosine receptor causing the inhibition of the adenosine receptor physiological response are termed adenosine receptor antagonists. Likewise, ligands that bind to the adenosine receptor, thereby generating a physiological response that mimics the response caused by the adenosine receptor binding adenosine, are termed adenosine receptor agonists.

In some embodiments of the aspects described herein, the modulator is an agonist of the adenosine receptor. It will be appreciated that the adenosine receptor agonists include compounds which act both directly and indirectly on the receptor resulting in activation of the receptor, or mimic the action of the receptor having the same net effect.

In some embodiments of the aspects described herein, the modulator modulates at least one activity of the receptor by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

In some embodiments of the aspects described herein, at least one activity of the receptor is increased by at least 5%, at least 10%, at least 15%, at least 20%, at least 25%, at least 30%, at least 40%, at least 50%, at least 60%, at least 70%, at least 80%, at least 90%, at least 95%, at least 98%, or 100% relative to a control with no modulator.

Exemplary adenosine receptor modulators include, but are not limited to, 2-(1-Hexynyl)-N-methyladenosine; 2-Cl-IB-MECA; 2'-MeCCPA; 5'-N-ethylcarboxamido adenosine; 8-Cyclopentyl-1,3-dimethylxanthine (CPX); 8-Cyclopentyl-1,3-dipropylxinthine (DPCPX); 8-Phenyl-1,3-dipropylxanthine; ATL-146e; BAY 60-6583; Caffeine; CCPA; CF-101 (IB-MECA); CGS-21680; CP-532,903; CVT-6883; GR 79236; istradefylline; LUF-5835; LUF-5845; MRE3008F20; MRS-1191; MRS-1220; MRS-1334; MRS-1523; MRS-1706; MRS-1754; MRS-3558; MRS-3777; N6-Cyclopentyladenosine; PSB 36; PSB-0788; PSB-10; PSB-11; PSB-1115; PSB-603; Regadenoson; SCH-442,416; SCH-58261; SDZ WAG 994; theophylline; VUF-5574; ZM-241,385; and the like.

Exemplary agonists of adenosine receptor agonists include, but are not limited to, GR 79236; SDZ WAG 994; ATL-146e; CGS-21680; Regadenoson; 5'-N-ethylcarboxamidoadenosine; BAY 60-6583; LUF-5835; LUF-5845; 2-(1-Hexynyl)-N-methyladenosine; CF-101 (IB-MECA); 2-Cl-IB-MECA; CP-532,903; MRS-3558; N6-cyclopentyladenosine (CPA), N-ethylcarboxamido adenosine (NECA), 2-[p-(2-carboxyethyl)phenethyl-amino-5'-N-ethylcarboxamido adenosine (CGS-21680); 2-chloroadenosine; N6-[2-(3, 5-demethoxyphenyl)-2-(2-methoxyphenyl]ethyladenosine; 2-chloro-N6-cyclopentyladenosine (CCPA); 2'-MeCCPA; N-(4-aminobenzyl)-9-[5-(mefhylcarbonyl)-beta-D-robofuranosyl]adenine (AB-MECA); ([IS-[1a,2b,3b,4a(S*)]]-4-[7-[[2-(3chloro-2-thienyl)-1-methyl-propyl]amino]-3H-imidazole[4, 5-b]pyridyl-3-yl]cyclopentane carboxamide (AMP579); N6-(R)-phenylisopropyladenosine (R-PLA); aminophenylethyladenosine 9APNEA) and cyclohexyladenosine (CHA); N-[3-(R)-tetrahydrofuranyl]-6-aminopurine riboside (CVT510); CVT-2759; allosteric enhancers such as PD81723; N6-cyclopentyl-2-(3-phenylaminocarbonyltriazene-1-yl)adenosine (TCPA); 2-amino-3-naphthoylthiophenes78; and the like.

In some embodiments, the adenosine receptor agonist can be N6-cyclopentyladenosine

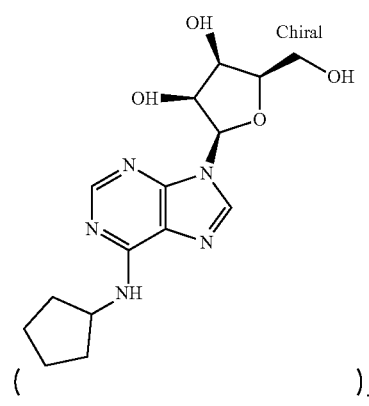

Gamma-Secretase Ligands

As used herein, the term "modulate," with reference to the gamma-secretase means to regulate positively or negatively the normal functioning of a gamma-secretase. Thus, the term modulate can be used to refer to an increase, decrease, masking, altering, overriding or restoring the normal functioning of a gamma-secretase. A gamma-secretase modulator can be a gamma-secretase agonist or a gamma-secretase antagonist.

In some embodiments of the aspects described herein, the modulator modulates at least one activity of the gamma-secretase by at least 5%, at least 10%, at least 15%, at least 20%, at least 25%, at least 30%, at least 40%, at least 50%, at least 60%, at least 70%, at least 80%, at least 90%, or at least 95%, at least 98% or more relative to a control with no modulation.

As used herein, the terms "gamma-secretase protein" and "gamma-secretase" refer to a protein that exhibits gamma-secretase activity which includes: recognizing a polypeptide substrate having a gamma-secretase cleavage sequence; and catalyzing cleavage of the gamma-secretase cleavage sequence, at the gamma-secretase cleavage site, to produce substrate cleavage products.

Gamma-secretase is a macromolecular proteolytic complex composed of at least four proteins: presenilin (PS), nicastrin (NCT), PEN-2 and APH-1 (De Strooper, 2003, Neuron 38:9-12). Recently, CD147 and TMP21 have been found to be associated with the gamma-secretase complex (Chen, et al., 2006, Nature 44011208-1212; Zhou et al., 2005, Proc. Natl. Acad. Sci. USA, 102:7499-7504). Among these known components, PS is believed to contain the active site of gamma-secretase, recognized as an aspartyl protease (Esler et al., 2000, Nat. Cell. Biol., 2:428:434; Li et al., 2000, Nature 4051689-694; Wolfe et al., 1999, Nature 3981513-517). Considerable effort has been made to understand the process of gamma-secretase substrate recognition and its catalytic machinery. A PS-dependent protease can process any singlepass transmembrane (TM) protein regardless of its primary sequence as long as the TM protein extracellular domain is smaller than 300 amino acids. Moreover, the size of the extracellular domain appears to determine the efficiency of substrate cleavage (Struhl and Adachi, 2000, Mol. Cell 6:625636).

Exemplary gamma-secretase inhibitors include, but are not limited to, those described in U.S. Patent Application Publication Nos. US2003/0216380; US2006/0009467; US2004/0048848; US2004/0171614; US2005/0085506; US2006/0100427; US2005/0261495; US2007/0299053; US2006/0264417; US2006/0258638; US2005/0245501; US2003/0134841; US2008/004,5533; US2007/0213329; US2006/0041020; US2004/016404; and US2003/0114496, U.S. Pat. Nos. 7,122,675; 6,683,091; 7,208,602; 7,256,186; 6,967,196; 7,304,056; 7,304,055; 7,101,870; 6,962,913; 6,794,381; 7,304,094; and 6,984,663, and PCT Publication Nos. WO03/013527; WO03/066592; WO00/247671; WO00/050391; WO00/007995; and WO03/018543, content of all of which is incorporated herein by reference. Additional exemplary gamma secretase modulators include certain nonsteroidal anti-inflammatory drugs (NSAIDs) and their analogs as described in U.S. Patent Publication No. US 2002/0128319, PCT Publication No. WO01/78721, and Weggen et al., Nature, 414 (2001) 212-16; Morihara et al., J. Neurochem., 83 (2002), 1009-12; and Takahashi et al., J. Biol. Chem., 278 (2003), 18644-70), content of all of which is incorporated herein by reference.

In some embodiments, the gamma-secretase modulator inhibits binding of a substrate by at least about or about any one of 10%, 20%, 30%, 40%, 50%, 60%, 70%, 80%, 90%, 95% or 100% relative to a control. Binding of a substrate to a gamma-secretase can be determined by any method known to one of skill in the art.

In some embodiments, the gamma-secretase modulator reduces an activity of a gamma-secretase by at least 5%, at least 10%, at least 20%, at least 30%, at least 40%, at least 50%, at least 60%, at least 70%, at least 80%, at least 90%, at least 95%, at least 98%, or 100% (e.g. complete loss of activity) relative to an uninhibited control.

In some embodiments, the gamma-secretase modulator enhances an activity of a gamma-secretase by at least 5%, 10%, 20%, 30%, 40%, 50%, 50%, 70%, 80%, 90%, 1-fold, 1.1-fold, 1.5-fold, 2-fold, 3-fold, 4-fold, 5-fold or more relative to an unactivated control.

In some embodiments, the gamma-secretase modulator is capable of binding to the active site of a GPCR (e.g., a binding site for a substrate).

In some embodiments, the serotonin receptor modulator is capable of binding to an allosteric site of a gamma-secretase.

In some embodiments of this and other aspects described herein, the GPCR antagonist has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

In some embodiments of this and other aspects of the invention, the GPCR agonist has an EC50 of less than or equal to 500 nM, 250 nM, 100 nM, 50 nM, 10 nM, 1 nM, 0.1 nM, 0.01 nM or 0.001 nM.

Corticosteroids

As used herein, the term "corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

Without limitations, a corticosteroid can be selected from the group consisting of small or large organic or inorganic molecules; monosaccharides; disaccharides; trisaccharides; oligosaccharides; polysaccharides; biological macromolecules, e.g., proteins, peptides, peptide analogs and derivatives thereof, peptidomimetics, nucleic acids, nucleic acid analogs and derivatives, enzymes, antibodies, portion or fragments of antibodies; an extract made from biological materials such as bacteria, plants, fungi, or animal cells or tissues; naturally occurring or synthetic compositions; and any combinations thereof.

Exemplary corticosteroids include, but are not limited to, aldosternone, beclomethasone, beclomethasone dipropionate, betametahasone, betametahasone-21-phosphate disodium, betametahasone valerate, budesonide (also referred to as Bud herein), clobetasol, clobetasol propionate, clobetasone butyrate, clocortolone pivalate, cortisol, cortisteron, cortisone, dexamethasone, dexamethasone acetate, dexamethasone sodium phosphate, diflorasone diacetate, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate.

As used herein, the term corticosteroid is intended to include the following generic and brand name corticosteroids: cortisone (CORTONE ACETATE, ADRESON, ALTESONA, CORTELAN, CORTISTAB, CORTISYL, CORTOGEN, CORTONE, SCHEROSON); dexamethasone-oral (DECADRON-ORAL, DEXAMETH, DEXONE, HEXADROL-ORAL, DEXAMETHASONE INTENSOL, DEXONE 0.5, DEXONE 0.75, DEXONE 1.5, DEXONE 4); hydrocortisone-oral (CORTEF, HYDROCORTONE); hydrocortisone cypionate (CORTEF ORAL SUSPENSION); methylprednisolone-oral (MEDROL-ORAL); prednisolone-oral (PRELONE, DELTA-CORTEF, PEDIAPRED, ADNISOLONE, CORTALONE, DELTACORTRIL, DELTASOLONE, DELTASTAB, DIADRESON F, ENCORTOLONE, HYDROCORTANCYL, MEDISOLONE, METICORTELONE, OPREDSONE, PANAAFCORTELONE, PRECORTISYL, PRENISOLONA, SCHERISOLONA, SCHERISOLONE); prednisone (DELTASONE, LIQUID PRED, METICORTEN, ORASONE 1, ORASONE 5, ORASONE 10, ORASONE 20, ORASONE 50, PREDNICEN-M, PREDNISONE INTENSOL, STERAPRED, STERAPRED DS, ADASONE, CARTANCYL, COLISONE, CORDROL, CORTAN, DACORTIN, DECORTIN, DECORTISYL, DELCORTIN, DELLACORT, DELTADOME, DELTACORTENE, DELTISONA, DIADRESON, ECONOSONE, ENCORTON, FERNISONE, NISONA, NOVOPREDNISONE, PANAFCORT, PANASOL, PARACORT, PARMENISON, PEHACORT, PREDELTIN, PREDNICORT, PREDNICOT, PREDNIDIB, PREDNIMENT, RECTODELT, ULTRACORTEN, WINPRED); triamcinoloneoral (KENACORT, ARISTOCORT, ATOLONE, SHOLOG A, TRAMACORT-D, TRI-MED, TRIAMCOT, TRISTOPLEX, TRYLONE D, U-TRI-LONE).

Other exemplary corticosteroid drugs include cortisone, Cortisol, hydrocortisone (1103, 17-dihydroxy, 21-(phosphonooxy)-pregn-4-ene, 3,20-dione disodium), dihydroxycortisone, dexamethasone (21-(acetyloxy)-9fluoro-β,17-dihydroxy-16α-methylpregna-1,4-diene-3,20-dione), and highly derivatized steroid drugs such as beconase (beclomethasone dipropionate, which is 9-chloro11(3,17,21, trihydroxy-16β-methylpregna-1,4diene-3,20-dione 17,21-dipropionate). Other examples of corticosteroids include flunisolide, prednisone, prednisolone, methylprednisolone, triamcinolone, deflazacort and betamethasone.

In some embodiments, the corticosteroid can be Budesonide

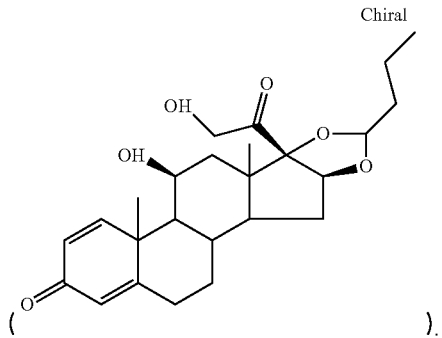

Synergistic Effect

The inventors have also discovered that many of the hit compounds have a synergistic effect on satellite cell proliferation when given together with a growth factor. Accordingly, in some embodiments of the aspects described herein, a compound described herein is contacted with the satellite cell along with a growth factor. Exemplary growth factors include, but are not limited to, basic epidermal growth factor (bEGF), fibroblast growth factors (FGF), FGF-1, FGF-2 (bFGF), FGF-4, thymosins, platelet-derived growth factors (PDGF), insulin binding growth factors (IGF), IGF-1, IGF-2, epidermal growth factor (EGF), transforming growth factor (TGF), TGF-alpha, TGF-beta, cartilage inducing factors-A and —B, osteoid-inducing factors, osteogenin, bone morphogenic proteins, and other bone growth factors, collagen growth factors, heparin-binding growth factor-1 or -2, and their biologically active derivatives.

The term "synergistic" as used herein is defined to mean a combination of components wherein the activity of the combination is greater than the additive of the individual activities of each component of the combination. In some embodiments, the activity of the combination is at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 50-fold, at least 100-fold or greater than the additive of the individual activities of each component of the combination.

The compound and the growth factor can be contacted with the satellite cell in any ratio. The ratio can be a mole:mole ratio or a weight:weight ratio For example, the ratio can range from 100:1 to 1:100. In some embodiment, proliferation enhancer and the growth factor are in a ratio from 20:1 to 1:20. In some embodiments, the proliferation enhancer and the growth factor are in a ratio from 10:1 to 1:10. In some embodiments, the proliferation enhancer and the growth factor are in a ratio from 5:1 to 1:5. In some embodiments, the proliferation enhancer and the growth factor are in a ratio from 15:1 to 1:5. In some embodiments, the proliferation enhancer and the growth factor are in a ratio from 10:1 to 1:1. In one embodiment, proliferation enhancer and the growth factor are used in a 1:1 ratio.

In some embodiments, the growth factor can be selected from the group consisting of basic epidermal growth factor (bEGF), fibroblast growth factors (FGF), FGF-1, FGF-2 (bFGF), FGF-4, thymosins, platelet-derived growth factors (PDGF), insulin binding growth factors (IGF), IGF-1, IGF-2, epidermal growth factor (EGF), transforming growth factor (TGF), TGF-alpha, TGF-beta, cartilage inducing factors-A and —B, osteoid-inducing factors, osteogenin, bone morphogenic proteins, other bone growth factors, collagen growth factors, heparin-binding growth factor-1 or -2, and their biologically active derivatives.

Synergistic Compositions

As discussed herein, the inventors have discovered, inter alia, that some of the proliferation enhancers show a synergistic effect on satellite cell proliferation when used together with a growth factor. Accordingly, the disclosure also provided synergistic compositions comprising a proliferation enhancer and a growth factor. The growth factor can be selected Without limitations, the proliferation enhancer and the growth factor can be present in any ratio in the synergistic composition, and the ratio can mole:mole or weight:weight. For example, the proliferation enhancer and the growth factor can be in a ratio from 100:1 to 1:100. In some embodiment, proliferation enhancer and the growth factor are in a ratio from 20:1 to 1:20. In some embodiments, the proliferation enhancer and the growth factor are in a ratio from 10:1 to 1:10. In some embodiments, the proliferation enhancer and the growth factor are in a ratio from 5:1 to 1:5. In some embodiments, the proliferation enhancer and the growth factor are in a ratio from 15:1 to 1:5. In some embodiments, the proliferation enhancer and the growth factor are in a ratio from 10:1 to 1:1. In one embodiment, proliferation enhancer and the growth factor are used in a 1:1 ratio. In some embodiments, the proliferation enhancer and the growth factor can in a ratio of 50:1, 40:1, 30:1, 25:1, 20:1, 15:1, 10:1, 5:1, 3:1, 2:1, 1:1.75, 1.5:1, or 1.25:1 to 1:1.25, 1:1.5, 1.75, 1:2, 1:3, 1:4, 1:5, 1:10, 1:15, 1:20, 1:20, 1:30, 1:40, or 1:50.

Contacting of Satellite Cells with Compounds

The satellite cell population can be contacted with the proliferation enhancer in a cell culture e.g., in vitro or ex vivo, or the proliferation enhancer can be administrated to a subject, e.g., in vivo. In some embodiments of the invention, a proliferation enhancer described herein can be administrated to a subject for repairing or regenerating a damaged muscle tissue.

The term "contacting" or "contact" as used herein in connection with contacting a population of satellite cells includes subjecting the satellite cells to an appropriate culture media which comprises the indicated compound or agent. Where the satellite cell population is in vivo, "contacting" or "contact" includes administering the proliferation enhancer or agent in a pharmaceutical composition to a subject via an appropriate administration route such that the proliferation enhancer or agent contacts the satellite cell population in vivo.

For in vivo methods, a therapeutically effective amount of a compound described herein can be administered to a subject. Methods of administering compounds to a subject are known in the art and easily available to one of skill in the art. Promoting satellite cell proliferation in a subject can lead to treatment, prevention or amelioration of a number of diseases, disorders or conditions which are caused by a damaged muscle tissue.

Satellite cells suitable for use in ex vivo methods can be obtained from subject according to methods well known to those skilled in the art.

The term "ex vivo" refers to cells which are removed from a living organism and cultured outside the organism (e.g., in a test tube). For ex vivo methods, satellite cells can include autologous satellite cells, i.e., a cell or cells taken from a subject who is in need of treatment for muscle damage or repair. Autologus satellite cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., Transplantation Immunology, Bach and Auchincloss, Eds. (Wiley, John & Sons, Incorporated 1994).

Without wishing to be bound by theory any suitable cell culture media can be used for ex vivo methods of the invention. For example, inventors have discovered that the cells can survive in minimum of 10% serum medium. While the cells can survive in suspension culture with at least 30% serum, they may need to be adherent when medium with 10% serum is used in absence of bFGF. Cells are optimal in cultures when they are adherent on laminin. After ex vivo contact with a compound described herein, when the satellite cells have reached a desired population number or density, e.g., about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, or more cells, the cells can be transplanted in a subject who is in need of treatment for muscle repair or damage. The cells can be transplanted in a subject from whom the cells were originally obtained or in different subject.

When the satellite cells are contacted with a proliferation enhancer, the proliferation enhancer can have a direct or an indirect affect on the satellite cells. As used herein, a "direct affect" means that the proliferation enhancer is directly interacting with the satellite cells, e.g., binding to a cell surface receptor on the satellite cell, taken up into the satellite cells. As used herein, an "indirect affect" means that the proliferation enhancer does not directly interacts with the satellite cell. For example, the proliferation enhancer can interact with a non-satellite cell and indirectly influence the proliferation of satellite cell. Without wishing to be bound by theory, the proliferation enhancer can indirectly influence a satellite cell by inducing expression and/or secretion of a molecule from a non-satellite cell, and this molecule then directly or indirectly influencing the proliferation of satellite cells.

As used herein, the term "damaged muscle tissue" refers to a muscle tissue, such as a skeletal or cardiac muscle that has been altered for instance by a physical injury or accident, disease, infection, over-use, loss of blood circulation, or by genetic or environmental factors. A damaged muscle tissue can be a dystrophic muscle or an ageing muscle. Exemplary symptoms of muscle damage include, but are not limited to, swelling, bruising or redness, open cuts as a consequence of an injury, pain at rest, pain when specific muscle or the joint in relation to that muscle is used, weakness of the muscle or tendons, and an inability to use the muscle at all.

In some embodiments of this and other aspects described herein, the damaged muscle tissue results from muscle atrophy/wasting.

In some embodiments of this and other aspects described herein, the damaged muscle tissue results from sarcopenia. As used herein, the term "sarcopenia" refers to the loss of muscle mass and function that inevitably occurs with aging. Sarcopenia is responsible for decreased levels of physical activity which, in turn, can result in increased body fat and a further loss of muscle. Loss of muscle mass results from a negative net balance between muscle protein synthesis and muscle protein breakdown. The etiology of this loss of skeletal muscle mass and function is not believed to be clear. Reduced levels of physical activity, loss of motor units secondary to changes in the central nervous system, and inadequate protein intake have all been implicated In some embodiments of this and other aspects described herein, the damaged muscle tissue results from a physical injury.

In some embodiments of this and other aspects of the invention, the damaged muscle is skeletal muscle.

In some embodiments, the subject has or is otherwise affected by muscle injury, insult or disease.

In some embodiments of this and other aspects described herein, disease resulting in damaged muscle tissue is a myopathy. Without limitation, myopathy can be a congenital myopathy or an acquired myopathy. Exemplary myopathies include, but are not limited to, dystrophies, myotonia (neuromytonia), congenital myopathies (e.g., nemaline myopathy, multi/minicore myopathy, centronuclear myopathy (or myotubular myopathy)), mitochondrial myopathies, familial periodic paralysis, inflammatory myopathies, metabolic myopathies (e.g., glycogen storage disease and lipid storage disorder), dermatomyositis, polymyositis inclusion body myositis, myositis ossificans, rhabdomyolysis and myoglobinuirias.

In some embodiments of this and other aspects described herein, myopathy is a dystrophy selected from the group consisting of muscular dystrophy, Duchenne muscular dystrophy, Becker's muscular dystrophy, Reflex sympathetic dystrophy, Retinal dystrophy, Conal dystrophy, Myotonic dystrophy, Corneal dystrophy, and any combinations thereof.

Congenital myopathy is a term sometimes applied to hundreds of distinct neuromuscular disorders that may be present at birth, but it is usually reserved for a group of rare inherited primary muscle disorders that cause hypotonia and weakness at birth or during the neonatal period and, in some cases, delayed motor development later in childhood. Patients suffer from weakness ranging from mild (late childhood onset and ability to walk through adulthood) to severe (respiratory insufficiency and death within the first year of life).

The most common types of congenital myopathy are nemaline myopathy, myotubular myopathy, central core myopathy, congenital fiber type disproportion, and multicore myopathy. They are distinguished primarily by their histological features, symptoms, and prognosis. Diagnosis is indicated by characteristic clinical findings and confirmed by muscle biopsy.

In certain embodiments, a therapeutically effective amount of a compound described herein can be administered to a subject to treat any disease in which small muscles (e.g., sphincter muscles) are affected. In certain embodiments, a therapeutically effective amount of a compound described herein can be administered to a subject to treat esophageal diseases (e.g., esophageal reflux disease and other diseases resulting from the loss of esophageal muscle control, tone or motility). In certain embodiments, a therapeutically effective amount of a compound described herein can be administered to a subject to treat urinary incontinence. In certain embodiments, a therapeutically effective amount of a compounds described herein can be administered to a subject to treat fecal incontinence. In certain aspects, a therapeutically effective amount of a compound contemplated herein may be administered to a subject to increase or improve sphincter muscle tone.

X-Linked Myotubular myopathy (XLMTM): Myotubular myopathy is autosomal or X-linked. The more common autosomal variation produces mild weakness and hypotonia in both sexes. The X-linked variation affects males and results in severe skeletal muscle weakness and hypotonia, facial weakness, impaired swallowing, and respiratory muscle weakness and respiratory failure. However, female carriers rarely express significant clinical symptoms. Most patients die within the first year of life from respiratory failure. Some patients survive for several years and may show spontaneous improvement of respiratory function after birth. XLMTM has also been referred to as CNM, MTMX, X-linked centronuclear myopathy, and XMTM in the art.

The characteristic muscle histopathology consists of small rounded muscle fibers with centrally located nuclei surrounded by a halo devoid of contractile elements but containing mitochondria. The MTM1 gene is mutated in vast majority of XLMTM patients. This gene is ubiquitously expressed and shows a muscle-specific alternative transcript due to the use of a different polyadenylation signal. Over one hundred thirty-three different disease associated mutations have been described in the MTM1 gene. A list of MTM1 mutations is maintained on the web at the Human Gene Mutation Database under entry for XLMTM and can be accessed at the following address: uwcm.ac.uk/uwcm/mg/search/119439. Mutations in the MTM1 gene are widespread throughout the gene, although more have been found in exon 4, 12, 3, 8, 9, and 11, in that order when comparing the number of mutations to the nucleotide-length ratio for each exon. For a review of MTM1 mutations in X-Linked Myotubular Myopathy see J. Laporte et al. 2000, 15:393-409.

Mutations in the MTM1 gene include missense, nonsense, small insertions or deletions, large deletions and splice-site mutations. Most point mutations are truncating; however about 25% of the mutations are missense. While most truncating and splice mutations are associated with a severe phenotype, some missense mutations are associated with milder or less severe phenotype and prolonged survival.

Nemaline myopathy: Nemaline myopathy can be autosomal dominant or recessive and result from various mutations on different chromosomes. Nemaline myopathy may be severe, moderate, or mild in neonates. Severely affected patients may experience weakness of respiratory muscles and respiratory failure. Moderate disease produces progressive weakness in muscles of the face, neck, trunk, and feet, but life expectancy may be nearly normal. Mild disease is nonprogressive, and life expectancy is normal.

Central core myopathy: Inheritance is autosomal dominant. Most affected patients develop hypotonia and mild proximal muscle weakness as neonates. Many also have facial weakness. Weakness is nonprogressive, and life expectancy is normal. However, patients are at higher risk of developing malignant hyperthermia (the gene associated with central core myopathy is also associated with increased susceptibility to malignant hyperthermia).

Congenital fiber type disproportion: Congenital fiber type disproportion is inherited, but the pattern is poorly understood. Hypotonia and weakness of the face, neck, trunk, and limbs are often accompanied by skeletal abnormalities and dysmorphic features. Most affected children improve with age, but a small percentage develops respiratory failure.

Multicore myopathy: Multicore myopathy is usually autosomal recessive but may be autosomal dominant. Infants typically present with proximal weakness, but some children present later with generalized weakness. Progression is highly variable.

In some embodiments, a method described herein also comprises the step of diagnosing a subject for congenital myopathy before onset of administering a compound described herein. A subject can be diagnosed for congenital myopathy based on the symptoms presented by the subject.

Generally, symptoms of congenital myopathies include, but are not limited to, depressed reflexes, enlarged muscles, difficulty relaxing muscles following contractions, stiff muscles, and rigid muscles. Specific symptoms are described below.

Central core disease is characterized by a mild, non-progressive muscle weakness. Signs of central core disease usually appear in infancy or early childhood and may present even earlier. There may be decreased fetal movements and breech (feet first) presentation in utero. The main features of CCD are poor muscle tone (hypotonia), muscle weakness, and skeletal problems including congenital hip dislocation, scoliosis (curvature of the spine), pes cavus (high-arched feet), and clubbed feet. Children with CCD experience delays in reaching motor milestones and tend to sit and walk much later than those without the disorder. A child with the disease usually cannot run easily, and may find that jumping and other physical activities are often impossible. Although central core disease may be disabling, it usually does not affect intelligence or life expectancy.

People who have central core disease are sometimes vulnerable to malignant hyperthermia (MH), a condition triggered by anesthesia during surgery. MH causes a rapid, and sometimes fatal, rise in body temperature, producing muscle stiffness.

There is variability in age of onset, presence of symptoms, and severity of symptoms in nemaline myopathy (NM). Most commonly, NM presents in infancy or early childhood with weakness and poor muscle tone. In some cases there may have been pregnancy complications such as polyhydramnios (excess amniotic fluid) and decreased fetal movements. Affected children with NM tend to have delays in motor milestones such as rolling over, sitting and walking. Muscle weakness commonly occurs in the face, neck and upper limbs. Over time, a characteristic myopathic face (a long face that lacks expression) develops. Skeletal problems including chest deformities, scoliosis, and foot deformities may develop. In the most severe cases of NM, feeding difficulties and potentially fatal respiratory problems may also occur. In those who survive the first two years of life, muscle weakness tends to progress slowly or not at all.

Typically the X-linked form of MTM (XLMTM) is the most severe of the three forms (X-linked, autosomal recessive, and autosomal dominant). XLMTM usually presents as a newborn male with poor muscle tone and respiratory distress. The pregnancy may have been complicated by polyhydramnios and decreased fetal movements. Of those who survive the newborn period, many will at least partially depend on a ventilator for breathing. Because of the risk of aspiration, many will also have a gastrostomy tube (G-tube). Boys with XLMTM can experience significant delays in achieving motor milestones and may not ever walk independently. They tend to be tall with a characteristic facial appearance (long, narrow face with a highly arched roof of the mouth and crowded teeth). Intelligence is generally not affected. Medical complications that may develop include: scoliosis, eye problems (eye muscle paralysis and droopy eyelids), and dental malocclusion (severe crowding). In XLMTM, other problems including undescended testicles, spherocytosis, peliosis, elevated liver enzymes, and gallstones may occur.

The autosomal recessive and autosomal dominant forms of MTM tend to have a milder course than the X-linked form. The autosomal recessive form can present in infancy, childhood, or early adulthood. Common features include generalized muscle weakness with or without facial weakness and ophthalmoplegia (paralysis of the eye muscles). Although feeding and breathing problems can occur, affected individuals usually survive infancy. Onset of the autosomal dominant form ranges from late childhood through early adulthood. It tends to be the mildest of the three forms of MTM. Unlike the X-linked form of the condition, problems with other organs (such as the liver, kidneys, and gall bladder) haven't been reported with the autosomal recessive and autosomal dominant forms of MTM.

Diagnosis of a congenital myopathy generally includes evaluation of the subject's personal and family history, physical and neurological examinations that test reflexes and strength, and specialized tests. Since there is overlap between the symptoms of a congenital myopathy and other neuromuscular disorders, a number of tests may be performed to help narrow down the diagnosis. Serum CK (creatinine kinase) analysis, EMG (electromyelogram), nerve conduction studies, and muscle ultrasound tend to be of limited value in making this diagnosis. The definitive diagnosis of a congenital myopathy usually relies upon genetic testing and/or muscle biopsy. Also, muscle biopsy can be used to determine a patient's susceptibility to malignant hyperthermia.

X-linked myotubular myopathy: Diagnosis of X-linked MTM is usually made on muscle biopsy. Findings include: centrally located nuclei in muscle fibers that look like myotubules, absence of structures known as myofibrils, and possibly, persistence of certain proteins usually seen in fetal muscle cells. Gene testing detects a mutation (disease-causing gene change) in up to 97-98% of people with the X-linked form. Gene testing can comprise: (i) complete gene sequencing of the MTM1 gene; (ii) mutation screening (scanning) by methods such as single-stranded conformational polymorphism (SSCP) or denaturing gradient high-performance liquid chromatography (DHPLC), followed by sequencing of the abnormal fragments; and (iii) deletion testing. XLMTM can also be diagnosed by measuring levels of myoubilarin. Patients with known MTM1 mutations usually show abnormal myotubularin levels.

Central core disease: The muscle biopsy from a person with CCD typically displays a metabolically inactive "core" or central region that appears blank when stained (tested) for certain metabolic enzymes (proteins) that should be there. These central regions also lack mitochondria, the energy producing "factories" of the cells. Genetic testing for RYR1 mutations is available on a research basis. The same genetic test may be used to determine the presence of the gene change in family members who may have or be at-risk for the disease. For families in which a RYR1 mutation has been found, prenatal diagnosis may be possible using the DNA of fetal cells obtained from chorionic villus sampling (CVS) or amniocentesis.

Nemaline myopathy: The clinical diagnosis of NM is suspected in an infant under age one with muscle weakness and hypotonia (decreased muscle tone). Definitive diagnosis of nemaline myopathy is made by demonstration of nemaline bodies, rod-shaped structures characteristic of this disease, using a specific stain known as "Gomori trichrome" on a muscle biopsy sample. Muscle biopsy may also show predominance of structures known as type I fibers. Genetic testing is available on a clinical basis for one gene, the ACTA1 gene located on the long arm of chromosome 1. About 15% of NM cases are due to mutations in this gene. Prenatal diagnosis is possible for families with known ACTA1 mutations. The DNA of a fetus can be tested using cells obtained from chorionic villus sampling (CVS) or amniocentesis.

Pharmaceutical Compositions

For administration to a subject, the proliferation enhancers can be provided in pharmaceutically acceptable compositions. These pharmaceutically acceptable compositions comprise a therapeutically-effective amount of one or more of the proliferation enhancers, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound described herein which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable satellite cell proliferation or muscle repair or regeneration.

As used herein, the term "repair" refers to a process by which the damages of a muscle tissue are alleviated or completely eliminated. In some embodiments, at least one symptom of muscle tissue damage is alleviated by at least 5%, at least 10%, at least 20%, at least 30%, at least 40%, or at least 50%.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the administered proliferation enhancer (or proliferation enhancer treated satellite cells) being delivered to a specific location as compared to the entire body of the subject, whereas, systemic administration results in delivery of the proliferation enhancer (or proliferation enhancer treated satellite cells) to essentially the entire body of the subject. One method of local administration is by intramuscular injection.

In the context of administering a compound treated cell, the term "administering" also include transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). Skilled artisan is well aware of methods for implanting or transplantation of cells for muscle repair and regeneration, which are amenable to the present invention. See for example, U.S. Pat. No. 7,592,174 and U.S. Pat. Pub. No. 2005/0249731, content of both of which is herein incorporated by reference.

Furthermore, the proliferation enhancers can be formulated in the form of ointments, creams powders, or other formulations suitable for topical formulations. Without wishing to be bound by a theory, these formulations can deliver the proliferation enhancer from skin to deeper muscle tissue. Accordingly, such formulations can comprise one or more agents that enhance penetration of active ingredient through skin. For topical applications, the proliferation enhancer can be included in wound dressings and/or skin coating compositions.

A proliferation enhancer or composition comprising same can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

In certain aspects, the subject does not have or is not otherwise affected by acute myeloid leukemia (AML).

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

A subject can be one who has been previously diagnosed with or identified as suffering from or having a disorder characterized with muscle damage or muscle atrophy/wasting.

A subject can be one who is not currently being treated with a compound described herein.

A subject can be one who has been previously diagnosed with a disease that is being treated with a therapeutic regime comprising compound described herein, wherein the disease is not a disease characterized with muscle damage or muscle atrophy/wasting Accordingly, in some embodiments, the treatment method comprising adjusting the therapeutic regime of the subject such that at least one symptom of muscle damage is reduced. Without limitation, a therapeutic regime can be adjusted by modulating the frequency of administration of the proliferation enhancer and/or by altering the site or mode of administration.

In some embodiments of the aspects described herein, the method further comprising diagnosing a subject for muscle damage or muscle atrophy/wasting before treating the subject for muscle repair or regeneration.

In some embodiments of the aspects described herein, the method further comprising selecting a subject with muscle damage or muscle atrophy/wasting before treating the subject for muscle repair or regeneration.

A compound described herein can be co-administered to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., N.Y.; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments of the aspects described herein, the pharmaceutically active agent is a growth factor. Exemplary growth factors include, but are not limited to, basic epidermal growth factor (bEGF), fibroblast growth factors (FGF), FGF-1, FGF-2 (bFGF), FGF-4, thymosins, platelet-derived growth factors (PDGF), insulin binding growth factors (IGF), IGF-1, IGF-2, epidermal growth factor (EGF), transforming growth factor (TGF), TGF-alpha, TGF-beta, cartilage inducing factors-A and —B, osteoid-inducing factors, osteogenin, bone morphogenic proteins, and other bone growth factors, collagen growth factors, heparin-binding growth factor-1 or -2, and their biologically active derivatives.

The proliferation enhancer and the pharmaceutically active agent can be administered to the subject in the same pharmaceutical composition or in different pharmaceutical compositions (at the same time or at different times). When administrated at different times, the proliferation enhancer and the pharmaceutically active agent can be administered within 5 minutes, 10 minutes, 20 minutes, 60 minutes, 2 hours, 3 hours, 4, hours, 8 hours, 12 hours, 24 hours of administration of the other. When the proliferation enhancer and the pharmaceutically active agent are administered in different pharmaceutical compositions, routes of administration can be different.

The amount of the proliferation enhancer that can be combined with a carrier material to produce a single dosage form will generally be that amount of the proliferation enhancer that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that the proliferation enhancer is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that the proliferation enhancer or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Screening Assays

In yet another aspect, the invention provides for a method of screening for a candidate compound for stimulating or increasing proliferation in a satellite cell population, the method comprising:

(a) contacting a population of satellite cells with a test compound;
(b) assessing satellite proliferation; and
(c) selecting the compound that induces, increases or enhances satellite cell proliferation.

As used herein, the term "test compound" refers to compounds and/or compositions that are to be screened for their ability to induce, stimulate, enhance, or increase satellite cell proliferation. The test compounds can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; antibodies, antibodies fragments, peptidomimetics; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the test compound is a small molecule.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A comprehensive list of compound libraries can be found at broad.harvard.edu/chembio/platform/screening/compound-_libraries/index. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test compounds can be provided free in solution, or may be attached to a carrier, or a solid support, e.g., beads.

A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

In some embodiments, the test compound induces, enhances, or increases satellite cell proliferation by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more relative to an untreated control.

In some embodiments, the step of assessing satellite cell proliferation comprises detecting a satellite cell marker.

In some embodiments, the step of assessing satellite cell proliferation comprises detecting a satellite cell marker and a cell replication marker. A selected test compound can be further limited to the compound where the satellite cell marker and the cell-replication marker co-localize in the same cell.

Increased or enhanced satellite proliferation can be assessed by: (i) increased total number of cells in the culture, as compared to an untreated control; (ii) increased total number of cells expressing at least one satellite cell marker in the culture, as compared to an untreated control; (iii) increased ratio of cells expressing at least one satellite cell marker to the total number of cells in the culture, as compared to an untreated control; (iv) increased number of cells expressing at least one cell-replication marker, as compared to an untreated control; (v) increased ratio of cells expressing at least one cell-replication marker, as compared to an untreated control; or (vi) a combination thereof.

In some embodiments, satellite cell proliferation is assessed via automated image acquisition and analysis using a Cellomics ArrayScan VTI. The acquisition thresholds/parameters are established such that the computer-based calls of replication events are consistent with human-based calls. Such automated image acquisition and analysis allows for high-throughput screening of compounds.

Generally plating density can range from about 10 k cells/well to about 100 k cells/well. In some embodiments, cellular plating density is in the range from about 25 k cells/well to about 75 k cells/well. In one embodiment, cellular plating density is about 60 k cells/well. Generally, at least 75%, 80%, 85%, 90%, 95% or more of the cells are viable at time of plating.

After plating, satellite cells can be allowed to adhere to the surface for a sufficient time, e.g. at least at least 1 hour, 2 hours, 3, hours, 4 hours, 6 hours, 8 hours, 12 hours, 24 hours, 36 hours, 48 hours or more, before contacting with the test compound. In some embodiments, the cells are allowed to adhere for 48 hours before compound treatment. After the cells have been allowed to adhere for a sufficient time, the media can be changed before treatment with compound of interest.

Generally, compounds can be tested at any concentration that can enhance replication of β-cells relative to a control over an appropriate time period. In some embodiments, compounds are tested at concentration in the range of about 0.1 nM to about 1000 mM. Preferably the compound is tested in the range of about 0.1 μM to about 20 μM, about 0.1 μM to about 10 μM, or about 0.1 μM to about 5 μM. In one embodiment, compounds are tested at 1 μM.

The satellite cell population can be maintained at any temperature suitable for satellite cell cultures. In one embodiment, the satellite cells are maintained at a temperature in the range of about 15° C. to about 55° C. In one embodiment, the pancreatic cells are maintained at 37° C.

Generally, the number of satellite cells in the culture can be counted after the satellite cells have been in contact with the test compound for a sufficient time, e.g., at least 1 hour, at least 2 hours, at least 3, hours, at least 4 hours, at least 5 hours, at least 6 hours, at least 7 hours, at least 8 hours, at least 9 hours, at least 10 hours, at least 11 hours, at least 12 hours, at least 24 hours, at least 36 hours, at least 48 hours, at least 5 days, at least 1 week, at least 2 weeks, at least 3 weeks, or more. The cells can be counted manually or by an automated system. Use of an automated system allows for high-throughput screening of compounds.

The inventors have discovered that in some instances prolonged treatment with the proliferation enhancer does not lead to higher satellite cell proliferation as compared to treatment for a shorter period of time. Accordingly, the number of satellite cells in the culture can be counted after the satellite cells have been in contact with the test compound for between 1 hour and seven days. For example, the number of satellite cells in the culture can be counted after the satellite cells have been in contact with the test compound for one, two, three, four, five or six days.

Satellite-cell and replication cell marker detection can be done after the satellite cells are in contact with the test compound for a sufficient time, e.g., at least 1 hour, at least 2 hours, at least 3, hours, at least 4 hours, at least 5 hours, at least 6 hours, at least 7 hours, at least 8 hours, at least 9 hours, at least 10 hours, at least 11 hours, at least 12 hours, at least 24 hours, at least 36 hours, at least 48 hours, at least 5 days, at least 1 week, at least 2 weeks, at least 3 weeks, or more. After marker detection, number of cells expressing cell-replication and/or satellite cell marker can be counted. Marker detection can include the steps of preparing the cells for the appropriate assay, e.g., fixing and/or staining the cells.

In some embodiments, the satellite cell and cell replication marker detection can be done after the satellite cells are in contact with the test compound for 1 hour to about 7 days.

In some embodiments, the satellite cell and cell replication marker detection can be done after the satellite cells are in contact with the test compound for one, two, three, four, five or six days.

In some embodiments, the method comprises additionally selecting the compound that increased the ratio of satellite cells to the total number of cells as compared to an untreated control.

The term "satellite-cell marker" refers to, without limitation, proteins, peptides, nucleic acids, polymorphism of proteins and nucleic acids, splice variants, fragments of proteins or nucleic acids, elements, and other analytes which are specifically expressed or present in satellite cells. Exemplary satellite cell markers include, but are not limited to, PAX7, PAX3, Myf5, MyoD, and desmin. Other markers that can be used include, but are not limited to, beta-integrin 1 and CXCR4. Method of identifying satellite cells is also described in Sherwood et al. (Cell, 2004, 119: 543-554), content of which is incorporated herein by reference.

The terms "cell replication marker" refers to, without limitation, proteins, peptides, nucleic acids, polymorphisma of proteins and nucleic acids, splice variants, fragments of proteins or nucleic acids, elements, and other analytes which are specifically associated with cell proliferation. Additionally, "cell-replication marker", includes enzymatic activity when changes, e.g., increase or decrease, in the enzymatic activity are specifically associated with cell proliferation. Exemplary cell replication markers include, but are not limited to, phosphorylated histone H3 (PH3), Ki-67 protein, phosphorylated MPM-2 antigen, Proliferating Cell Nuclear Antigen (PCNA, a protein that is expressed in the nuclei of cells during the DNA synthesis phase of the cell cycle), phospho-S780-Rb epitope (Jacobberger, J W, et al. Cytometry A (2007), 73A:5-15), Cenp-F (mitosin), class III β-Tubulin, spindal checkpint protine hMad2, phosphorylated myosin light chain kinase, topoisomerase II, Check point kinase 1 (Chk1), Vesicular Monoamine Transporter 2 (VMAT2), loss of cyclin-dependent kinase 1 (Cdk1) kinase activity. Histone H3 can be phosphorylated at Ser28 or Ser10.

Cell replication markers and satellite cell markers can be detected by methods known in the art and easily available to the skilled artisan, for example appropriate ELISA, immunofluorescent, or immunohistochemical assays can be used for detection. MIB-1 is a commonly used monoclonal antibody that detects the Ki-67 protein. It is used in clinical applications to determine the Ki-67 labelling index. Ki-67 ELISA are described in Klein, C L, et al., J. Mater. Sci. Mater. Med. (2000), 11:125-132; Frahm, S O, et al., J. Immunol. Methods (199*0, 211:43-50; and Key G, et al., J. Immunol. Methods (1994), 177:113-117. Phospho-Histone H3 antibodies for detection of phosphorylated Histone H3 are commercially available from Cell Signaling Technology and Millipore. Antibodies against PCNA are commercially available from Sigma Aldrich. Antibodies to MPM-2 antigen are specific for cells in mitosis, recognizes a family of proteins that share a common phosphorylated epitope.

In some embodiments of this and other aspects described herein, the satellite cell can be isolated from a mammal. Methods for isolating cells from a subject are described, for example in Sherwood et al. (Cell, 2004, 119: 543-554), content of which is incorporated herein by reference.

In some embodiments of this and other aspects described herein, the satellite cell can be isolated from a mouse.

A satellite cell can be transformed cell. As used herein, the term "transformed cells" is art recognized and refers to cells which have converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. In general, term "transformed satellite cell" refers to satellite cells which exhibit increased capacity to persist in serial subcultures or increased growth rate in vitro.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic, that features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with, such as a satellite cell population. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

By way of example, in one embodiment, the assay was performed as follow. Satellite cells were harvested from CAG-B-actin-GFP mice, aged 2-4 months old via the FACS isolation method outlined in Sherwood et al 2004 and Cerletti et al 2008. Briefly, all limb muscles and abdominal muscles were harvested from the animals and digested first in a 0.2% collagenase solution, then in a 0.0125% collagenase/0.05% dispase solution. The filtered solution was stained for cell surface markers, and put through FACS. Cells that were negative for Mac1, Sca1 and CD45 and positive for Beta-integrin 1 and CXCR4 were used for the screening assay. Cells were plated directly from the FACS machine at 50 cells/well, into 96-well plates coated with 10 ug/mL laminin (4-6 hours at 37 C, then partially removed). Media for the screen was Ham's F-10 supplemented with 10% heat-inactivated horse serum, 1× penicillin/streptomycin and 1× L-glutamine. Basic FGF (bFGF) was added only to the positive control wells; all other wells received media only. The day of plating was called Day 0. The day after plating, Day 1, compounds were added. All compounds were dissolved in DMSO, and initially tested at 10 uM, 1 uM or 0.1 uM in duplicate. The negative control for each plate was the same concentration of DMSO (no compounds dissolved). Compounds were incubated with the cells until Day 4, with no media change. bFGF was spiked into positive control wells daily. On Day 4, plates were fixed in 4% paraformaldehyde and washed with phosphate buffered saline. Plates were imaged directly on the Opera Confocal imager, since the cells were readily visible from the CAG-EGFP-Beta-actin transgene. An Acapella script was used to count the number of cells in each well. Wells were scored for proliferation based on the cell counts (DMSO-treated wells usually had around 50 cells at the end of the assay, bFGF-treated wells usually had 150-250 cells at the end). Inventors selected compounds as hits if they had cell numbers greater than or equal to one (or, for the second session of screening, three) standard deviation(s) from the DMSO controls. Compounds thus selected were then tested in an initial dose curve, usually concentrations between 20 nM-30 uM commensurate with the concentration flagged as a hit. A compound was active if it was able to cause proliferation to cell numbers at least two standard deviations over the DMSO negative control. Any compounds that were found to be active in the dose curve were re-supplied from the original vendors. Re-supplied compounds were again tested in a dose curve for proliferation ability. Compounds still found to be active were then put in the queue for optimization and characterization.

In another aspect, the invention provides a compound selected by the screening assay described herein. It is to be understood that analogs, derivatives, and isomers of the compounds selected by the screening assays described herein are also claimed herein.

Kits

In another aspect, the invention provides a kit for muscle repair or regeneration. In some embodiments, the kit comprises a compound described herein, e.g., a compound selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, ionophores, ion channel modulators, gamma-secretase modulators, and any combinations thereof. The compound can be pre-formulated into a pharmaceutical formulation for administration or ingredients for formulating into a pharmaceutical formulation can be provided in the kit.

In some embodiments, the kit comprises a compound described herein, wherein the compound is formulated for topical application.

In some embodiments, the kit comprises a population of satellite cells, wherein at least one cell in the population has been pretreated by contacting the cells with a compound described herein.

In addition to the above mentioned components, the kit can include informational material. The informational material can be descriptive, instructional, marketing or other material that relates to the methods described herein and/or the use of the compound for the methods described herein. For example, the informational material describes methods for administering the formulation to a subject. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for an oligonucleotide preparation, and at least another for a carrier compound. The different components can be combined, e.g., according to instructions provided with the kit. The components can be combined according to a method described herein, e.g., to prepare and administer a pharmaceutical composition.

In addition to the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the formulation. In such embodiments, the kit can include instructions for admixing the formulation and the other ingredients, or for using the oligonucleotide together with the other ingredients.

The compound can be provided in any form, e.g., liquid, dried or lyophilized form. It is preferred that the formulation be substantially pure and/or sterile. When the formulation is provided in a liquid solution, the liquid solution preferably is an aqueous solution, with a sterile aqueous solution being preferred. When the formulation is provided as a dried form, reconstitution generally is by the addition of a suitable solvent. The solvent, e.g., sterile water or buffer, can optionally be provided in the kit.

In some embodiments, the kit contains separate containers, dividers or compartments for the formulation and informational material. For example, the formulation can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the formulation. For example, the kit includes a plurality of syringes, ampules, foil packets, or blister packs, each containing a single unit dose of the formulation. The containers of the kits can be air tight and/or waterproof.

Exemplary embodiments of can also be described by one or more of the following numbered paragraphs.

1. A method of increasing satellite cell proliferation, the method comprising: contacting a satellite cell with a compound selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, adenosine receptor agonists, ionophores, ion channel modulators, gamma-secretase modulators, corticosteroids, and any combination thereof.

2. The method of paragraph 1, wherein the compound is selected from the group consisting of small organic or inorganic molecules; saccharines; oligosaccharides; polysaccharides; peptides, proteins, peptide analogs and derivatives; antibodies, antibodies fragments, peptidomimetics; nucleic acids; nucleic acid analogs and derivatives; an extract made from biological materials; naturally occurring or synthetic compositions; and any combination thereof.

3. The method of any of paragraphs 1-2, wherein the compound is a Flt3 kinase, PDGFR/EGFR, Bcr-abl, Jak3, or SRC kinase inhibitor.

4. The method of any of paragraphs 1-3, wherein the compound is selected from the group consisting of a protein kinase inhibitor and a receptor kinase inhibitor.

5. In some embodiments, the kinase inhibitor can be selected from the group

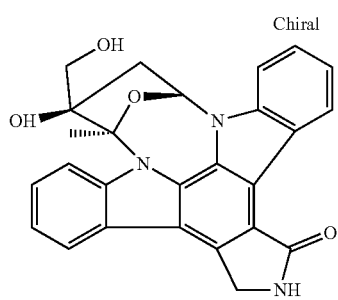

Lestaurtinib (CEP701, ),

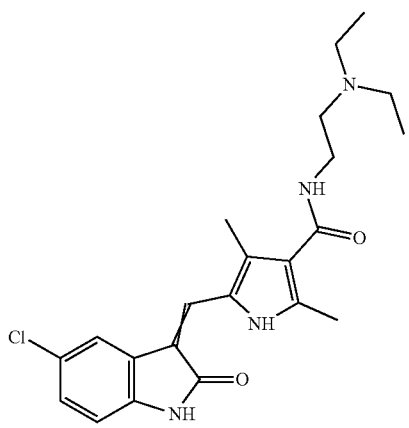

SU11652 ( ),

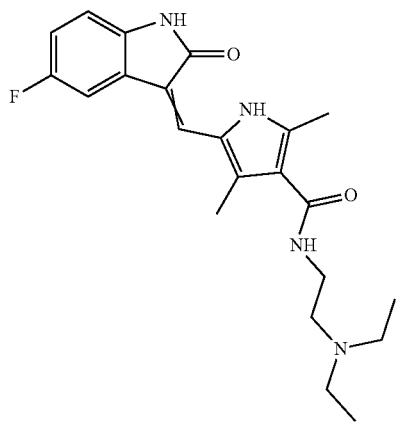

Sunitinib (SU 11248, ),

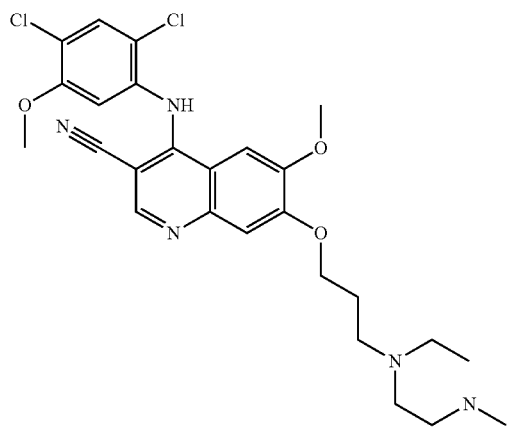

Bosutinib (SKI 606, ),

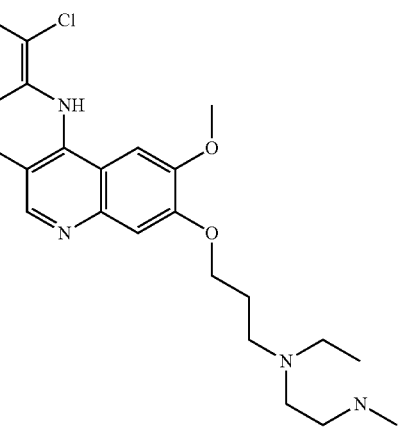

Jak3 Inhibitor VI ( ,

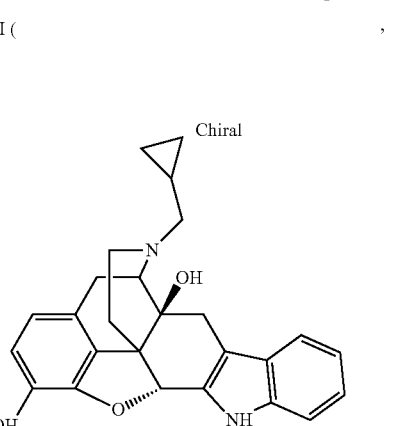

naltrindole ( ),

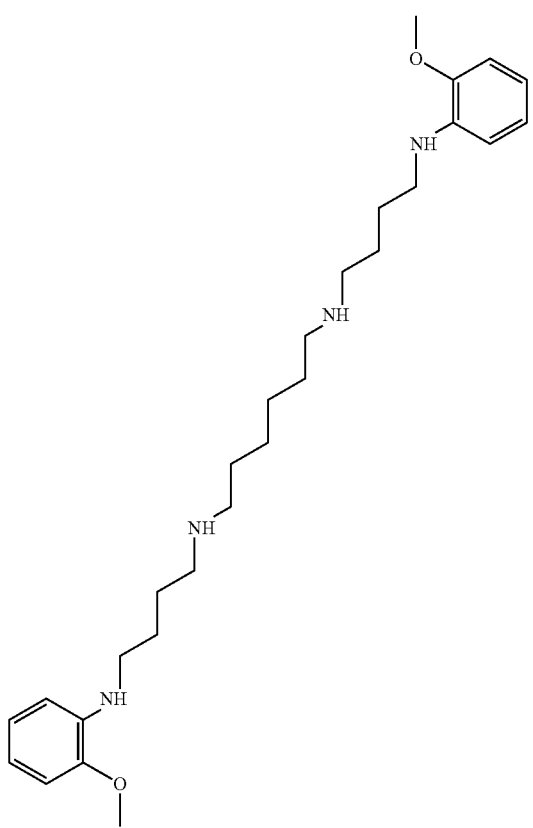

methoctracmine tetrahydrochloride ( ),

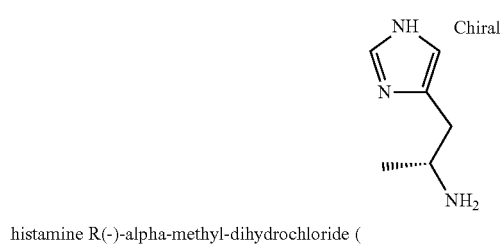

histamine R(-)-alpha-methyl-dihydrochloride ( ),

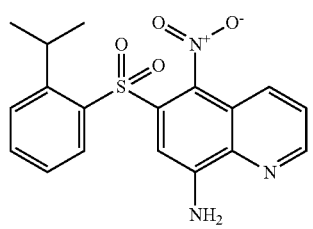

PD160170 ( ),

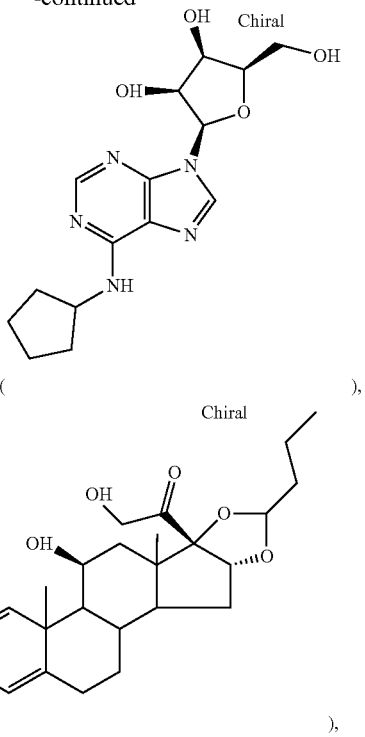

N6-cyclopentyladenosine ( ),

Budesonide ( ), and any combinations thereof.

6. The method of any of paragraphs 1-4, wherein the compound is contacted with the satellite cell at a concentration of about 0.01 nM to about 100 µM.

7. The method of any of paragraphs 1-5, wherein said contacting is for at least 1 hour.

8. The method of any of paragraphs 1-6, wherein said contacting is for one to seven days.

9. The method of any of paragraphs 1-7, wherein the contact is in vitro.

10. The method of any of paragraphs 1-8, wherein the contact is ex vivo.

11. The method of any of paragraphs 1-9, wherein the contact is in vivo.

12. The method of paragraph 10, wherein in vivo contact is in a mammal.

13. The method of paragraph 10 or 11, wherein in vivo contact is in a human.

14. The method of any of paragraphs 10-12, wherein the in vivo contact is in a subject, where the subject is in need of treatment for damaged muscle tissue.

15. The method of paragraph 13, wherein the damaged muscle tissue is the result of a physical injury or accident, disease, infection, over-use, loss of blood circulation, or muscle atrophy or wasting.

16. The method of paragraph 13 or 14, wherein the damaged muscle tissue is dystrophic muscle or an ageing muscle.

17. The method of any of paragraphs 13-15, wherein the damaged muscle tissue is the result of muscle atrophy/wasting.

18. A method for muscle repair or regeneration in a subject, the method comprising administering a therapeutically effective amount of a compound to the subject, which subject has a damaged muscle tissue, and wherein the compound is selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, ionophores, ion channel modulators, gamma-secretase modulators, and any combination thereof.

19. The method of paragraph 17, wherein the damaged muscle tissue is the result of a physical injury or accident, disease, infection, over-use, loss of blood circulation, or muscle atrophy or wasting.

20. The method of any of paragraphs 17-18, wherein the damaged muscle tissue is dystrophic muscle or an ageing muscle.

21. The method of any of paragraphs 17-19, wherein the damaged muscle tissue is the result of muscle atrophy/wasting.

22. The method of any of paragraphs 17-20, wherein the subject is a mammal.

23. The method of any of paragraphs 17-21, wherein the subject is human.

24. The method of any of paragraphs 17-22, wherein the compound is co-administered with a therapeutic agent.

25. The method of paragraph 23, wherein the compound and the therapeutic agent are administered in the same formulation.

26. The method of any of paragraphs 17-24, wherein the compound is administered at a dosage of from 1 μg/kg to 150 mg/kg.

27. The method of any of paragraphs 17-25, wherein said administering is by injection, infusion, instillation, inhalation, or ingestion.

28. The method of any of paragraphs 17-26, wherein said administering is once daily.

29. The method of any of paragraphs 17-27, further comprising diagnosing the subject for muscle damage or muscle atrophy/wasting before treating the subject for muscle repair or regeneration.

30. The method of any of paragraphs 17-28, wherein the compound is selected from the group consisting of

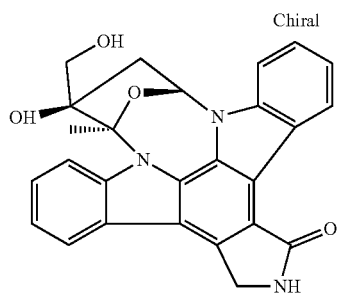

Lestaurtinib (CEP701, ),

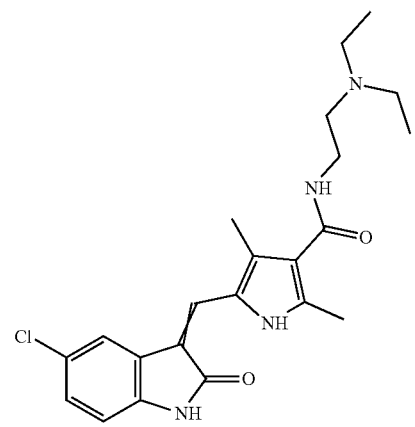

SU11652 ( ),

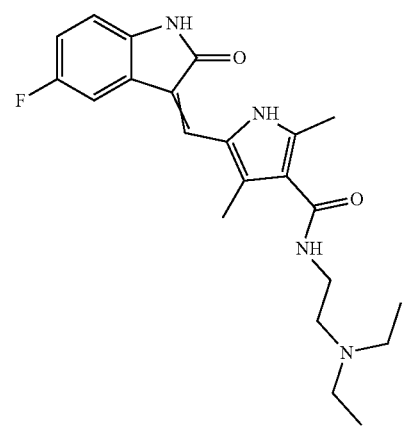

Sunitinib (SU 11248, ),

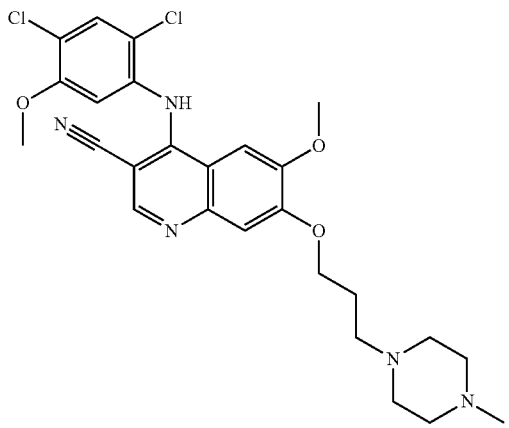

Bosutinib (SKI 606, ),

Jak3 Inhibitor VI (

-continued

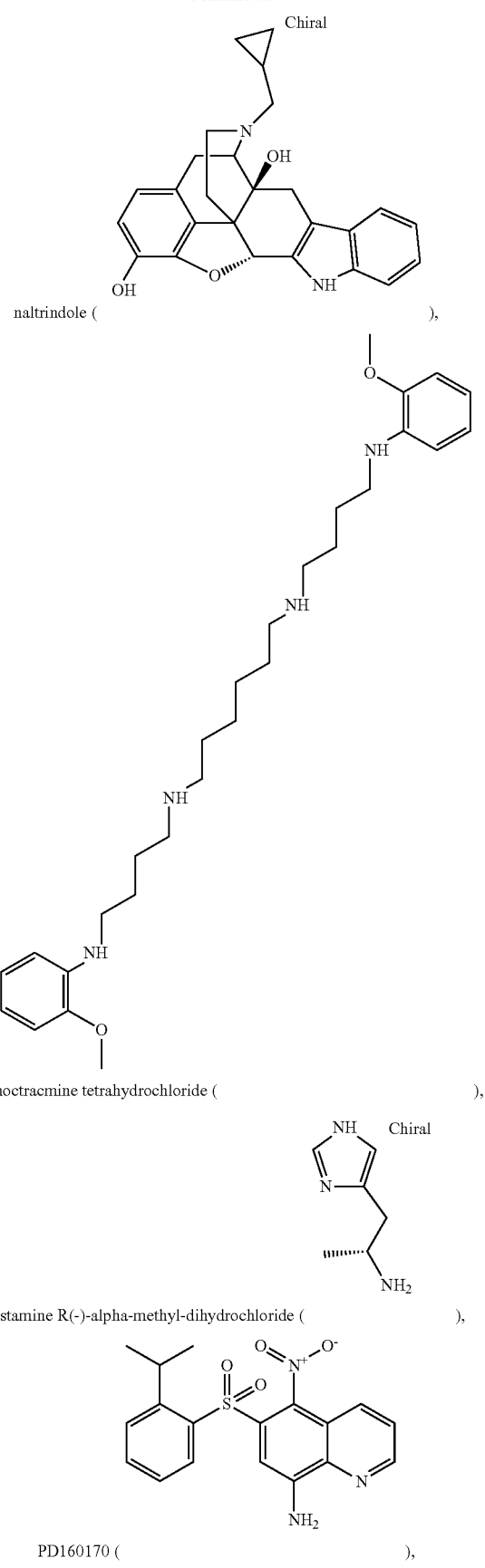

naltrindole ( ), methoctracmine tetrahydrochloride ( ), histamine R(-)-alpha-methyl-dihydrochloride ( ),

PD160170 ( ),

-continued

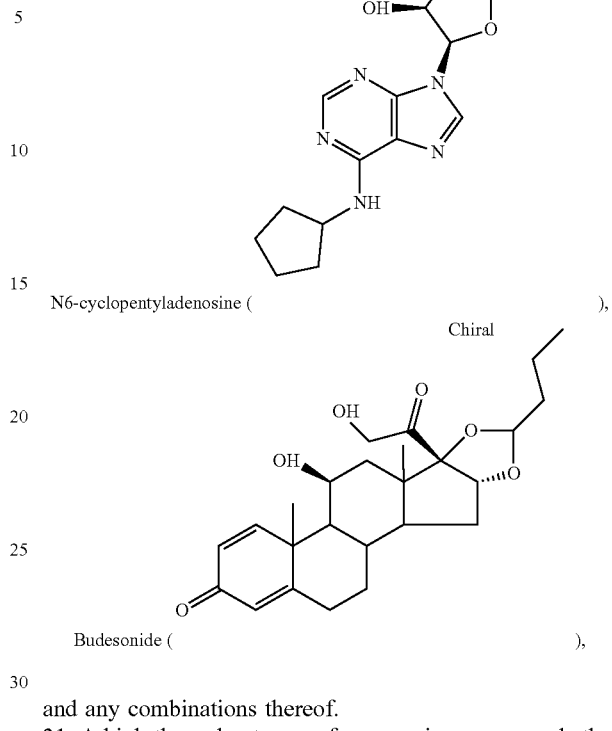

N6-cyclopentyladenosine ( ),

Budesonide ( ), and any combinations thereof.

31. A high throughput assay for screening compounds that induce, stimulate, enhance or increase satellite proliferation, the assay comprising:
   (a) contacting a satellite cell with a test compound;
   (b) assessing satellite cell proliferation; and
   (c) selecting the compound that induces, stimulates, enhances or increases satellite cell replication or growth 32. The assay of paragraph 30, wherein the step of assessing satellite cell proliferation comprises detecting a cell marker.

33. The assay of paragraph 31, wherein the cell marker is selected from the group consisting of CXCR4, β1-integrin, Sca-1, Mac-1, CD45, PAX7, PAX3, Myf5, MyoD, desmin, and any combinations thereof.

34. The assay of any of paragraphs 30-32, wherein the test compound has a concentration in the range of 0.1 nM to 1000 mM.

35. The assay of any of paragraphs 30-33, wherein the assay is performed at a temperature in the range of about 15° C. to about 55° C.

36. The assay of any of paragraphs 30-34, wherein the test compound is contacted with the pancreatic cells for 1 hour to seven days 37. The assay of any of paragraphs 30-35, wherein the test compound increases satellite cell proliferation by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control.

38. The assay of any of paragraphs 30-36, wherein the satellite cells are isolated from a mammal.

39. The assay of any of paragraphs 30-37, wherein the satellite cells are isolated from a subject, where the subject is in need of treatment for damaged muscle tissue.

40. The method of paragraph 38, wherein the damaged muscle tissue is the result of a physical injury or accident, disease, infection, over-use, loss of blood circulation, or muscle atrophy or wasting.
41. The method of paragraph 38 or 49, wherein the damaged muscle tissue is dystrophic muscle or an ageing muscle.
42. The method of any of paragraphs 38-40, wherein the damaged muscle tissue is the result of muscle atrophy/wasting.
43. In some embodiments of any of the foregoing paragraphs 1-42, the kinase inhibitor comprises

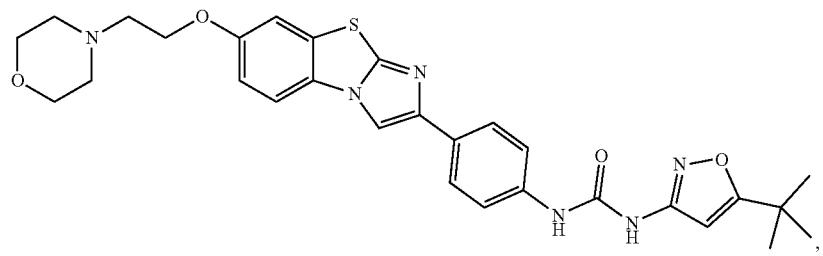

(AC220)

or a salt, ester or chelate thereof.
44. A method of increasing satellite cell proliferation, the method comprising: contacting a satellite cell with a compound, wherein the compound is a kinase inhibitor.
45. The method of paragraph 44, wherein the kinase is a protein kinase.
46. The method of paragraph 44, wherein the protein kinase is a protein tyrosine kinase.
47. The method of paragraph 46, wherein the protein tyrosine kinase is a receptor protein tyrosine kinase.
48. The method of paragraph 47, wherein the receptor protein tyrosine kinase is a member of the RET family.
49. The method of paragraph 47, wherein the receptor protein tyrosine kinase is RET.
50. The method of paragraph 47, wherein the compound interferes with binding of a ligand to the receptor protein tyrosine kinase.
51. The method of paragraph 44, wherein the compound is selected from the group consisting of small organic or inorganic molecules, saccharines, oligosaccharides, polysaccharides, peptides, proteins, peptide analogs and derivatives, antibodies, antibodies fragments, peptidomimetics, nucleic acids, nucleic acid analogs and derivatives, an extract made from biological materials, naturally occurring or synthetic compositions and any combination thereof.
52. The method of paragraph 51, wherein the compound is an antibody.
53. The method of paragraph 44, wherein the compound is contacted with the satellite cell at a concentration of about 0.01 nM to about 100 μM.
54. The method of paragraph 44, wherein the contact is in vivo.
55. The method of paragraph 54, wherein the in vivo contact is in a mammal.
56. The method of paragraph 55, wherein the in vivo contact is in a mammal, and wherein the mammal is in need of treatment for damaged muscle tissue.
57. The method of paragraph 56, wherein the damaged muscle tissue is a result of a physical injury or accident, disease, infection, over-use, loss of blood circulation, muscle atrophy, muscle wasting, dystrophic muscle or ageing muscle.
58. The method of any of paragraphs 44-57, wherein the compound comprises quizartinib (AC220), or any salt, ester or chelate thereof.
59. A method for muscle repair or muscle regeneration in a subject having damaged muscle tissue, the method comprising administering a therapeutically effective amount of a compound to the subject, wherein the compound is a kinase inhibitor.
60. The method of paragraph 59, wherein the kinase is a protein kinase.
61. The method of paragraph 60, wherein the protein kinase is a protein tyrosine kinase.
62. The method of paragraph 61, wherein the protein tyrosine kinase is a receptor protein tyrosine kinase.
63. The method of paragraph 62, wherein the receptor protein tyrosine kinase is a member of the RET family.
64. The method of paragraph 61, wherein the receptor protein tyrosine kinase is RET.
65. The method of paragraph 61, wherein the compound interferes with binding of a ligand to the receptor protein tyrosine kinase.
66. The method of paragraph 59, wherein the compound is selected from the group consisting of small organic or inorganic molecules, saccharines, oligosaccharides, polysaccharides, peptides, proteins, peptide analogs and derivatives, antibodies, antibodies fragments, peptidomimetics, nucleic acids, nucleic acid analogs and derivatives, an extract made from biological materials, naturally occurring or synthetic compositions and any combination thereof.
67. The method of paragraph 59, wherein the damaged muscle tissue is the result of a physical injury or accident, disease, infection, over-use, loss of blood circulation, muscle atrophy, muscle wasting, dystrophic muscle or ageing muscle.
68. The method of paragraph 59, wherein the subject is a mammal.
69. The method of any of paragraphs 59-68, wherein the compound comprises quizartinib (AC220), or any salt, ester or chelate thereof
70. The method of any paragraphs 44-69, wherein the compound is selected from the group consisting of

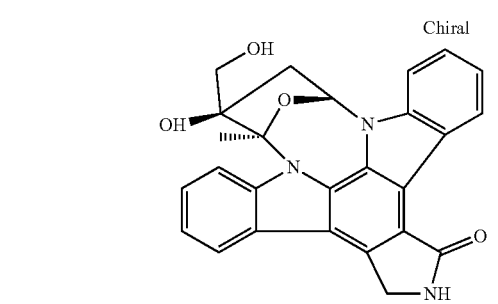
Lestaurtinib (CEP701, ),
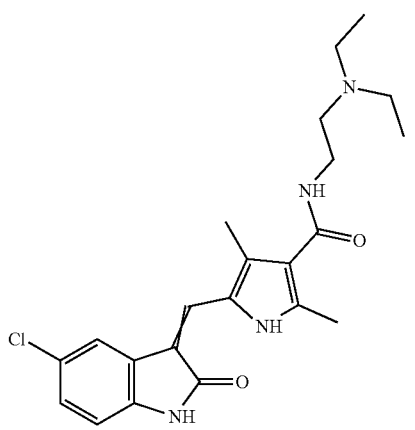
SU11652 ( ),
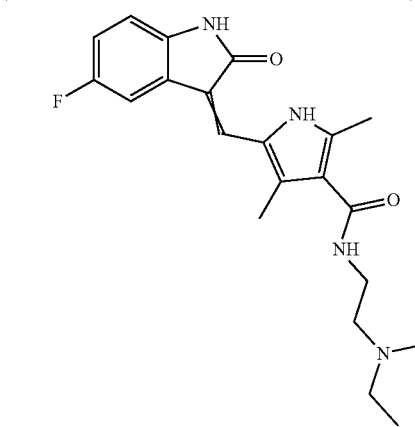
Sunitinib (SU 11248, ),
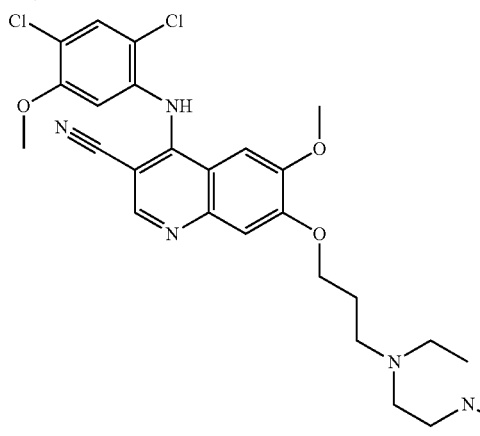
Bosutinib (SKI 606, ),
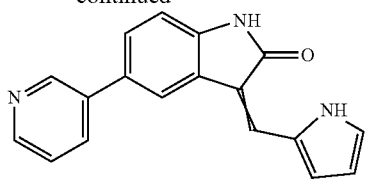
Jak3 Inhibitor VI ( ,
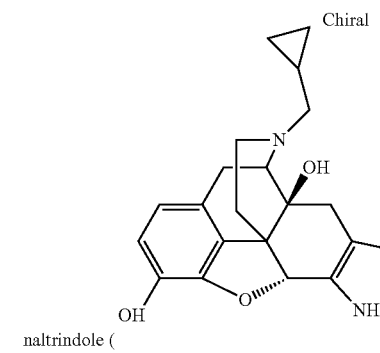
naltrindole ( ),
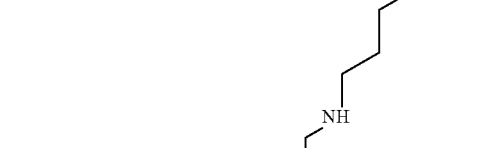
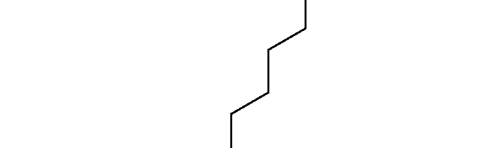
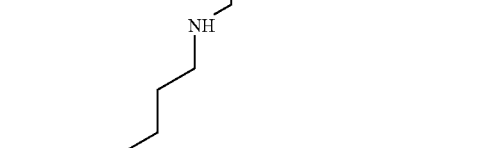
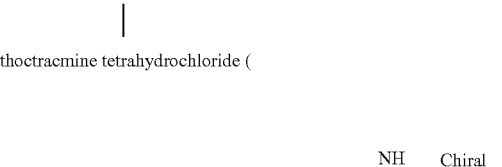
methoctracmine tetrahydrochloride ( ),
histamine R(-)-alpha-methyl-dihydrochloride ( ),

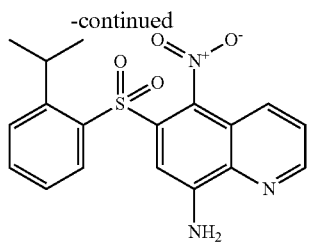

PD160170 ( ),

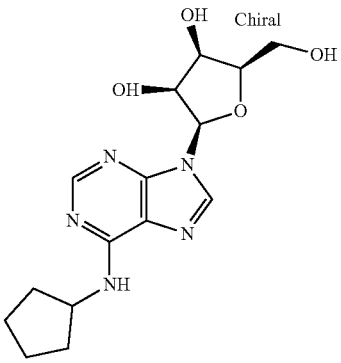

N6-cyclopentyladenosine ( ),

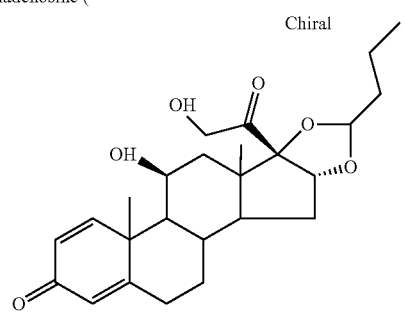

Budesonide ( ), and any combinations thereof.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

The term "modulator" refers to a compound that alters or elicits an activity of a molecule. For example, a modulator may cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator. Without limitations, a modulator can be selected from the group consisting of small or large organic or inorganic molecules; monosaccharides; disaccharides; trisaccharides; oligosaccharides; polysaccharides; biological macromolecules, e.g., proteins, peptides, peptide analogs and derivatives thereof, peptidomimetics, nucleic acids, nucleic acid analogs and derivatives, enzymes, antibodies, portion or fragments of antibodies; an extract made from biological materials such as bacteria, plants, fungi, or animal cells or tissues; naturally occurring or synthetic compositions; and any combinations thereof.

The term "selective modulator" refers to a compound that selectively modulates a target activity.

The term "selectively modulates" refers to the ability of a selective modulator to modulate a target activity to a greater extent than it modulates a non-target activity.

The term "target activity" refers to a biological activity capable of being modulated by a modulator. Certain exemplary target activities include, but are not limited to, binding affinity, signal transduction, enzymatic activity, and the like.

The term "agonist" refers to a compound, the presence of which results in a biological activity of a receptor that is the same as the biological activity resulting from the presence of a naturally occurring ligand for the receptor.

The term "partial agonist" refers to a compound the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "inhibitor" refers to molecules or substances or compounds or compositions or agents or any combination which are capable of inhibiting and/or reducing the activity of the target molecule. As used herein, the term "inhibitor" is interchangeable with the term "antagonist". The term "inhibitor" comprises competitive, non-competitive, functional and chemical antagonists. The term "partial inhibitor" means a molecule or substance or compound or composition or agent or any combination thereof that is capable of incompletely blocking the action of agonists through, inter alia, a non-competitive mechanism.

As used herein, the term "ligand" refers to an agent that binds to a target molecule. A ligand is not limited to an agent that binds to a recognized functional region of the target molecule, e.g., the active site of an enzyme, the antigen-combining site of an antibody, the hormone-binding site of a receptor, a cofactor-binding site, and the like. A ligand can also be an agent that binds any surface or conformational domains of the target compound. Therefore, the ligands encompass agents that in and of themselves may have no apparent or known biological function, beyond their ability to bind to the target in the manner described above. The term ligand encompasses agents that react upon binding and agents that do not react other than by binding.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1—Screening Assay

Satellite cells were harvested from CAG-B-actin-GFP mice, aged 2-4 months old via the FACS isolation method outlined in Sherwood et al 2004 and Cerletti et al 2008. Briefly, all limb muscles and abdominal muscles were harvested from the animals and digested first in a 0.2% collagenase solution, then in a 0.0125% collagenase/0.05% dispase solution. The filtered solution was stained for cell surface markers, and put through FACS. Cells that were negative for Mac1, Sca1 and CD45 and positive for Beta-integrin 1 and CXCR4 were used for the screening assay. Cells were plated directly from the FACS machine at 50 cells/well, into 96-well plates coated with 10 ug/mL laminin (4-6 hours at 37 C, then partially removed). Media for the screen was Ham's F-10 supplemented with 10% heat-inactivated horse serum, 1× penicillin/streptomycin and 1× L-glutamine. Basic FGF (bFGF) was added only to the positive control wells; all other wells received media only. The day of plating was called Day 0. The day after plating, Day 1, compounds were added. All compounds were dissolved in DMSO, and initially tested at 10 uM, 1 uM or 0.1 uM in duplicate. The negative control for each plate was the same concentration of DMSO (no compounds dissolved). Compounds were incubated with the cells until Day 4, with no media change. bFGF was spiked into positive control wells daily. On Day 4, plates were fixed in 4% paraformaldehyde and washed with phosphate buffered saline. Plates were imaged directly on the Opera Confocal imager, since the cells were readily visible from the CAG-EGFP-Beta-actin transgene. An Acapella script was used to count the number of cells in each well. Wells were scored for proliferation based on the cell counts (DMSO-treated wells usually had around 50 cells at the end of the assay, bFGF-treated wells usually had 150-250 cells at the end). We selected compounds as hits if they had cell numbers greater than or equal to one (or, for the second session of screening, three) standard deviation(s) from the DMSO controls. Compounds thus selected were then tested in an initial dose curve, usually concentrations between 20 nM-30 uM commensurate with the concentration flagged as a hit. We called compounds active if they were able to cause proliferation to cell numbers at least two standard deviations over the DMSO negative control. Any compounds that were found to be active in the dose curve were re-supplied from the original vendors. Re-supplied compounds were again tested in a dose curve for proliferation ability. Compounds still found to be active were then put in the queue for optimization and characterization.

TABLE 1

Compounds Screened in Session One

| Composition by Target Class | No. of compounds |
|---|---|
| Kinase Inhibitors | 106 |
| GPCR Drug List | 20 |

TABLE 1-continued

Compounds Screened in Session One

| Composition by Target Class | No. of compounds |
|---|---|
| Diverse set of GPCR Ligands | 78 |
| Others | 11 |
| Total | 215 |

TABLE 2

Compounds Screened in Session Two

| Composition by Target Class | No. of compounds |
|---|---|
| HDAC | 10 |
| Hh Ag + An | 17 |
| Neuropeptides | 5 |
| GPCR-Dopamine | 29 |
| GPCR-Serotonin | 31 |
| GPCR-Histamine | 27 |
| g-secretase (notch) | 7 |
| ionophore | 5 |
| Ion channels | 25 |
| Kinase Inhibitors | 39 |
| Total | 195 |

As described above, the inventors screened a set of 215 compounds comprised primarily of kinase inhibitors and GPCR ligands. The inventors assayed these compounds at 1 µM, and counted as potential hits those compounds that scored greater than one standard deviation over the DMSO-treated negative control. Using these criteria, the inventors identified 20 compounds from the set as hits. The inventors then tested each of these 20 compounds in a dose response assay to validate their activity. Five compounds found to have activity using this method are shown in Table 3. Dose response curves for the five compounds are shown in FIGS. 9A-13.

TABLE 3

| Compound | Library Source | Initial hit Conc. | Target |
|---|---|---|---|
| Lestaurtinib (CEP-701) | Kinases | 1 uM | Flt3 Kinase, Jak2, ROR gamma? |
| SU 11652 | Kinases | 1 uM | PDGFR/EGFR |
| SU 11248 (Sunitinib) | Kinases | 1 uM | EGFR, Flt3 kinase |
| Bosutinib (SKI 606) | Kinases | 1 uM | Bcr-abl, SRC kinase |
| JAK3 Inhibitor VI | Kinases | 1 uM | |

Three of the compounds (Sunitinib (SU11248), JAK3 inhibitor VI, and Lestaurtinib/CEP701) were retested and found to be active in the retest. Each compound promoted proliferation of the input SMP cells similar to that seen in the bFGF positive control (4.7±1.4 for Sunitinib and Lestaurtinib, 3.7±1.1 for JAK3 inhibitor VI). The DMSO-treated cells proliferated to a level of 1±0.3 in both trials.

In addition, the inventors also examined whether CEP 701 can synergize with bFGF to achieve even higher levels of SMP proliferation. For these experiments, 300 cells were plated in each well instead of the 50 cells/well used for the screen and subsequent dose response assays. This change in protocol was introduced in an effort to reduce the variability in the assays. Under these conditions 0.05 µM CEP701 was added the day after plating the purified SMPs, and 5 ng/mL bFGF was added to the appropriate samples on a daily basis. Three days after plating the media was changed and fresh compound was added. This additional change in the protocol was introduced both to improve viability and reduce variability. The plates were fixed four days after plating.

Figure 15:
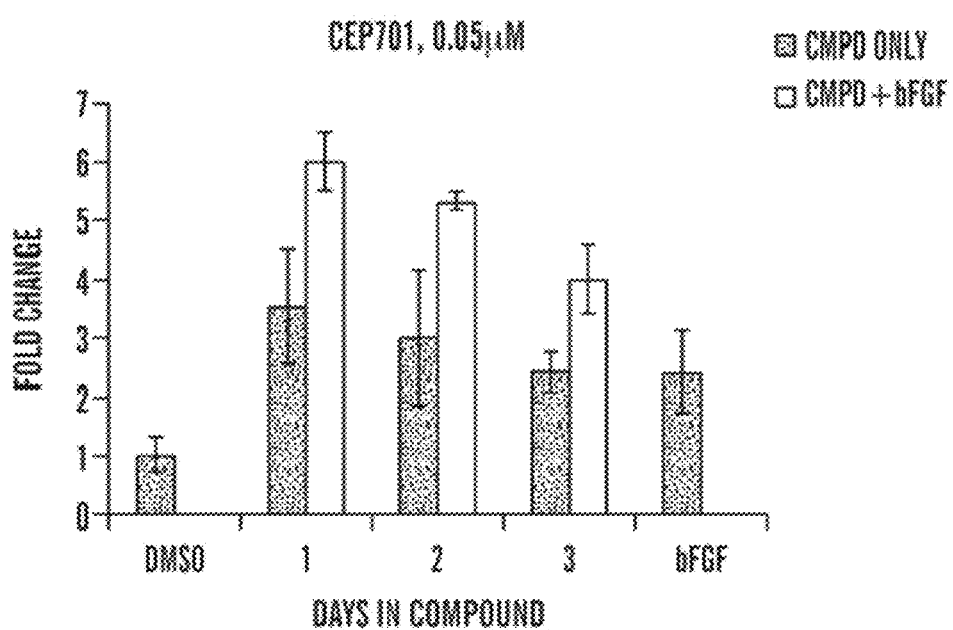
Figure 16:
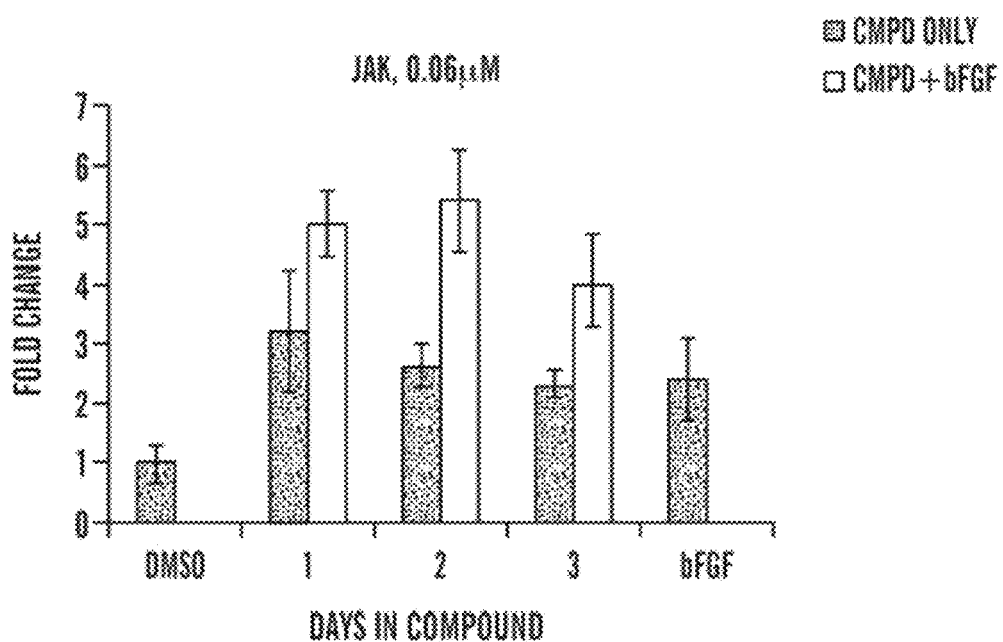
Figure 17:
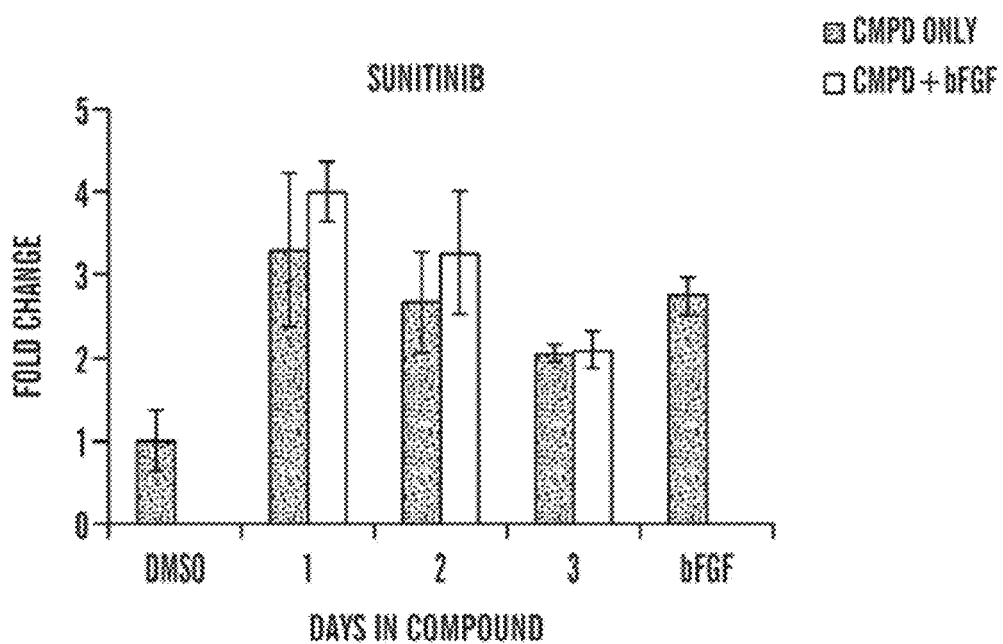

Cultures treated with both CEP701 and bFGF showed an 8-fold increase in proliferation (FIG. 14), indicating that CEP701 and bFGF can act additively to increase SMP expansion in vitro. Because changing the media seemed to lead to increased viability in the cells, the inventors decided to try removing the compounds several days before fixation to allow the cells to recover. For the following experiments, compounds were added the day after plating (Day 1). Compound was refreshed daily, until it was removed from the cultures completely on the day as indicated below. Cells were then cultured in media without supplemented compounds until fixation on Day 4. The inventors discovered that two days of recovery time was advantageous to the cultures. The inventors confirmed that discovered that CEP-701 can work additively with bFGF (FIG. 15). Additionally, while Jak3 inhibitor VI also worked additively with bFGF (FIG. 16), Sunitinib did not worked additively with bFGF (FIG. 17).

In order to assess the effects these compounds have on the identity of the SMPs, the inventors studied the ability of the treated SMPs to differentiate in culture. For these experiments, 300 cells were plated in each well at Day 0 in our standard proliferation media (10% horse serum in F-10). Compounds were added at Day 1 and SMPs were allowed to proliferate for three days. At Day 4, the media was switched to differentiation media (10% horse serum, 10% FBS, 0.5% chick embryo extract in high-glucose DMEM). Cultures were then incubated for three or four days under differentiation conditions and fixed on Day 7 or Day 8. They were then stained with Hoechst and anti-myosin heavy chain antibody.

As shown in FIGS. 18-20, treatment with CEP701, Sunitinib, or Jak3 inhibitor VI did not affect the ability of expanded SMPs to differentiate and fuse to form myotubes. Additionally, satellite cells that had been exposed to CEP701 for 3 days and then allowed to recover for two days before being put into differentiation conditions were also able to fuse into myotubes (data not shown).

The inventors focused on CEP701 for further studies. The inventors next studied additive effect of CEP701 with TGF-beta inhibitors. TGF-Beta inhibitors are known to promote proliferation and prevent differentiation of satellite cells. Addition of Alk5 inhibitor II to the cultures produced a slight increase in proliferation. However, little additive effect was seen on addition of CEP701 and TGF-beta inhibitor (FIG. 21).

Next the inventors tested the specificity of CEP701 for proliferating satellite cells. The inventor isolated the Sca1-positive population of fibroblasts from the muscle preparation, obtained via FACS. Either 500 or 3000 fibroblasts were plated in each well, and cultured in DMEM supplemented with 10% FBS. Compound was added the day after plating, and refreshed daily. Plates were fixed five days after plating and stained for the proliferation marker Ki67. As seen in FIG. 22, no difference in the percentage of proliferating cells between those exposed to CEP701 (right panel) and those exposed to DMSO (left panel) was seen. In addition, CEP701 had no effect on primary fibroblasts (FIG. 23).

In another experiment, the inventors tested the CEP701 compound in aged tissue. The aged mice were 15 months old at the time of the experiment. The conditions used for the assay were the same as those used for young animals. After FACS, 300 cells/well were plated on Day 0 in the inventors' standard proliferation media (10% horse serum in F-10). Compound was added at Day 1 at indicated concentrations, and refreshed daily. At Day 4, compound was withdrawn and replaced with media only. Plates were fixed and imaged at Day 6.

As seen in FIGS. 24 and 25, 50 nM CEP701 appeared to be the optimum concentration for aged cells as well as young cells. In both cases, exposure to 50 nM CEP701 under the described conditions resulted in approximately a six-fold increase in the number of cells. CEP701 and bFGF were able to act additively in cultures of old cells, producing approximately a ten-fold increase in cell number.

In another experiment, the inventors screened a new set of 200 compounds. This set was primarily focused on GPCR ligands, with some kinase inhibitors and other annotated compounds. The inventors screened the compounds at 10 uM in duplicate, except the kinase inhibitors which were screened at 1 uM in duplicate. Compounds were scored as potential hits if they increased proliferation of input SMPs at levels greater than three standard deviations over the negative control in either of the replicates. Using these criteria, the inventors identified and validated 2 hits (N6-cyclopentyladenosine, an adenosine receptor agonist, and Budesonide, a glucocorticoid steroid) in subsequent dose response curves (FIGS. 26 and 27).

After additional testing, we ultimately decided to resupply Budesonide, and N6-cyclopentyladenosine (CPA) from the original vendor in order to test a different batch of the compounds. We performed dose responses on all the re-supplied compounds, plating 50 cells in each well as we had done during the screen and the first dose response tests In this experiment, the DMSO negative control had a normalized value of 1±0.4 and the bFGF positive control had a value of 5.6±1.7. Both CPA and Budesonide were effective and produced proliferation levels much greater than that seen in the negative control. Without wishing to be bound by a theory, repeating these assays under the optimized experimental conditions the inventors have developed (300 cells/well plus a media change to refresh compounds after two days exposure) can improve both the variability of the assay as well as the proliferation response.

As with the hits from the first set of compounds screened, the inventors tested these compounds for ability to synergize with bFGF. Using inventors' standard culture conditions (10% horse serum in F-10), compounds were added to cells the day after plating, and refreshed daily until removed from the cultures as indicated. Cells were then grown in media without supplemented compounds until fixation on Day 4.

CPA (30 µM) was seen to synergize with bFGF in vitro. The combination of CPA and bFGF showed a fifteen-fold increase in the cell number, as compared with approximately a six-fold increase with bFGF alone (FIG. 28). However, combination of Budesonide with bFGF provided no additional increase as compared to bFGF alone (FIG. 29).

The inventors also assessed effects these compounds were having on the identity of the satellite cells and their ability to differentiate in culture. For these experiments, 300 cells were plated in each well at Day 0 in our standard proliferation media (10% horse serum in F-10). Compounds were added at Day 1 and SMPs were allowed to proliferate for three days. At Day 4, the media was switched to differentiation media (10% horse serum, 10% FBS, 0.5% chick embryo extract in high-glucose DMEM). Cultures were then incubated for three or four days under differentiation conditions and fixed on Day 7. They were then stained with Hoechst and anti-myosin heavy chain antibody. As can be seen in the FIGS. 29 and 30, satellite cells exposed to the compound are able to fuse into myosin heavy chain-positive myotubes.

The inventors then tested whether these compounds can work additively with TGF-Beta inhibitors. A slight increase in proliferation was seen when the cells were treated with both CPA and Alk5 inhibitor II as compared to CPA and Alk5 inhibitor II alone (FIG. 31).

In this study, the inventors carried out a screen designed to identify compounds that are able to cause satellite cells to proliferate in vitro. The inventors discovered several compounds that can cause proliferation, both in the presence and absence of bFGF. The compounds gave rise to satellite cell populations that differentiate normally and carried normal markers for differentiation state. These results show that treatment with these compounds allow the satellite cell population to proliferate normally and contribute to muscle repair in disease states.

Example 2

Satellite cells were harvested from CAG-B-actin-GFP mice, aged 2-4 months old via the FACS isolation method as outlined in Example 1. Briefly, all limb muscles and abdominal muscles were harvested from the animals and digested first in a 0.2% collagenase solution, then in a 0.0125% collagenase/0.05% dispase solution. The filtered solution was stained for cell surface markers, and put through FACS. Cells that were negative for Mac1, Sca1 and CD45 and positive for Beta-integrin 1 and CXCR4 were used for the screening assay. Cells were plated directly from the FACS machine at 50 cells/well, into 96-well plates coated with 10 ug/mL laminin (4-6 hours at 37° C., then partially removed). Media for the screen was Ham's F-10 supplemented with 10% heat-inactivated horse serum, IX penicillin/streptomycin and IX L-glutamine. Basic FGF (bFGF) was added only to the positive control wells; all other wells received media only. The day of plating was called Day 0.

The day after plating (Day 1) the compounds were added, as illustrated in FIG. 33. All compounds were dissolved in DMSO, and initially tested at 10 uM, 1 uM or 0.1 uM in duplicate. The negative control for each plate was the same concentration of DMSO (no compounds dissolved). Compounds were incubated with the cells until Day 4, with no media change. bFGF was spiked into positive control wells daily. On Day 4, plates were fixed in 4% paraformaldehyde and washed with phosphate buffered saline. Plates were imaged directly on the Opera Confocal imager, since the cells were readily visible from the CAG-EGFP-Beta-actin transgene. An Acapella script was used to count the number of cells in each well. Wells were scored for proliferation based on the cell counts (DMSO-treated wells usually had around 50 cells at the end of the assay, bFGF-treated wells usually had 150-250 cells at the end), Compounds were selected as hits if they had cell numbers greater than or equal to one (or, for the second session of screening, three) standard deviation(s) from the DMSO controls. Compounds thus selected were then tested in an initial dose curve; usually concentrations between 20 nM-30 uM commensurate with the concentration flagged as a hit. Compounds were deemed to be active if they were able to cause proliferation to cell numbers at least two standard deviations over the DMSO negative control. Any compounds that were found to be active in the dose curve were re-supplied from the original vendors. Re-supplied compounds were again tested in a dose curve for proliferation ability. Compounds still found to be active were then put in the queue for optimization and characterization.

The inventors screened a set of approximately 400 compounds from the custom screening library illustrated in FIG. 34. The inventors assayed these compounds at 1 µM, and counted as potential hits those compounds that scored greater than one standard deviation over the DMSO-treated negative control. Using these criteria, the inventors identified approximately 10 compounds from the set as hits that were capable of increasing in vitro satellite cell proliferation. The inventors then tested each of these compounds in a dose response assay to validate their activity. As illustrated in FIG. 35, four of the compounds that were found to increase in vitro satellite cell proliferation were Lestaurtinib (CEP701), Sunitinib (SU11248), JAK3 inhibitor VI, and N6-cyclopentyladenosine (CPA). Lestaurtinib (CEP701) was identified as a top hit, was effective at nanomolar doses and had target overlap with several other hit compounds.

Additionally, Lestaurtinib (CEP701) increased proliferation of aged satellite cells in vitro (FIG. 36), increased proliferation of human satellite cells and did not increase proliferation of fibroblasts.

The inventors then tested each of these compounds in a dose response assay to validate their activity, as depicted in FIG. 37A. Dose response curves for Lestaurtinib (CEP701), Sunitinib (SU11248), JAK3 inhibitor VI, and N6-cyclopentyladenosine (CPA) are shown in FIG. 37B.

In addition to Lestaurtinib (CEP701), Quizartinib (AC220), a small molecule receptor tyrosine kinase inhibitor, also demonstrated an ability to expand human satellite cells at low doses. As illustrated in FIG. 38, both CEP-701 and AC220 increased human satellite cells by more than 2-fold at a concentration of 1 nM relative to the DMSO control.

As illustrated in FIG. 39, a differentiation media comprising 5% horse serum and those compounds identified as hits (e.g., CEP701, SU11248, JAK3 inhibitor VI, CPA and Tyr AG490) drive myoblast differentiation. Similarly, FIG. 40 demonstrates that CEP701 enhances myoblast differentiation in differentiation media relative to the DMSO control, as evidenced by the observed increase in both myoblast area and length.

The present inventors next sought to determine whether CEP701-treated cells retain engraftability by performing the experimental protocol depicted in FIG. 41A, by engrafting tubulin>GFP satellite cells into injured mdx muscle and administering CEP701 or a DMSO control. As illustrated in FIG. 41B, CEP701 treated cells resulting in an increased number of GFP+ fibers per section, relative to the DMSO control.

The present inventors next sought to determine whether CEP701 treatment increases regenerating fiber size and satellite cell number in vivo. CEP701 was administered subcutaneously to the mice post-CTX injury, followed by harvesting of the tissue, as depicted in FIG. 42A. Regenerating muscle fibers are eMHC+. As illustrated in FIGS. 42B-42D, treatment with CEP701 increased both regenerating fiber size and satellite cell number in vivo in both adult and aged mice.

The present inventors also performed an in vitro binding assay against active site fragments (KINOMEscan) in an effort to identify those multiple hit compounds that inhibit receptor tyrosine kinases (RTKs). As shown in Table 4 below, CEP701, AC220 and sunitinib each inhibit multiple RTKs (numbers are Kd in nM; expression in primary myoblasts).

TABLE 4

| Kinase | Ligand | CEP-701 | AC220 | Sunitinib | FACS | Imaging | Literature | qPCR* (Ct) |
|---|---|---|---|---|---|---|---|---|
| Flt3 | FL | 8.5 | 1.6 | 0.47 | NO | | | ~27-28 |
| Flt4 | VEGF | 17 | 41 | 50 | | | | ~32-33 |
| RET | GDNF | 20 | 9.9 | 12 | YES | YES | | ~27-28 |
| PDGFRβ | PDGF | 28 | 7.7 | 0.075 | NO | | | ~27-28 |
| M-CSF1R | CSF1 | 110 | 12 | 2 | | NO | | ~30-34 |
| VEGFR2 | VEGF | 110 | 87 | 1.2 | | | | ~31-33 |
| FLT1 | VEGF | 120 | 41 | 1.8 | | | Yes? | ~31-32 |
| c-KIT | SCF | 150 | 4.8 | 0.37 | | | | ~33 |
| PDGFRα | PDGF | 380 | 11 | 0.79 | NO | | | ~31-32 |
| DDR1 | Collagen | 510 | 81 | 2000 | | | | |

RET proto-oncogene is the receptor for the GDNF ligand family, which includes glial derived neurotrophic factor, neurturin, artemin and persephin, and is important for the development and function of several tissue types, including the nervous system. The RET proto-oncogene activates several downstream pathways, including JAK/STAT. As illustrated in FIG. 43A, the multiple hit compounds CEP701, AC220 and sunitinib that are identified in Table 4 inhibit the PDGFR family of RTKs. Phospho-RET levels are elevated in injured muscle, as illustrated in FIG. 43B, which compares the fold change in phospho-RET in both uninjured contralateral tibialis anterior (TA) muscle to that observed 2 days post-cardiotoxin injury. As illustrated in FIG. 43B, 2 days post-cardiotoxin injury, an approximately 8-fold increase in phospho-RET was observed by ELISA relative to uninjured contralateral TA muscle.

Satellite cells express RET in vitro, as shown in FIGS. 44A-44B. As illustrated in FIGS. 45A-45D, CEP701 treatment inhibits RET phosphorylation in vitro.

FIG. 46 shows the results of a study evaluating the effects of the in vitro deletion of RET. Using a conditional RET mutant and reporter, the present inventors were able to determine that the RET promoter is active in at least 25% of satellite cells (FIG. 47) and that RET knockout cells proliferate better than wild-type cells in vitro (FIG. 48). FIG. 49 demonstrates the fold change relative to control of untreated FLT3 and RET knockout cells.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of increasing satellite cell proliferation, the method comprising: contacting a satellite cell with vorinostat, in an amount effective to increase satellite cell proliferation.

2. The method of claim 1, wherein the contacting is in vivo.

3. The method of claim 2, wherein the in vivo contacting is in a human.

4. The method of claim 2, wherein the in vivo contacting is in a subject, wherein the subject is in need of treatment for damaged muscle tissue.

5. The method of claim 4, wherein the damaged muscle tissue is the result of a physical injury or accident, disease, infection, over-use, loss of blood circulation, or muscle atrophy or wasting.

6. The method of claim 4, wherein the damaged muscle tissue is the result of muscle atrophy/wasting.

7. A method for muscle repair or regeneration in a subject having damaged muscle tissue, the method comprising administering to the subject vorinostat, in an amount effective to increase satellite cell proliferation.

8. The method of claim 7, wherein the subject is human.

9. The method of claim 7, wherein the damaged muscle tissue is the result of a physical injury or accident, disease, infection, over-use, loss of blood circulation, or muscle atrophy or wasting.

10. The method of claim 7, wherein the damaged muscle tissue is the result of muscle atrophy/wasting.

* * * * *